United States Patent [19]
Sim et al.

[11] Patent Number: 5,993,827
[45] Date of Patent: Nov. 30, 1999

[54] **BINDING DOMAINS FROM *PLASMODIUM VIVAX* AND *PLASMODIUM FALCIPARUM* ERYTHROCYTE BINDING PROTEINS**

[75] Inventors: Kim Lee Sim, Gaithersburg, Md.; Chetan Chitnis, Washington, D.C.; Louis H. Miller, Bethesda, Md.; David S. Peterson, Rockville, Md.; Xin-Zhuan Su, Rockville, Md.; Thomas E. Wellems, Rockville, Md.

[73] Assignee: The United States of America as represented by the Secretary, Department of Health and Human Services, Washington, D.C.

[21] Appl. No.: 08/487,826

[22] Filed: Jun. 7, 1995

Related U.S. Application Data

[63] Continuation-in-part of application No. 08/119,677, Sep. 10, 1993, abandoned
[60] Provisional application No. PCT/US94/10230, Sep. 7, 1994.
[51] Int. Cl.$^6$ .......................... A61K 39/015; C12N 15/30
[52] U.S. Cl. ...................................... 424/268.1; 424/185.1; 424/272.1; 435/69.1; 435/252.3; 435/320.1; 530/350; 530/395
[58] Field of Search .......................... 536/23.5; 530/300, 530/350; 424/185.1, 272.1, 268.1; 435/320.1, 252.3

[56] References Cited

U.S. PATENT DOCUMENTS 5,198,347   3/1993   Miller et al. ........................... 435/69.1

FOREIGN PATENT DOCUMENTS

WO9318160   9/1993   WIPO .

OTHER PUBLICATIONS

Fang, X., et al., "Cloning of the *Plasmodium vivax* Duffy receptor", Molecular and Biochemical Parasitology, 44: 125–132 (1991).

Adams J.H., et al., The Duffy Receptor Family of *Plasmodium knowlesi*Is Located within the Micronemes of Invasive Malaria Merozoites, Cell 63: 141–153, (1990).

Camus, D., et al., "A *Plasmodium falciparum* Antigen that Binds to Host Erythrocytes and Merozoites", Science 230: 553–556 (1985).

Barnwell, J.W., et al., "In vitro Evaluation of the Role of the duffy Blood Group in Erythrocyte Invasion by *Plasmodium Vivax*," J. Exp. Med., 169: 1795–1802 (May 1989).

Sim, B.K.L., et al., "Primary Structure of the 175K *Plasmodium falciparum* Erythrocyte Binding Antigen and Indentification of a Peptide Which Elicites Antibodies That Inhibit Malaria Merozoite Invasion", J. of Cell Biology, 111: 1877–1884 (Nov. 1990).

Haynes, J.D., et al., "Receptor–Like Specificity of a *Plasmodium Knowlesi* Malarial Protein that Binds to Duffy Antigen Ligands on Erythrocytes", J. Exp. Med., 167: 1873–1881 (Jun. 1988).

Miller, L.H., et al., "Indentification of *Plasmodium knowlesi* erythrocyte binding proteins", Molecular and Biochemical Parasitology, 31: 217–222 (1988).

Wertheimer, S.P., et al., "*Plasmodium vivax* Interaction with the Human Duffy Blood Group Glycoprotein: Indentification of a Parasite Receptor–like Protein", Experimental Parasitology, 69: 340–350 (1989).

Adams, J.H., et al., "A family of erythrocyte binding proteins of *malaria parasites*", Proc. Natl. Acad. Sci. USA, 89: 7085–7089 (Aug. 1992).

Dalton, J.P., et al., "Blocking of the receptor–mediated invasion of erythrocytes by *Plasmodium knowlesi* malaria with sulfated polysaccarides and glycosaminoglycans", Eur. J. Biochem., 195: 789–794 (1991).

Orlandi, P.A., et al., "Characterization of the 175–kilodalton erythrocyte binding antigen of *Plasmodium falciparum*", Molecular and Biochemical Parasitology, 40: 285–294 (1990).

Holt, E.H., et al., "Erythrocyte Invasion by two *Plasmodium Falciparum* Isolates Differing in Sialic Acid Dependency in the Presence of Glycophorin A Antibodies", Am. J. Trop. Med. Hyg., 40(3): 245–251 (Mar. 1989).

Perkins, M.E., et al., "Sialic Acid–Dependent Binding of *Plasmodium falciparum* Merozoite Surface Antigen, Pf200, to Human Erythrocytes," J. of Immunology, 141(9): 3190–3196 (Nov. 1, 1988).

Chitnis, Chetan E., and Miller, Louis H., *Identification of the Erythrocyte Binding Domains* . . . , J. Exper. Med. 180:497–506, Aug. 1994.

Sim, et al., *Receptor and Ligand Domains for Invasion of Erythrocytes by Plasmodium Falciparum*, Science 264:1941–1944, Jun. 24, 1994.

Primary Examiner—Thomas M. Cunningham
Attorney, Agent, or Firm—Knobbe Martens Olson & Bear

[57] ABSTRACT

The present invention provides isolated polypeptides useful in the treatment and prevention of malaria caused by *Plasmodium falciparum* or *P. vivax*. In particular, the polypeptides are derived from the binding domains of the proteins in the DBL family as well as the sialic acid binding protein (SABP) on *P. falciparum* merozoites. The polypeptides may also be derived from the Duffy antigen binding protein (DABP) on *P. vivax* merozoites.

20 Claims, 6 Drawing Sheets

| | | |
|---|---|---|
| Family 2 Cont'd | EBL-e2 | KGGDFFQLREDWTSNRETVWKALICHA-$X_{11}$-C-$X_{23}$-VPQYLRWFEEWAEDFCRKKKKKLENLQKQC--$X_6$----C-$X_{15}$-- |
| | Proj3 F1 | NDPEFFKLREDWWTANRETVWKAITCNA-$X_9$--C-$X_{23}$-VPQYLRWFEEWAEDFCRKKNKKIKDVKRNC-$X_{12}$--C-$X_{22}$-- |
| | Proj3 F2 | KKPAYKKLRADWWEANRHQVWRAMKCAT-$X_4$--C-$X_8$--IPQRLRWMTEWAEWYCKAQSQEYDKLKKIC--$X_{11}$-C-$X_6$--- |
| | Proj3 F3 | SKSPSGLSRQEWWKTNGPEIWKGMLCAL-$X_{37}$-------KPQFLRWMIEWGEEFCAERQKKENIIKDAC--$X_8$---C-$X_3$-- |
| | E31a | KISNSIRYRKSWWETNGPVIWEGMLCAL-$X_{42}$-------RPQFLRWLTEWGENFCKEQKKEYKVLLAKC--$X_{11}$-C-$X_3$-- |
| | | |
| Family 1 Cont'd | DABP | VPPCQNACKSYDQ WITRKKN-$X_{56}$---------CX--C |
| | SABP F1 | EKECIDPCMKYRD WIIRSKF-$X_{41}$-C-$X_7$------CX---C |
| | SABP F2 | DDNCKSKCNSYKE WISKKKK-$X_{36}$-C-$X_{20}$------CXX-C |
| | EBL-e1 | EKKCKNACSSYEK WIKERKN-$X_{38}$-C-$X_{19}$------CXX-C |
| | | |
| Family 2 Cont'd | EBL-e2 | CTNCSVWCRMYET WIDNQKK-$X_{68}$-C-$X_{30}$------CXX-C |
| | Proj3 F1 | CISCLYACNPYVD WIDNQKK-$X_{69}$-C-$X_{40}$------CXX-C |
| | Proj3 F2 | CGKCKAACDKYKEEIEKWNEQWRK-$X_{73}$-C-$X_6$-C-$X_{30}$-CXX-C |
| | Proj3 F3 | KHRCNQACRAYQE YVENKKK-$X_{43}$-C-$X_4$------CX---C |
| | E31a | CVACKDQCKQYHS WIGIWID-$X_{42}$-C-$X_8$-------CXXXC |

Concensus amino acid sequences and the synthetic oligonucleotide primers designed from them.

I.  UNIEBP5 and 5A:   P R R Q K/E L C                                           (SEQ ID NO:34)

UNIEBP5, for A+T biased condon usage:
    CC(A/G)-AG(G/A)-AG(G/A)-CAA-(G/A)AA-(C/T)TA-TG         (SEQ ID NO:35)

UNIEBP5A, for G+C biased codon usage:
    CC(C/G)-(C/A)G(C/G)-(C/A)G(C/G)-CAG-CAG-(C/T)T(C/G)-TG   (SEQ ID NO:36)

II. UNIEBP5 B and C:   F A D I/Y G/R D I                                        (SEQ ID NO:37)

UNIEBP5B, for A+T biased codon usage:
    TTT-GC(A/T)-GAT-(A/T)(A/T)(A/T)-(G/C)G(A/T)-GAT-AT       (SEQ ID NO:38)

UNIEBP5C, for G+C biased codon usage:
    TTC-GC(G/C)-GAT-(A/T)(A/T)C-(G/C)G(G/C)-GAC-AT           (SEQ ID NO:39)

III. UNIEBP3 and 3A:   P Q F L/F R W                                            (SEQ ID NO:40)

UNIEBP3, for A+T biased codon usage:
    CCA-(A/T)C(T/G)-(T/G)A(A/G)-(A/G)AA-TTG-(A/T)GG         (SEQ ID NO:41)

UNIEBP3A, for G+C biased codon usage:
    CCA-(C/G)C(G/T)-G(A/T)A-GA(A/T)-CTG-(C/G)GG              (SEQ ID NO:42)

IV. UNIEBP3 and C:    E W G D/E D/E Y/F C                                       (SEQ ID NO:43)

UNIEBP3B, for A+T biased codon usage:
    CA-A(A/T)A-(A/T)TC-(A/T)TC-(A/T)CC-CCA-TTC                (SEQ ID NO:44)

UNIEBP3C, for G+C biased codon usage:
    CA-G(A/T)A-(G/C)TC-(G/C)TC-(G/C)CC-CCA-CTC                (SEQ ID NO:45)

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
        (A) LENGTH: 4084 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
    (A) ORGANISM: Plasmodium vivax (xi) SEQUENCE DESCRIPTION: SEQ ID NO:1:

```
AAGCTTTTAA AAATAGCAAC AAAATTTCGA ACATTGCCA CAAAAATTTT ATGTTTTACA      60
TATATTTAGA TTCATACAAT TTAGGTGTAC CCTGTTTTTT GATATATGCG CTTAAATTTT    120
TTTTTCGCTC ATATGTTTAG TTATATGTGT AGAACAACTT GCTGAATAAA TTACGTACAC    180
TTTCTGTTCT GAATAATATT ACCACATACA TTTAATTTTA AATACTATGA AAGGAAAAAA    240
CCGCTCTTTA TTTGTTCTCC TAGTTTTATT ATTGTTACAC AAGGTATCAT ATAAGGATGA    300
TTTTTCTATC ACACTAATAA ATTATCATGA AGGAAAAAAA TATTTAATTA TACTAAAAAG    360
AAAATTAGAA AAAGCTAATA ATCGTGATGT TTGCAATTTT TTTCTTCATT TCTCTCAGGT    420
AAATAATGTA TTATTAGAAC GAACAATTGA ACCCTTCTA GAATGCAAAA ATGAATATGT     480
GAAAGGTGAA AATGGTTATA AATTAGCTAA AGGACACCAC TGTGTTGAGG AAGATAACTT    540
AGAACGATGG TTACAAGGAA CCAATGAAAG AAGAAGTGAG GAAAATATAA AATATAAATA    600
TGGAGTAACG GAACTAAAAA TAAAGTATGC GCAAATGAAT GGAAAAAGAA GCAGCCGCAT    660
TTTGAAGGAA TCAATTTACG GGGCGCATAA CTTTGGAGGC AACAGTTACA TGGAGGGAAA    720
AGATGGAGGA GATAAAACTG GGGAGGAAAA AGATGGAGAA CATAAAACTG ATAGTAAAAC    780
TGATAACGGG AAAGGTGCAA ACAATTTGGT AATGTTAGAT TATGAGACAT CTAGCAATGG    840
CCAGCCAGCG GGAACCCTTG ATAATGTTCT TGAATTTGTG ACTGGGCATG AGGGAAATTC    900
TCGTAAAAAT TCCTCGAATG GTGGCAATCC TTACGATATT GATCATAAGA AAACGATCTC    960
TAGTGCTATT ATAAATCATG CTTTTCTTCA AAATACTGTA ATGAAAAACT GTAATTATAA   1020
GAGAAAACGT CGGGAAAGAG ATTGGGACTG TAACACTAAG AAGGATGTTT GTATACCAGA   1080
TCGAAGATAT CAATTATGTA TGAAGGAACT TACGAATTTG GTAAATAATA CAGACACAAA   1140
TTTTCATAGG GATATAACAT TTCGAAAATT ATATTTGAAA AGGAAACTTA TTTATGATGC   1200
TGCAGTAGAG GGCGATTTAT TACTTAAGTT GAATAACTAC AGATATAACA AAGACTTTTG   1260
CAAGGATATA AGATGGAGTT TGGGAGATTT TGGAGATATA ATTATGGGAA CGGATATGGA   1320
AGGCATCGGA TATTCCAAAG TAGTGGAAAA TAATTTGCGC AGCATCTTTG GAACTGATGA   1380
AAAGGCCCAA CAGCGTCGTA AACAGTGGTG GAATGAATCT AAAGCACAAA TTTGGACAGC   1440
AATGATGTAC TCAGTTAAAA AAAGATTAAA GGGGAATTTT TATATGGATTT GTAAATTAAA   1500
TGTTGCGGTA AATATAGAAC CGCAGATATA TAGATGGATT CGAGAATGGG GAAGGGATTA   1560
CGTGTCAGAA TTGCCCACAG AAGTGCAAAA ACTGAAAGAA AAATGTGATG GAAAAATCAA   1620
TTATACTGAT AAAAAAGTAT GTAAGGTACC ACCATGTCAA AATGCGTGTA AATCATATGA   1680
TCAATGGATA ACCAGAAAAA AAAATCAATG GGATGTTCTG TCAAATAAAT TCATAAGTGT   1740
AAAAAACGCA GAAAAGGTTC AGACGGCAGG TATCGTAACT CCTTATGATA TACTAAAACA   1800
GGAGTTAGAT GAATTTAACG AGGTGGCTTT TGAGAATGAA ATTAACAAAC GTGATGGTGC   1860
ATATATTGAG TTATGCGTTT GTTCCGTTGA AGAGGCTAAA AAAAATACTC AGGAAGTTGT   1920
GACAAATGTG GACAATGCTG CTAAATCTCA GGCCACCAAT TCAAATCCGA TAAGTCAGCC   1980
TGTAGATAGT AGTAAAGCGG AGAAGGTTCC AGGAGATTCT ACGCATGGAA ATGTTAACAG   2040
TGGCCAAGAT AGTTCTACCA CAGGTAAAGC TGTTACGGGG GATGGTCAAA ATGGAAATCA   2100
GACACCTGCA GAAAGCGATG TACAGCGAAG TGATATTGCC GAAAGTGTAA GTGCTAAAAA   2160
TGTTGATCCG CAGAAATCTG TAAGTAAAAG AAGTGACGAC ACTGCAAGCG TTACAGGTAT   2220
```

-continued

```
TGCCGAAGCT GGAAAGGAAA ACTTAGGCGC ATCAAATAGT CGACCTTCTG AGTCCACCGT      2280

TGAAGCAAAT AGCCCAGGTG ATGATACTGT GAACAGTGCA TCTATACCTG TAGTGAGTGG      2340

TGAAAACCCA TTGGTAACCC CCTATAATGG TTTGAGGCAT TCGAAAGACA ATAGTGATAG      2400

CGATGGACCT GCGGAATCAA TGGCGAATCC TGATTCAAAT AGTAAAGGTG AGACGGGAAA      2460

GGGGCAAGAT AATGATATGG CGAAGGCTAC TAAAGATAGT AGTAATAGTT CAGATGGTAC      2520

CAGCTCTGCT ACGGGTGATA CTACTGATGC AGTTGATAGG GAAATTAATA AAGGTGTTCC      2580

TGAGGATAGG GATAAAACTG TAGGAAGTAA AGATGGAGGG GGGGAAGATA ACTCTGCAAA      2640

TAAGGATGCA GCGACTGTAG TTGGTGAGGA TAGAATTCGT GAGAACAGCG CTGGTGGTAG      2700

CACTAATGAT AGATCAAAAA ATGACACGGA AAAGAACGGG GCCTCTACCC CTGACAGTAA      2760

ACAAAGTGAG GATGCAACTG CGCTAAGTAA AACCGAAAGT TTAGAATCAA CAGAAAGTGG      2820

AGATAGAACT ACTAATGATA CAACTAACAG TTTAGAAAAT AAAAATGGAG GAAAAGAAAA      2880

GGATTTACAA AAGCATGATT TTAAAAGTAA TGATACGCCG AATGAAGAAC CAAATTCTGA      2940

TCAAACTACA GATGCAGAAG GACATGCAGG GGATAGCATC AAAAATGATA AAGCAGAAAG      3000

GAGAAAGCAT ATGAATAAAG ATACTTTTAC GAAAAATACA AATAGTCACC ATTTAAATAG      3060

TAATAATAAT TTGAGTAATG GAAAATTAGA TATAAAAGAA TACAAATACA GAGATGTCAA      3120

AGCAACAAGG GAAGATATTA TATTAATGTC TTCAGTACGC AAGTGCAACA ATAATATTTC      3180

TTTAGAGTAC TGTAACTCTG TAGAGGACAA AATATCATCG AATACTTGTT CTAGAGAGAA      3240

AAGTAAAAAT TTATGTTGCT CAATATCGGA TTTTTGTTTG AACTATTTTG ACGTGTATTC      3300

TTATGAGTAT CTTAGCTGCA TGAAAAAGGA ATTTGAAGAT CCATCCTACA AGTGCTTTAC      3360

GAAAGGGGGC TTTAAAGGTA TGCAGAAAAA GATGCTGAAT AGAGAAAGGT GTTGAGTAAA      3420

TTAAAAAGGA ATTAATTTTA GGAATGTTAT AAACATTTTT GTACCCAAAA TTCTTTTTGC      3480

AGACAAGACT TACTTTGCCG CGGCGGGAGC GTTGCTGATA CTGCTGTTGT TAATTGCTTC      3540

AAGGAAGATG ATCAAAAATG AGTAACCAGA AAATAAAATA AAATAACATA AAATAAAATA      3600

AAAACTAGAA TAACAATTAA AATAAAATAA AATGAGAAAT GCCTGTTAAT GCACAGTTAA      3660

TTCTAACGAT TCCATTTGTG AAGTTTTAAA GAGAGCACAA ATGCATAGTC ATTATGTCCA      3720

TGCATATATA CACATATATG TACGTATATA TAATAAACGC ACACTTTCTT GTTCGTACAG      3780

TTCTGAAGAA GCTACATTTA ATGAGTTTGA AGAATACTGT GATAATATTC ACAGAATCCC      3840

TCTGATGCCT AACAGTAATT CAAATTTCAA GAGCAAAATT CCATTTAAAA AGAAATGTTA      3900

CATCATTTTG CGTTTTTCTT TTTTTCTTTT TTTTTTCTTT TTTAGATATT GAACACATGC      3960

AGCCATCAAC CCCCCTGGAT TATTCATGAT GCTACTTTGG TAAGTAAAAG CAATTCTGAT      4020

TGTAGTGCTG ATGTAATTTT AGTCATTTTG CTTGCTGCAA TAAACGAGAA AATATATCAA      4080

GCTT                                                                   4084
```

(2) INFORMATION FOR SEQ ID NO:2:

(i) SEQUENCE CHARACTERISTICS:
        (A) LENGTH: 1115 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium vivax (xi) SEQUENCE DESCRIPTION: SEQ ID NO:2:

```
Met Lys Gly Lys Asn Arg Ser Leu Phe Val Leu Leu Val Leu Leu Leu
1               5                   10                  15

Leu His Lys Val Ser Tyr Lys Asp Asp Phe Ser Ile Thr Leu Ile Asn
            20                  25                  30

Tyr His Glu Gly Lys Lys Tyr Leu Ile Ile Leu Lys Arg Lys Leu Glu
        35                  40                  45

Lys Ala Asn Asn Arg Asp Val Cys Asn Phe Phe Leu His Phe Ser Gln
    50                  55                  60

Val Asn Asn Val Leu Leu Glu Arg Thr Ile Glu Thr Leu Leu Glu Cys
65                  70                  75                  80

Lys Asn Glu Tyr Val Lys Gly Glu Asn Gly Tyr Lys Leu Ala Lys Gly
                85                  90                  95

His His Cys Val Glu Glu Asp Asn Leu Glu Arg Trp Leu Gln Gly Thr
            100                 105                 110

Asn Glu Arg Arg Ser Glu Glu Asn Ile Lys Tyr Lys Tyr Gly Val Thr
        115                 120                 125

Glu Leu Lys Ile Lys Tyr Ala Gln Met Asn Gly Lys Arg Ser Ser Arg
130                 135                 140

Ile Leu Lys Glu Ser Ile Tyr Gly Ala His Asn Phe Gly Gly Asn Ser
145                 150                 155                 160

Tyr Met Glu Gly Lys Asp Gly Gly Asp Lys Thr Gly Glu Glu Lys Asp
                165                 170                 175

Gly Glu His Lys Thr Asp Ser Lys Thr Asp Asn Gly Lys Gly Ala Asn
            180                 185                 190

Asn Leu Val Met Leu Asp Tyr Glu Thr Ser Ser Asn Gly Gln Pro Ala
        195                 200                 205

Gly Thr Leu Asp Asn Val Leu Glu Phe Val Thr Gly His Glu Gly Asn
210                 215                 220

Ser Arg Lys Asn Ser Ser Asn Gly Gly Asn Pro Tyr Asp Ile Asp His
225                 230                 235                 240

Lys Lys Thr Ile Ser Ser Ala Ile Ile Asn His Ala Phe Leu Gln Asn
                245                 250                 255

Thr Val Met Lys Asn Cys Asn Tyr Lys Arg Lys Arg Arg Glu Arg Asp
            260                 265                 270

Trp Asp Cys Asn Thr Lys Lys Asp Val Cys Ile Pro Asp Arg Arg Tyr
        275                 280                 285

Gln Leu Cys Met Lys Glu Leu Thr Asn Leu Val Asn Asn Thr Asp Thr
290                 295                 300

Asn Phe His Arg Asp Ile Thr Phe Arg Lys Leu Tyr Leu Lys Arg Lys
305                 310                 315                 320

Leu Ile Tyr Asp Ala Ala Val Glu Gly Asp Leu Leu Leu Lys Leu Asn
                325                 330                 335

Asn Tyr Arg Tyr Asn Lys Asp Phe Cys Lys Asp Ile Arg Trp Ser Leu
            340                 345                 350

Gly Asp Phe Gly Asp Ile Ile Met Gly Thr Asp Met Glu Gly Ile Gly
        355                 360                 365

Tyr Ser Lys Val Val Glu Asn Asn Leu Arg Ser Ile Phe Gly Thr Asp
    370                 375                 380

Glu Lys Ala Gln Gln Arg Arg Lys Gln Trp Trp Asn Glu Ser Lys Ala
385                 390                 395                 400

Gln Ile Trp Thr Ala Met Met Tyr Ser Val Lys Lys Arg Leu Lys Gly
                405                 410                 415
```

-continued

```
Asn Phe Ile Trp Ile Cys Lys Leu Asn Val Ala Val Asn Ile Glu Pro
            420                 425                 430

Gln Ile Tyr Arg Trp Ile Arg Glu Trp Gly Arg Asp Tyr Val Ser Glu
            435                 440                 445

Leu Pro Thr Glu Val Gln Lys Leu Lys Glu Lys Cys Asp Gly Lys Ile
450                 455                 460

Asn Tyr Thr Asp Lys Lys Val Cys Lys Val Pro Pro Cys Gln Asn Ala
465                 470                 475                 480

Cys Lys Ser Tyr Asp Gln Trp Ile Thr Arg Lys Lys Asn Gln Trp Asp
            485                 490                 495

Val Leu Ser Asn Lys Phe Ile Ser Val Lys Asn Ala Glu Lys Val Gln
            500                 505                 510

Thr Ala Gly Ile Val Thr Pro Tyr Asp Ile Leu Lys Gln Glu Leu Asp
            515                 520                 525

Glu Phe Asn Glu Val Ala Phe Glu Asn Glu Ile Asn Lys Arg Asp Gly
            530                 535                 540

Ala Tyr Ile Glu Leu Cys Val Cys Ser Val Glu Glu Ala Lys Lys Asn
545                 550                 555                 560

Thr Gln Glu Val Val Thr Asn Val Asp Asn Ala Ala Lys Ser Gln Ala
                565                 570                 575

Thr Asn Ser Asn Pro Ile Ser Gln Pro Val Asp Ser Ser Lys Ala Glu
            580                 585                 590

Lys Val Pro Gly Asp Ser Thr His Gly Asn Val Asn Ser Gly Gln Asp
            595                 600                 605

Ser Ser Thr Thr Gly Lys Ala Val Thr Gly Asp Gly Gln Asn Gly Asn
            610                 615                 620

Gln Thr Pro Ala Glu Ser Asp Val Gln Arg Ser Asp Ile Ala Glu Ser
625                 630                 635                 640

Val Ser Ala Lys Asn Val Asp Pro Gln Lys Ser Val Ser Lys Arg Ser
                645                 650                 655

Asp Asp Thr Ala Ser Val Thr Gly Ile Ala Glu Ala Gly Lys Glu Asn
            660                 665                 670

Leu Gly Ala Ser Asn Ser Arg Pro Ser Glu Ser Thr Val Glu Ala Asn
            675                 680                 685

Ser Pro Gly Asp Asp Thr Val Asn Ser Ala Ser Ile Pro Val Val Ser
            690                 695                 700

Gly Glu Asn Pro Leu Val Thr Pro Tyr Asn Gly Leu Arg His Ser Lys
705                 710                 715                 720

Asp Asn Ser Asp Ser Asp Gly Pro Ala Glu Ser Met Ala Asn Pro Asp
                725                 730                 735

Ser Asn Ser Lys Gly Glu Thr Gly Lys Gly Gln Asp Asn Asp Met Ala
            740                 745                 750

Lys Ala Thr Lys Asp Ser Ser Asn Ser Ser Asp Gly Thr Ser Ser Ala
            755                 760                 765

Thr Gly Asp Thr Thr Asp Ala Val Asp Arg Glu Ile Asn Lys Gly Val
770                 775                 780

Pro Glu Asp Arg Asp Lys Thr Val Gly Ser Lys Asp Gly Gly Glu
785                 790                 795                 800

Asp Asn Ser Ala Asn Lys Asp Ala Ala Thr Val Val Gly Glu Asp Arg
                805                 810                 815

Ile Arg Glu Asn Ser Ala Gly Gly Ser Thr Asn Asp Arg Ser Lys Asn
            820                 825                 830
```

```
Asp Thr Glu Lys Asn Gly Ala Ser Thr Pro Asp Ser Lys Gln Ser Glu
            835                 840                 845

Asp Ala Thr Ala Leu Ser Lys Thr Glu Ser Leu Glu Ser Thr Glu Ser
            850                 855                 860

Gly Asp Arg Thr Thr Asn Asp Thr Thr Asn Ser Leu Glu Asn Lys Asn
865                 870                 875                 880

Gly Gly Lys Glu Lys Asp Leu Gln Lys His Asp Phe Lys Ser Asn Asp
                    885                 890                 895

Thr Pro Asn Glu Glu Pro Asn Ser Asp Gln Thr Thr Asp Ala Glu Gly
                900                 905                 910

His Asp Arg Asp Ser Ile Lys Asn Asp Lys Ala Glu Arg Arg Lys His
            915                 920                 925

Met Asn Lys Asp Thr Phe Thr Lys Asn Thr Asn Ser His His Leu Asn
            930                 935                 940

Ser Asn Asn Asn Leu Ser Asn Gly Lys Leu Asp Ile Lys Glu Tyr Lys
945                 950                 955                 960

Tyr Arg Asp Val Lys Ala Thr Arg Glu Asp Ile Ile Leu Met Ser Ser
                965                 970                 975

Val Arg Lys Cys Asn Asn Asn Ile Ser Leu Glu Tyr Cys Asn Ser Val
            980                 985                 990

Glu Asp Lys Ile Ser Ser Asn Thr Cys Ser Arg Glu Lys Ser Lys Asn
            995                 1000                1005

Leu Cys Cys Ser Ile Ser Asp Phe Cys Leu Asn Tyr Phe Asp Val Tyr
    1010                1015                1020

Ser Tyr Glu Tyr Leu Ser Cys Met Lys Lys Glu Phe Glu Asp Pro Ser
1025                1030                1035                1040

Tyr Lys Cys Phe Thr Lys Gly Gly Phe Lys Ile Asp Lys Thr Tyr Phe
                1045                1050                1055

Ala Ala Ala Gly Ala Leu Leu Ile Leu Leu Leu Ile Ala Ser Arg Lys
            1060                1065                1070

Met Ile Lys Asn Asp Ser Glu Glu Ala Thr Phe Asn Glu Phe Glu Glu
            1075                1080                1085

Tyr Cys Asp Asn Ile His Arg Ile Pro Leu Met Pro Asn Asn Ile Glu
            1090                1095                1100

His Met Gln Pro Ser Thr Pro Leu Asp Tyr Ser
1105                1110                1115

(2) INFORMATION FOR SEQ ID NO:3:

(i) SEQUENCE CHARACTERISTICS:
        (A) LENGTH: 4507 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:3:

TATATATATA TATATATATA GATAATAACA TATAAATATA TTCAATGTGC ATACAATGAA      60

ATGTAATATT AGTATATATT TTTTTGCTTC CTTCTTTGTG TTATATTTTG CAAAAGCTAG     120

GAATGAATAT GATATAAAAG AGAATGAAAA ATTTTTAGAC GTGTATAAAG AAAAATTTAA     180

TGAATTAGAT AAAAAGAAAT ATGGAAATGT TCAAAAAACT GATAAGAAAA TATTTACTTT     240
```

```
TATAGAAAAT AAATTAGATA TTTTAAATAA TTCAAAATTT AATAAAAGAT GGAAGAGTTA      300

TGGAACTCCA GATAATATAG ATAAAAATAT GTCTTTAATA AATAAACATA ATAATGAAGA      360

AATGTTTAAC AACAATTATC AATCATTTTT ATCGACAAGT TCATTAATAA AGCAAAATAA      420

ATATGTTCCT ATTAACGCTG TACGTGTGTC TAGGATATTA AGTTTCCTGG ATTCTAGAAT      480

TAATAATGGA AGAAATACTT CATCTAATAA CGAAGTTTTA AGTAATTGTA GGGAAAAAAG      540

GAAAGGAATG AAATGGGATT GTAAAAGAA  AAATGATAGA AGCAACTATG TATGTATTCC      600

TGATCGTAGA ATCCAATTAT GCATTGTTAA TCTTAGCATT ATTAAAACAT ATACAAAAGA      660

GACCATGAAG GATCATTTCA TTGAAGCCTC TAAAAAAGAA TCTCAACTTT TGCTTAAAAA      720

AAATGATAAC AAATATAATT CTAAATTTTG TAATGATTTG AAGAATAGTT TTTTAGATTA      780

TGGACATCTT GCTATGGGAA ATGATATGGA TTTTGGAGGT TATTCAACTA AGGCAGAAAA      840

CAAAATTCAA GAAGTTTTTA AAGGGGCTCA TGGGGAAATA AGTGAACATA AAATTAAAAA      900

TTTTAGAAAA GAATGGTGGA ATGAATTTAG AGAGAAACTT TGGGAAGCTA TGTTATCTGA      960

GCATAAAAAT AATATAAATA ATTGTAAAAA TATTCCCCAA GAAGAATTAC AAATTACTCA      1020

ATGGATAAAA GAATGGCATG GAGAATTTTT GCTTGAAAGA GATAATAGAT CAAAATTGCC      1080

AAAAAGTAAA TGTAAAAATA ATACATTATA TGAAGCATGT GAGAAGGAAT GTATTGATCC      1140

ATGTATGAAA TATAGAGATT GGATTATTAG AAGTAAATTT GAATGGCATA CGTTATCGAA      1200

AGAATATGAA ACTCAAAAAG TTCCAAAGGA AAATGCGGAA AATTATTTAA TCAAAATTTC      1260

AGAAAACAAG AATGATGCTA AAGTAAGTTT ATTATTGAAT AATTGTGATG CTGAATATTC      1320

AAAATATTGT GATTGTAAAC ATACTACTAC TCTCGTTAAA AGCGTTTTAA ATGGTAACGA      1380

CAATACAATT AAGGAAAAGC GTGAACATAT TGATTTAGAT GATTTTTCTA AATTTGGATG      1440

TGATAAAAAT TCCGTTGATA CAAACACAAA GGTGTGGGAA TGTAAAAACC CTTATATATT      1500

ATCCACTAAA GATGTATGTG TACCTCCGAG GAGGCAAGAA TTATGTCTTG GAAACATTGA      1560

TAGAATATAC GATAAAAACC TATTAATGAT AAAAGAGCAT ATTCTTGCTA TTGCAATATA      1620

TGAATCAAGA ATATTGAAAC GAAAATATAA GAATAAAGAT GATAAAGAAG TTTGTAAAAT      1680

CATAAATAAA ACTTTCGCTG ATATAAGAGA TATTATAGGA GGTACTGATT ATTGGAATGA      1740

TTTGAGCAAT AGAAAATTAG TAGGAAAAAT TAACACAAAT TCAAAATATG TTCACAGGAA      1800

TAAAAAAAAT GATAAGCTTT TTCGTGATGA GTGGTGGAAA GTTATTAAAA AAGATGTATG      1860

GAATGTGATA TCATGGGTAT TCAAGGATAA AACTGTTTGT AAAGAAGATG ATATTGAAAA      1920

TATACCACAA TTCTTCAGAT GGTTTAGTGA ATGGGGTGAT GATTATTGCC AGGATAAAAC      1980

AAAAATGATA GAGACTCTGA AGGTTGAATG CAAAGAAAAA CCTTGTGAAG ATGACAATTG      2040

TAAAAGTAAA TGTAATTCAT ATAAAGAATG GATATCAAAA AAAAAAGAAG AGTATAATAA      2100

ACAAGCCAAA CAATACCAAG AATATCAAAA AGGAAATAAT TACAAAATGT ATTCTGAATT      2160

TAAATCTATA AAACCAGAAG TTTATTTAAA GAAATACTCG GAAAAATGTT CTAACCTAAA      2220

TTTCGAAGAT GAATTTAAGG AAGAATTACA TTCAGATTAT AAAAATAAAT GTACGATGTG      2280

TCCAGAAGTA AAGGATGTAC CAATTTCTAT AATAAGAAAT AATGAACAAA CTTCGCAAGA      2340

AGCAGTTCCT GAGGAAAACA CTGAAATAGC ACACAGAACG GAAACTCCAT CTATCTCTGA      2400

AGGACCAAAA GGAAATGAAC AAAAAGAACG TGATGACGAT AGTTTGAGTA AAATAAGTGT      2460

ATCACCAGAA AATTCAAGAC CTGAAACTGA TGCTAAAGAT ACTTCTAACT TGTTAAAATT      2520

AAAAGGAGAT GTTGATATTA GTATGCCTAA AGCAGTTATT GGGAGCAGTC CTAATGAAA      2580

TATAAATGTT ACTGAACAAG GGGATAATAT TTCCGGGGTG AATTCTAAAC CTTTATCTGA      2640
```

```
TGATGTACGT CCAGATAAAA AGGAATTAGA AGATCAAAAT AGTGATGAAT CGGAAGAAAC    2700

TGTAGTAAAT CATATATCAA AAAGTCCATC TATAAATAAT GGAGATGATT CAGGCAGTGG    2760

AAGTGCAACA GTGAGTGAAT CTAGTAGTTC AAATACTGGA TTGTCTATTG ATGATGATAG    2820

AAATGGTGAT ACATTTGTTC GAACACAAGA TACAGCAAAT ACTGAAGATG TTATTAGAAA    2880

AGAAAATGCT GACAAGGATG AAGATGAAAA AGGCGCAGAT GAAGAAAGAC ATAGTACTTC    2940

TGAAAGCTTA AGTTCACCTG AAGAAAAAAT GTTAACTGAT AATGAAGGAG AAATAGTTT    3000

AAATCATGAA GAGGTGAAAG AACATACTAG TAATTCTGAT AATGTTCAAC AGTCTGGAGG    3060

AATTGTTAAT ATGAATGTTG AGAAAGAACT AAAAGATACT TTAGAAAATC CTTCTAGTAG    3120

CTTGGATGAA GGAAAAGCAC ATGAAGAATT ATCAGAACCA AATCTAAGCA GTGACCAAGA    3180

TATGTCTAAT ACACCTGGAC CTTTGGATAA CACCAGTGAA GAAACTACAG AAAGAATTAG    3240

TAATAATGAA TATAAAGTTA ACGAGAGGGA AGATGAGAGA ACGCTTACTA AGGAATATGA    3300

AGATATTGTT TTGAAAAGTC ATATGAATAG AGAATCAGAC GATGGTGAAT TATATGACGA    3360

AAATTCAGAC TTATCTACTG TAAATGATGA ATCAGAAGAC GCTGAAGCAA AAATGAAAGG    3420

AAATGATACA TCTGAAATGT CGCATAATAG TAGTCAACAT ATTGAGAGTG ATCAACAGAA    3480

AAACGATATG AAAACTGTTG GTGATTTGGG AACCACACAT GTACAAAACG AAATTAGTGT    3540

TCCTGTTACA GGAGAAATTG ATGAAAAATT AAGGGAAAGT AAAGAATCAA AAATTCATAA    3600

GGCTGAAGAG GAAAGATTAA GTCATACAGA TATACATAAA ATTAATCCTG AAGATAGAAA    3660

TAGTAATACA TTACATTTAA AAGATATAAG AAATGAGGAA AACGAAAGAC ACTTAACTAA    3720

TCAAAACATT AATATTAGTC AAGAAGGGA TTTGCAAAAA CATGGATTCC ATACCATGAA    3780

TAATCTACAT GGAGATGGAG TTTCCGAAAG AAGTCAAATT AATCATAGTC ATCATGGAAA    3840

CAGACAAGAT CGGGGGGGAA ATTCTGGGAA TGTTTTAAAT ATGAGATCTA ATAATAATAA    3900

TTTTAATAAT ATTCCAAGTA GATATAATTT ATATGATAAA AAATTAGATT TAGATCTTTA    3960

TGAAAACAGA AATGATAGTA CAACAAAAGA ATTAATAAAG AAATTAGCAG AAATAAATAA    4020

ATGTGAGAAC GAAATTTCTG TAAAATATTG TGACCATATG ATTCATGAAG AAATCCCATT    4080

AAAAACATGC ACTAAAGAAA AAACAAGAAA TCTGTGTTGT GCAGTATCAG ATTACTGTAT    4140

GAGCTATTTT ACATATGATT CAGAGGAATA TTATAATTGT ACGAAAAGGG AATTTGATGA    4200

TCCATCTTAT ACATGTTTCA GAAAGGAGGC TTTTTCAAGT ATGATATTCA AATTTTTAAT    4260

AACAAATAAA ATATATTATT ATTTTTATAC TTACAAAACT GCAAAAGTAA CAATAAAAAA    4320

AATTAATTTC TCATTAATTT TTTTTTTCTT TTTTTCTTTT TAGGTATGCC ATATTATGCA    4380

GGAGCAGGTG TGTTATTTAT TATATTGGTT ATTTTAGGTG CTTCACAAGC CAAATATCAA    4440

AGGTTAGAAA AAATAAATAA AAATAAAATT GAGAAGAATG TAAATTAAAT ATAGAATTCG    4500

AGCTCGG                                                               4507
```

(2) INFORMATION FOR SEQ ID NO:4:

(i) SEQUENCE CHARACTERISTICS:
        (A) LENGTH: 1435 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:4:

```
Met Lys Cys Asn Ile Ser Ile Tyr Phe Phe Ala Ser Phe Phe Val Leu
 1               5                  10                  15

Tyr Phe Ala Lys Ala Arg Asn Glu Tyr Asp Ile Lys Glu Asn Glu Lys
            20                  25                  30

Phe Leu Asp Val Tyr Lys Glu Lys Phe Asn Glu Leu Asp Lys Lys Lys
        35                  40                  45

Tyr Gly Asn Val Gln Lys Thr Asp Lys Lys Ile Phe Thr Phe Ile Glu
50                  55                  60

Asn Lys Leu Asp Ile Leu Asn Asn Ser Lys Phe Asn Lys Arg Trp Lys
65                  70                  75                  80

Ser Tyr Gly Thr Pro Asp Asn Ile Asp Lys Asn Met Ser Leu Ile Asn
                85                  90                  95

Lys His Asn Asn Glu Glu Met Phe Asn Asn Tyr Gln Ser Phe Leu
            100                 105                 110

Ser Thr Ser Ser Leu Ile Lys Gln Asn Lys Tyr Val Pro Ile Asn Ala
        115                 120                 125

Val Arg Val Ser Arg Ile Leu Ser Phe Leu Asp Ser Arg Ile Asn Asn
    130                 135                 140

Gly Arg Asn Thr Ser Ser Asn Asn Glu Val Leu Ser Asn Cys Arg Glu
145                 150                 155                 160

Lys Arg Lys Gly Met Lys Trp Asp Cys Lys Lys Asn Asp Arg Ser
                165                 170                 175

Asn Tyr Val Cys Ile Pro Asp Arg Arg Ile Gln Leu Cys Ile Val Asn
            180                 185                 190

Leu Ser Ile Ile Lys Thr Tyr Thr Lys Glu Thr Met Lys Asp His Phe
        195                 200                 205

Ile Glu Ala Ser Lys Lys Glu Ser Gln Leu Leu Leu Lys Lys Asn Asp
210                 215                 220

Asn Lys Tyr Asn Ser Lys Phe Cys Asn Asp Leu Lys Asn Ser Phe Leu
225                 230                 235                 240

Asp Tyr Gly His Leu Ala Met Gly Asn Asp Met Asp Phe Gly Gly Tyr
                245                 250                 255

Ser Thr Lys Ala Glu Asn Lys Ile Gln Glu Val Phe Lys Gly Ala His
            260                 265                 270

Gly Glu Ile Ser Glu His Lys Ile Lys Asn Phe Arg Lys Glu Trp Trp
        275                 280                 285

Asn Glu Phe Arg Glu Lys Leu Trp Glu Ala Met Leu Ser Glu His Lys
    290                 295                 300

Asn Asn Ile Asn Asn Cys Lys Asn Ile Pro Gln Glu Glu Leu Gln Ile
305                 310                 315                 320

Thr Gln Trp Ile Lys Glu Trp His Gly Glu Phe Leu Leu Glu Arg Asp
                325                 330                 335

Asn Arg Ser Lys Leu Pro Lys Ser Lys Cys Lys Asn Asn Thr Leu Tyr
            340                 345                 350

Glu Ala Cys Glu Lys Glu Cys Ile Asp Pro Cys Met Lys Tyr Arg Asp
        355                 360                 365

Trp Ile Ile Arg Ser Lys Phe Glu Trp His Thr Leu Ser Lys Glu Tyr
        370                 375                 380

Glu Thr Gln Lys Val Pro Lys Glu Asn Ala Glu Asn Tyr Leu Ile Lys
385                 390                 395                 400

Ile Ser Glu Asn Lys Asn Asp Ala Lys Val Ser Leu Leu Leu Asn Asn
                405                 410                 415
```

```
Cys Asp Ala Glu Tyr Ser Lys Tyr Cys Asp Cys Lys His Thr Thr Thr
            420                 425                 430

Leu Val Lys Ser Val Leu Asn Gly Asn Asp Asn Thr Ile Lys Glu Lys
            435                 440                 445

Arg Glu His Ile Asp Leu Asp Asp Phe Ser Lys Phe Gly Cys Asp Lys
            450                 455                 460

Asn Ser Val Asp Thr Asn Thr Lys Val Trp Glu Cys Lys Asn Pro Tyr
465                 470                 475                 480

Ile Leu Ser Thr Lys Asp Val Cys Val Pro Pro Arg Arg Gln Glu Leu
                485                 490                 495

Cys Leu Gly Asn Ile Asp Arg Ile Tyr Asp Lys Asn Leu Leu Met Ile
                500                 505                 510

Lys Glu His Ile Leu Ala Ile Ala Ile Tyr Glu Ser Arg Ile Leu Lys
            515                 520                 525

Arg Lys Tyr Lys Asn Lys Asp Asp Lys Glu Val Cys Lys Ile Ile Asn
530                 535                 540

Lys Thr Phe Ala Asp Ile Arg Asp Ile Ile Gly Gly Thr Asp Tyr Trp
545                 550                 555                 560

Asn Asp Leu Ser Asn Arg Lys Leu Val Gly Lys Ile Asn Thr Asn Ser
                565                 570                 575

Lys Tyr Val His Arg Asn Lys Lys Asn Asp Lys Leu Phe Arg Asp Glu
            580                 585                 590

Trp Trp Lys Val Ile Lys Lys Asp Val Trp Asn Val Ile Ser Trp Val
            595                 600                 605

Phe Lys Asp Lys Thr Val Cys Lys Glu Asp Asp Ile Glu Asn Ile Pro
610                 615                 620

Gln Phe Phe Arg Trp Phe Ser Glu Trp Gly Asp Asp Tyr Cys Gln Asp
625                 630                 635                 640

Lys Thr Lys Met Ile Glu Thr Leu Lys Val Glu Cys Lys Glu Lys Pro
                645                 650                 655

Cys Glu Asp Asp Asn Cys Lys Ser Lys Cys Asn Ser Tyr Lys Glu Trp
                660                 665                 670

Ile Ser Lys Lys Lys Glu Glu Tyr Asn Lys Gln Ala Lys Gln Tyr Gln
            675                 680                 685

Glu Tyr Gln Lys Gly Asn Asn Tyr Lys Met Tyr Ser Glu Phe Lys Ser
            690                 695                 700

Ile Lys Pro Glu Val Tyr Leu Lys Lys Tyr Ser Glu Lys Cys Ser Asn
705                 710                 715                 720

Leu Asn Phe Glu Asp Glu Phe Lys Glu Glu Leu His Ser Asp Tyr Lys
                725                 730                 735

Asn Lys Cys Thr Met Cys Pro Glu Val Lys Asp Val Pro Ile Ser Ile
            740                 745                 750

Ile Arg Asn Asn Glu Gln Thr Ser Gln Glu Ala Val Pro Glu Glu Asn
            755                 760                 765

Thr Glu Ile Ala His Arg Thr Glu Thr Pro Ser Ile Ser Gly Gly Pro
770                 775                 780

Lys Gly Asn Glu Gln Lys Glu Arg Asp Asp Ser Leu Ser Lys Ile
785                 790                 795                 800

Ser Val Ser Pro Glu Asn Ser Arg Pro Glu Thr Asp Ala Lys Asp Thr
                805                 810                 815

Ser Asn Leu Leu Lys Leu Lys Gly Asp Val Asp Ile Ser Met Pro Lys
            820                 825                 830

Ala Val Ile Gly Ser Ser Pro Asn Asp Asn Ile Asn Val Thr Glu Gln
            835                 840                 845
```

```
Gly Asp Asn Ile Ser Gly Val Asn Ser Lys Pro Leu Ser Asp Val
    850                 855                 860

Arg Pro Asp Lys Lys Glu Leu Glu Asp Gln Asn Ser Asp Glu Ser Glu
865                 870                 875                 880

Glu Thr Val Val Asn His Ile Ser Lys Ser Pro Ser Ile Asn Asn Gly
                885                 890                 895

Asp Asp Ser Gly Ser Gly Ser Ala Thr Val Ser Glu Ser Ser Ser
            900                 905                 910

Asn Thr Gly Leu Ser Ile Asp Asp Arg Asn Gly Asp Thr Phe Val
        915                 920                 925

Arg Thr Gln Asp Thr Ala Asn Thr Glu Asp Val Ile Arg Lys Glu Asn
    930                 935                 940

Ala Asp Lys Asp Glu Asp Lys Gly Ala Asp Glu Arg His Ser
945                 950                 955                 960

Thr Ser Glu Ser Leu Ser Ser Pro Glu Glu Lys Met Leu Thr Asp Asn
                965                 970                 975

Glu Gly Gly Asn Ser Leu Asn His Glu Glu Val Lys Glu His Thr Ser
            980                 985                 990

Asn Ser Asp Asn Val Gln Gln Ser Gly Gly Ile Val Asn Met Asn Val
        995                 1000                1005

Glu Lys Glu Leu Lys Asp Thr Leu Glu Asn Pro Ser Ser Ser Leu Asp
    1010                1015                1020

Glu Gly Lys Ala His Glu Glu Leu Ser Glu Pro Asn Leu Ser Ser Asp
1025                1030                1035                1040

Gln Asp Met Ser Asn Thr Pro Gly Pro Leu Asp Asn Thr Ser Glu Glu
                1045                1050                1055

Thr Thr Glu Arg Ile Ser Asn Asn Glu Tyr Lys Val Asn Glu Arg Glu
            1060                1065                1070

Asp Glu Arg Thr Leu Thr Lys Glu Tyr Glu Asp Ile Val Leu Lys Ser
        1075                1080                1085

His Met Asn Arg Glu Ser Asp Asp Gly Glu Leu Tyr Asp Glu Asn Ser
    1090                1095                1100

Asp Leu Ser Thr Val Asn Asp Glu Ser Glu Asp Ala Glu Ala Lys Met
1105                1110                1115                1120

Lys Gly Asn Asp Thr Ser Glu Met Ser His Asn Ser Ser Gln His Ile
                1125                1130                1135

Glu Ser Asp Gln Gln Lys Asn Asp Met Lys Thr Val Gly Asp Leu Gly
            1140                1145                1150

Thr Thr His Val Gln Asn Glu Ile Ser Val Pro Val Thr Gly Glu Ile
        1155                1160                1165

Asp Glu Lys Leu Arg Glu Ser Lys Glu Ser Lys Ile His Lys Ala Glu
    1170                1175                1180

Glu Glu Arg Leu Ser His Thr Asp Ile His Lys Ile Asn Pro Glu Asp
1185                1190                1195                1200

Arg Asn Ser Asn Thr Leu His Leu Lys Asp Ile Arg Asn Glu Glu Asn
                1205                1210                1215

Glu Arg His Leu Thr Asn Gln Asn Ile Asn Ile Ser Gln Glu Arg Asp
            1220                1225                1230

Leu Gln Lys His Gly Phe His Thr Met Asn Asn Leu His Gly Asp Gly
        1235                1240                1245

Val Ser Glu Arg Ser Gln Ile Asn His Ser His His Gly Asn Arg Gln
    1250                1255                1260
```

```
Asp Arg Gly Gly Asn Ser Gly Asn Val Leu Asn Met Arg Ser Asn Asn
1265                1270                1275                1280

Asn Asn Phe Asn Asn Ile Pro Ser Arg Tyr Asn Leu Tyr Asp Lys Lys
            1285                1290                1295

Leu Asp Leu Asp Leu Tyr Glu Asn Arg Asn Asp Ser Thr Thr Lys Glu
                1300                1305                1310

Leu Ile Lys Lys Leu Ala Glu Ile Asn Lys Cys Glu Asn Glu Ile Ser
        1315                1320                1325

Val Lys Tyr Cys Asp His Met Ile His Glu Glu Ile Pro Leu Lys Thr
    1330                1335                1340

Cys Thr Lys Glu Lys Thr Arg Asn Leu Cys Cys Ala Val Ser Asp Tyr
1345                1350                1355                1360

Cys Met Ser Tyr Phe Thr Tyr Asp Ser Glu Glu Tyr Tyr Asn Cys Thr
            1365                1370                1375

Lys Arg Glu Phe Asp Asp Pro Ser Tyr Thr Cys Phe Arg Lys Glu Ala
                1380                1385                1390

Phe Ser Ser Met Ile Phe Lys Phe Leu Ile Thr Asn Lys Ile Tyr Tyr
        1395                1400                1405

Tyr Phe Tyr Thr Tyr Lys Thr Ala Lys Val Thr Ile Lys Lys Ile Asn
    1410                1415                1420

Phe Ser Leu Ile Phe Phe Phe Phe Ser Phe
1425                1430                1435

(2) INFORMATION FOR SEQ ID NO:5:

(i) SEQUENCE CHARACTERISTICS:
        (A) LENGTH: 2288 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:5:

CACTTTATGC TTCCGGCTCG TATGTTGTGT GGAATTGTGA GCGGATAACA ATTTCACACA      60

GGAAACAGCT ATGACCATGA TTACGCCAAG CTCTAATACG ACTCACTATA GGGAAAGCTG     120

GTACGCCTGC AGGTCCGGTC CGGAATTCAA TAAAATATTT CCAGAAAGGA ATGTGCAAAT     180

TCACATATCC AATATATTCA AGGAATATAA AGAAATAAT GTAGATATCA TATTTGGAAC      240

GTTGAATTAT GAATATAATA ATTTCTGTAA AGAAAAACCT GAATTAGTAT CTGCTGCCAA     300

GTATAATCTG AAAGCTCCAA ATGCTAAATC CCCTAGAATA TACAAATCTA AGGAGCATGA     360

AGAATCAAGT GTGTTTGGTT GCAAAACGAA ATCAGTAAA GTTAAAAAAA ATGGAATTG       420

TTATAGTAAT AATAAAGTAA CTAAACCTGA AGGTGTATGT GGACCACCAA GAAGGCAACA     480

ATTATGTCTT GGATATATAT TTTTGATTCG CGACGGTAAC GAGGAAGGAT TAAAAGATCA    540

TATTAATAAG GCAGCTAATT ATGAGGCAAT GCATTTAAAA GAGAAATATG AGAATGCTGG     600

TGGTGATAAA ATTTGCAATG CTATATTGGG AAGTTATGCA GATATTGGAG ATATTGTAAG     660

AGGTTTGGAT GTTTGGAGGG ATATAAATAC TAATAAATTA TCAGAAAAAT TCCAAAAAAT     720

TTTTATGGGT GGTGGTAATT CTAGGAAAAA ACAAAACGAT AATAATGAAC GTAATAAATG     780

GTGGGAAAAA CAAAGGAATT TAATATGGTC TAGTATGGTA AAACACATTC AAAAGGAAA     840

AACATGTAAA CGTCATAATA ATTTTGAGAA AATTCCTCAA TTTTTGAGAT GGTTAAAAGA     900
```

```
ATGGGGTGAT GAATTTTGTG AGGAAATGGG TACGGAAGTC AAGCAATTAG AGAAAATATG      960

TGAAAATAAA AATTGTTCGG AAAAAAAATG TAAAAATGCA TGTAGTTCCT ATGAAAAATG     1020

GATAAAGGAA CGAAAAAATG AATATAATTT GCAATCAAAG AAATTTGATA GTGATAAAAA     1080

ATTAAATAAA AAAAACAATC TTTATAATAA ATTTGAGGAT CTAAAGCTT ATTTAAGGAG     1140

TGAATCAAAA CAGTGCTCAA ATATAGAATT TAATGATGAA ACATTTACAT TTCCTAATAA     1200

ATATAAAGAG GCTTGTATGG TATGTGAAAA TCCTTCATCT TCGAAAGCTC TTAAACCTAT     1260

AAAAACGAAT GTGTTTCCTA TAGAGGAATC AAAAAAATCT GAGTTATCAA GTTTAACAGA     1320

TAAATCTAAG AATACTCCTA ATAGTTCTGG TGGGGAAAT TATGGAGATA GACAAATATC     1380

AAAAAGAGAC GATGTTCATC ATGATGGTCC TAAGGAAGTG AAATCCGGAG AAAAAGAGGT     1440

ACCAAAAATA GATGCAGCTG TTAAAACAGA AAATGAATTT ACCTCTAATC GAAACGATAT     1500

TGAAGGAAAG GAAAAAAGTA AAGGTGATCA TTCTTCTCCT GTTCATTCTA AAGATATAAA     1560

AAATGAGGAA CCACAAAGGG TGGTGTCTGA AAATTTACCT AAAATTGAAG AGAAAATGGA     1620

ATCTTCTGAT TCTATACCAA TTACTCATAT AGAAGCTGAA AAGGGTCAGT CTTCTAATTC     1680

TAGCGATAAT GATCCTGCAG TAGTAAGTGG TAGAGAATCT AAAGATGTAA ATCTTCATAC     1740

TTCTGAAAGG ATTAAAGAAA ATGAAGAAGG TGTGATTAAA ACAGATGATA GTTCAAAAAG     1800

TATTGAAATT TCTAAAATAC CATCTGACCA AAATAATCAT AGTGATTTAT CACAGAATGC     1860

AAATGAGGAC TCTAATCAAG GAATAAGGA AACAATAAAT CCTCCTTCTA CAGAAAAAAA     1920

TCTCAAAGAA ATTCATTATA AACATCTGA TTCTGATGAT CATGGTTCTA AAATTAAAAG     1980

TGAAATTGAA CCAAAGGAGT TAACGGAGGA ATCACCTCTT ACTGATAAAA AAACTGAAAG     2040

TGCAGCGATT GGTGATAAAA ATCATGAATC AGTAAAAAGC GCTGATATTT TTCAATCTGA     2100

GATTCATAAT TCTGATAATA GAGATAGAAT TGTTTCTGAA AGTGTAGTTC AGGATTCTTC     2160

AGGAAGCTCT ATGAGTACTG AATCTATACG TACTGATAAC AAGGATTTTA AAACAAGTGA     2220

GGATATTGCA CCTTCTATTA ATGGTCGGAA TTCCCGGGTC GACGAGCTCA CTAGTCGGCG     2280

GCCGCTCT                                                              2288

(2) INFORMATION FOR SEQ ID NO:6:

(i) SEQUENCE CHARACTERISTICS:
        (A) LENGTH: 749 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: Plasmodium falciparum (xi) SEQUENCE DESCRIPTION: SEQ ID NO:6:

Ala Asp Asn Asn Phe Thr Gln Glu Thr Ala Met Thr Met Ile Thr Pro
1               5                  10                  15

Ser Ser Asn Thr Thr His Tyr Arg Glu Ser Trp Tyr Ala Cys Arg Ser
            20                  25                  30

Gly Pro Glu Phe Asn Lys Ile Phe Pro Glu Arg Asn Val Gln Ile His
        35                  40                  45

Ile Ser Asn Ile Phe Lys Glu Tyr Lys Glu Asn Asn Val Asp Ile Ile
    50                  55                  60
```

-continued

```
Phe Gly Thr Leu Asn Tyr Glu Tyr Asn Asn Phe Cys Lys Glu Lys Pro
 65                  70                  75                  80

Glu Leu Val Ser Ala Ala Lys Tyr Asn Leu Lys Ala Pro Asn Ala Lys
                 85                  90                  95

Ser Pro Arg Ile Tyr Lys Ser Lys Glu His Glu Glu Ser Ser Val Phe
                100                 105                 110

Gly Cys Lys Thr Lys Ile Ser Lys Val Lys Lys Trp Asn Cys Tyr
                115                 120                 125

Ser Asn Asn Lys Val Thr Lys Pro Glu Gly Val Cys Gly Pro Pro Arg
        130                 135                 140

Arg Gln Gln Leu Cys Leu Gly Tyr Ile Phe Leu Ile Arg Asp Gly Asn
145                 150                 155                 160

Glu Glu Gly Leu Lys Asp His Ile Asn Lys Ala Ala Asn Tyr Glu Ala
                165                 170                 175

Met His Leu Lys Glu Lys Tyr Glu Asn Ala Gly Gly Asp Lys Ile Cys
                180                 185                 190

Asn Ala Ile Leu Gly Ser Tyr Ala Asp Ile Gly Asp Ile Val Arg Gly
        195                 200                 205

Leu Asp Val Trp Arg Asp Ile Asn Thr Asn Lys Leu Ser Glu Lys Phe
        210                 215                 220

Gln Lys Ile Phe Met Gly Gly Asn Ser Arg Lys Lys Gln Asn Asp
225                 230                 235                 240

Asn Asn Glu Arg Asn Lys Trp Trp Glu Lys Gln Arg Asn Leu Ile Trp
                245                 250                 255

Ser Ser Met Val Lys His Ile Pro Lys Gly Lys Thr Cys Lys Arg His
                260                 265                 270

Asn Asn Phe Glu Lys Ile Pro Gln Phe Leu Arg Trp Leu Lys Glu Trp
                275                 280                 285

Gly Asp Glu Phe Cys Glu Glu Met Gly Thr Glu Val Lys Gln Leu Glu
        290                 295                 300

Lys Ile Cys Glu Asn Lys Asn Cys Ser Glu Lys Cys Lys Asn Ala
305                 310                 315                 320

Cys Ser Ser Tyr Glu Lys Trp Ile Lys Glu Arg Lys Asn Glu Tyr Asn
                325                 330                 335

Leu Gln Ser Lys Lys Phe Asp Ser Asp Lys Lys Leu Asn Lys Lys Asn
                340                 345                 350

Asn Leu Tyr Asn Lys Phe Glu Asp Ser Lys Ala Tyr Leu Arg Ser Glu
                355                 360                 365

Ser Lys Gln Cys Ser Asn Ile Glu Phe Asn Asp Glu Thr Phe Thr Phe
        370                 375                 380

Pro Asn Lys Tyr Lys Glu Ala Cys Met Val Cys Glu Asn Pro Ser Ser
385                 390                 395                 400

Ser Lys Ala Leu Lys Pro Ile Lys Thr Asn Val Phe Pro Ile Glu Glu
                405                 410                 415

Ser Lys Lys Ser Glu Leu Ser Ser Leu Thr Asp Lys Ser Lys Asn Thr
                420                 425                 430

Pro Asn Ser Ser Gly Gly Asn Tyr Gly Asp Arg Gln Ile Ser Lys
        435                 440                 445

Arg Asp Asp Val His His Asp Gly Pro Lys Glu Val Lys Ser Gly Glu
        450                 455                 460

Lys Glu Val Pro Lys Ile Asp Ala Ala Val Lys Thr Glu Asn Glu Phe
465                 470                 475                 480

Thr Ser Asn Arg Asn Asp Ile Glu Gly Lys Glu Lys Ser Lys Gly Asp
                485                 490                 495
```

His Ser Ser Pro Val His Ser Lys Asp Ile Lys Asn Glu Glu Pro Gln
            500                 505                 510

Arg Val Val Ser Glu Asn Leu Pro Lys Ile Glu Glu Lys Met Glu Ser
            515                 520                 525

Ser Asp Ser Ile Pro Ile Thr His Ile Glu Ala Glu Lys Gly Gln Ser
            530                 535                 540

Ser Asn Ser Ser Asp Asn Asp Pro Ala Val Val Ser Gly Arg Glu Ser
545                 550                 555                 560

Lys Asp Val Asn Leu His Thr Ser Glu Arg Ile Lys Glu Asn Glu Glu
            565                 570                 575

Gly Val Ile Lys Thr Asp Asp Ser Ser Lys Ser Ile Glu Ile Ser Lys
            580                 585                 590

Ile Pro Ser Asp Gln Asn Asn His Ser Asp Leu Ser Gln Asn Ala Asn
            595                 600                 605

Glu Asp Ser Asn Gln Gly Asn Lys Glu Thr Ile Asn Pro Pro Ser Thr
610                 615                 620

Glu Lys Asn Leu Lys Glu Ile His Tyr Lys Thr Ser Asp Ser Asp Asp
625                 630                 635                 640

His Gly Ser Lys Ile Lys Ser Glu Ile Glu Pro Lys Glu Leu Thr Glu
            645                 650                 655

Glu Ser Pro Leu Thr Asp Lys Lys Thr Glu Ser Ala Ala Ile Gly Asp
            660                 665                 670

Lys Asn His Glu Ser Val Lys Ser Ala Asp Ile Phe Gln Ser Glu Ile
            675                 680                 685

His Asn Ser Asp Asn Arg Asp Arg Ile Val Ser Glu Ser Val Val Gln
            690                 695                 700

Asp Ser Ser Gly Ser Ser Met Ser Thr Glu Ser Ile Arg Thr Asp Asn
705                 710                 715                 720

Lys Asp Phe Lys Thr Ser Glu Asp Ile Ala Pro Ser Ile Asn Gly Arg
            725                 730                 735

Asn Ser Arg Val Asp Glu Leu Thr Ser Arg Arg Pro Leu
            740                 745

(2) INFORMATION FOR SEQ ID NO:7:

(i) SEQUENCE CHARACTERISTICS:
        (A) LENGTH: 2606 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:7:

```
AGCTCTATTA CGACTCACTA TAGGGAAAGC TGGTACGCCT GCAGGTACCG GTCCGGAATT    60

CCCGGGTCGA CGAGCTCACT AGTCGGCGGC CGCTCTAGAG GATCCAAGCT TAATAGTGTT   120

TATACGTCTA TTGGCTTATT TTTAAATAGC TTAAAAAGCG GACCATGTAA AAAGGATAAT   180

GATAATGCAG AGGATAATAT AGATTTTGGT GATGAAGGTA AAACATTTAA AGAGGCAGAT   240

AATTGTAAAC CATGTTCTCA ATTTACTGTT GATTGTAAAA ATTGTAATGG TGGTGATACA   300

AAAGGGAAGT GCAATGGCAG CAATGGCAAA AGAATGGAA ATGATTATAT TACTGCAAGT   360

GATATTGAAA ATGGAGGGAA TTCTATTGGA AATATAGATA TGGTTGTTAG TGATAAGGAT   420
```

```
GCAAATGGAT TTAATGGTTT AGACGCTTGT GGAAGTGCAA ATATCTTTAA AGGTATTAGA      480

AAAGAACAAT GGAAATGTGC TAAAGTATGT GGTTTAGATG TATGTGGTCT TAAAAATGGT      540

AATGGTAGTA TAGATAAAGA TCAAAAACAA ATTATAATTA TTAGAGCATT GCTTAAACGT      600

TGGGTAGAAT ATTTTTTAGA AGATTATAAT AAAATTAATG CCAAAATTTC ACATTGTACG      660

AAAAAGGATA ATGAATCCAC ATGTACAAAT GATTGTCCAA ATAAATGTAC ATGTGTAGAA      720

GAGTGGATAA ATCAGAAAAG GACAGAATGG AAAAATATAA AAAAACATTA CAAACACAA       780

AATGAAAATG GTGACAATAA CATGAAATCT TTGGTTACAA ATATTTTGGG TGCCTTGCAA      840

CCCCAAAGTG ATGTTAACAA AGCTATAAAA CCTTGTAGTG GTTTAACTGC GTTCGAGAGT      900

TTTTGTGGTC TTAATGGCGC TGATAACTCA GAAAAAAAAG AAGGTGAAGA TTACGATCTT      960

GTTCTATGTA TGCTTAAAAA TCTTGAAAAA CAAATTCAGG AGTGCAAAAA GAAACATGGC     1020

GAAACTAGTG TCGAAAATGG TGGCAAATCA TGTACCCCCC TTGACAACAC CACCCTTGAG     1080

GAGGAACCCA TAGAAGAGGA AAACCAAGTG GAAGCGCCGA ACATTTGTCC AAAACAAACA     1140

GTGGAAGATA AAAAAAAGA GGAAGAAGAA GAAACTTGTA CACCGGCATC ACCAGTACCA      1200

GAAAAACCGG TACCTCATGT GGCACGTTGG CGAACATTTA CACCACCTGA GGTATTCAAG     1260

ATATGGAGGG GAAGGAGAAA TAAAACTACG TGCGAAATAG TGGCAGAAAT GCTTAAAGAT     1320

AAGAATGGAA GGACTACAGT AGGTGAATGT TATAGAAAAG AAACTTATTC TGAATGGACG     1380

TGTGATGAAA GTAAGATTAA AATGGGACAG CATGGAGCAT GTATTCCTCC AAGAAGACAA     1440

AAATTATGTT TACATTATTT AGAAAAAATA ATGACAAATA CAAATGAATT GAAATACGCA     1500

TTTATTAAAT GTGCTGCAGC AGAAACTTTT TTGTTATGGC AAAACTACAA AAAAGATAAG     1560

AATGGTAATG CAGAAGATCT CGATGAAAAA TTAAAAGGTG GTATTATCCC CGAAGATTTT     1620

AAACGGCAAA TGTTCTATAC GTTTGCAGAT TATAGAGATA TATGTTTGGG TACGGATATA     1680

TCATCAAAAA AAGATACAAG TAAAGGTGTA GGTAAAGTAA AATGCAATAT TGATGATGTT     1740

TTTTATAAAA TTAGCAATAG TATTCGTTAC CGTAAAAGTT GGTGGGAAAC AAATGGTCCA     1800

GTTATATGGG AAGGAATGTT ATGCGCTTTA AGTTATGATA CGAGCCTAAA TAATGTTAAT     1860

CCGGAAACTC ACAAAAAACT TACCGAAGGC AATAACAACT TGAGAAAGT CATATTTGGT      1920

AGTGATAGTA GCACTACTTT GTCCAAATTT TCTGAAAGAC CTCAATTTCT AAGATGGTTG     1980

ACTGAATGGG GAGAAAATTT CTGCAAAGAA CAAAAAAAGG AGTATAAGGT GTTGTTGGCA     2040

AAATGTAAGG ATTGTGATGT TGATGGTGAT GGTAAATGTA ATGGAAAATG TGTTGCGTGC     2100

AAAGATCAAT GTAAACAATA TCATAGTTGG ATTGGAATAT GGATAGATAA TTATAAAAAA     2160

CAAAAAGGAA GATATACTGA GGTTAAAAAA ATACCTCTGT ATAAAGAAGA TAAAGACGTG     2220

AAAAACTCAG ATGATGCTCG CGATTATTTA AAAACACAAT TACAAATAT GAAATGTGTA      2280

AATGAACTA CTGATGAAAA TTGTGAGTAT AAGTGTATGC ATAAAACCTC ATCCACAAAT      2340

AGTGATATGC CCGAATCGTT GGACGAAAAG CCGGAAAAGG TCAAAGACAA GTGTAATTGT     2400

GTACCTAATG AATGCAATGC ATTGAGTGTA AGTGGTAGCG GTTTTCCTGA TGGTCAAGCT     2460

TACGTACGCG TGCATGCGAC GTCATAGCTC TTCTATAGTG TCACCTAAAT TCAATTCACT     2520

GGCCGTCGTT TTCAACGTC GTGACTGGGA AACCTGGCG TTACCCAACT TAATCGCCTT       2580

GCAGCACATC CCCCTTTCGC CAGCTG                                          2606

(2) INFORMATION FOR SEQ ID NO:8:

(i) SEQUENCE CHARACTERISTICS:
        (A) LENGTH: 921 amino acids
```

(B) TYPE: amino acid
(C) STRANDEDNESS: single
(D) TOPOLOGY: linear (ii) MOLECULE TYPE: protein (iii) HYPOTHETICAL: NO (vi) ORIGINAL SOURCE:
(A) ORGANISM: Plasmodium falciparum (xi) SEQUENCE DESCRIPTION: SEQ ID NO:8:

```
Lys Leu Asn Ser Val Tyr Thr Ser Ile Gly Leu Phe Leu Asn Ser Leu
1               5                  10                  15

Lys Ser Gly Pro Cys Lys Lys Asp Asn Asp Asn Ala Glu Asp Asn Ile
            20                  25                  30

Asp Phe Gly Asp Glu Gly Lys Thr Phe Lys Glu Ala Asp Asn Cys Lys
            35                  40                  45

Pro Cys Ser Gln Phe Thr Val Asp Cys Lys Asn Cys Asn Gly Gly Asp
50                  55                  60

Thr Lys Gly Lys Cys Asn Gly Ser Asn Gly Lys Lys Asn Gly Asn Asp
65                  70                  75                  80

Tyr Ile Thr Ala Ser Asp Ile Glu Asn Gly Asn Ser Ile Gly Asn
                85                  90                  95

Ile Asp Met Val Val Ser Asp Lys Asp Ala Asn Gly Phe Asn Gly Leu
                100                 105                 110

Asp Ala Cys Gly Ser Ala Asn Ile Phe Lys Gly Ile Arg Lys Glu Gln
            115                 120                 125

Trp Lys Cys Ala Lys Val Cys Gly Leu Asp Val Cys Gly Leu Lys Asn
130                 135                 140

Gly Asn Gly Ser Ile Asp Lys Asp Gln Lys Gln Ile Ile Ile Ile Arg
145                 150                 155                 160

Ala Leu Leu Lys Arg Trp Val Glu Tyr Phe Leu Glu Asp Tyr Asn Lys
                165                 170                 175

Ile Asn Ala Lys Ile Ser His Cys Thr Lys Lys Asp Asn Glu Ser Thr
                180                 185                 190

Cys Thr Asn Asp Cys Pro Asn Lys Cys Thr Cys Val Glu Glu Trp Ile
            195                 200                 205

Asn Gln Lys Arg Thr Glu Trp Lys Asn Ile Lys Lys His Tyr Lys Thr
210                 215                 220

Gln Asn Glu Asn Gly Asp Asn Asn Met Lys Ser Leu Val Thr Asp Ile
225                 230                 235                 240

Leu Gly Ala Leu Gln Pro Gln Ser Asp Val Asn Lys Ala Ile Lys Pro
                245                 250                 255

Cys Ser Gly Leu Thr Ala Phe Glu Ser Phe Cys Gly Leu Asn Gly Ala
                260                 265                 270

Asp Asn Ser Glu Lys Lys Glu Gly Asp Tyr Asp Leu Val Leu Cys
            275                 280                 285

Met Leu Lys Asn Leu Glu Lys Gln Ile Gln Glu Cys Lys Lys Lys His
290                 295                 300

Gly Glu Thr Ser Val Glu Asn Gly Gly Lys Ser Cys Thr Pro Leu Asp
305                 310                 315                 320

Asn Thr Thr Leu Glu Glu Glu Pro Ile Glu Glu Asn Gln Val Glu
                325                 330                 335

Ala Pro Asn Ile Cys Pro Lys Gln Thr Val Glu Asp Lys Lys Lys Glu
            340                 345                 350
```

-continued

Glu Glu Glu Glu Thr Cys Thr Pro Ala Ser Pro Val Pro Glu Lys Pro
            355                 360                 365

Val Pro His Val Ala Arg Trp Arg Thr Phe Thr Pro Pro Glu Val Phe
370                 375                 380

Lys Ile Trp Arg Gly Arg Asn Lys Thr Thr Cys Glu Ile Val Ala
385                 390                 395                 400

Glu Met Leu Lys Asp Lys Asn Gly Arg Thr Thr Val Gly Glu Cys Tyr
                405                 410                 415

Arg Lys Glu Thr Tyr Ser Glu Trp Thr Cys Asp Glu Ser Lys Ile Lys
            420                 425                 430

Met Gly Gln His Gly Ala Cys Ile Pro Pro Arg Arg Gln Lys Leu Cys
            435                 440                 445

Leu His Tyr Leu Glu Lys Ile Met Thr Asn Thr Asn Glu Leu Lys Tyr
    450                 455                 460

Ala Phe Ile Lys Cys Ala Ala Ala Glu Thr Phe Leu Leu Trp Gln Asn
465                 470                 475                 480

Tyr Lys Lys Asp Lys Asn Gly Asn Ala Glu Asp Leu Asp Glu Lys Leu
                485                 490                 495

Lys Gly Gly Ile Ile Pro Glu Asp Phe Lys Arg Gln Met Phe Tyr Thr
                500                 505                 510

Phe Ala Asp Tyr Arg Asp Ile Cys Leu Gly Thr Asp Ile Ser Ser Lys
            515                 520                 525

Lys Asp Thr Ser Lys Gly Val Gly Lys Val Lys Cys Asn Ile Asp Asp
530                 535                 540

Val Phe Tyr Lys Ile Ser Asn Ser Ile Arg Tyr Arg Lys Ser Trp Trp
545                 550                 555                 560

Glu Thr Asn Gly Pro Val Ile Trp Glu Gly Met Leu Cys Ala Leu Ser
                565                 570                 575

Tyr Asp Thr Ser Leu Asn Asn Val Asn Pro Glu Thr His Lys Lys Leu
            580                 585                 590

Thr Glu Gly Asn Asn Asn Phe Glu Lys Val Ile Phe Gly Ser Asp Ser
            595                 600                 605

Ser Thr Thr Leu Ser Lys Phe Ser Glu Arg Pro Gln Phe Leu Arg Trp
    610                 615                 620

Leu Thr Glu Trp Gly Glu Asn Phe Cys Lys Glu Gln Lys Lys Glu Tyr
625                 630                 635                 640

Lys Val Leu Leu Ala Lys Cys Lys Asp Cys Asp Val Asp Gly Asp Gly
                645                 650                 655

Lys Cys Asn Gly Lys Cys Val Ala Cys Lys Asp Gln Cys Lys Gln Tyr
                660                 665                 670

His Ser Trp Ile Gly Ile Trp Ile Asp Asn Tyr Lys Lys Gln Lys Gly
            675                 680                 685

Arg Tyr Thr Glu Val Lys Lys Ile Pro Leu Tyr Lys Glu Asp Lys Asp
    690                 695                 700

Val Lys Asn Ser Asp Asp Ala Arg Asp Tyr Leu Lys Thr Gln Leu Gln
705                 710                 715                 720

Asn Met Lys Cys Val Asn Gly Thr Thr Asp Glu Asn Cys Glu Tyr Lys
                725                 730                 735

Cys Met His Lys Thr Ser Ser Thr Asn Ser Asp Met Pro Glu Ser Leu
            740                 745                 750

Asp Glu Lys Pro Glu Lys Val Lys Asp Lys Cys Asn Cys Val Pro Asn
            755                 760                 765

Glu Cys Asn Ala Leu Ser Val Ser Gly Ser Gly Phe Pro Asp Gly Gln
    770                 775                 780

```
Ala Phe Gly Gly Val Leu Glu Gly Thr Cys Lys Gly Leu Gly Glu
785                 790                 795                 800

Pro Lys Lys Lys Ile Glu Pro Pro Gln Tyr Asp Pro Thr Asn Asp Ile
            805                 810                 815

Leu Lys Ser Thr Ile Pro Val Thr Ile Val Leu Ala Leu Gly Ser Ile
            820                 825                 830

Ala Phe Leu Phe Met Lys Val Ile Tyr Ile Tyr Val Trp Tyr Ile Tyr
            835                 840                 845

Met Leu Cys Val Gly Ala Leu Asp Thr Tyr Ile Cys Gly Cys Ile Cys
        850                 855                 860

Ile Cys Ile Phe Ile Cys Val Ser Val Tyr Val Cys Val Tyr Val Tyr
865                 870                 875                 880

Val Phe Leu Tyr Met Cys Val Phe Tyr Ile Tyr Phe Ile Tyr Ile Tyr
            885                 890                 895

Val Phe Ile Leu Lys Met Lys Lys Met Lys Met Lys Lys Met Lys
            900                 905                 910

Lys Met Lys Lys Arg Lys Lys Arg Ile
        915                 920
```

(2) INFORMATION FOR SEQ ID NO:9:

(i) SEQUENCE CHARACTERISTICS:
        (A) LENGTH: 2101 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:9:

```
GGAACAGGGT GATAATAAAG TAGGAGCCTG TGCTCCGTAT AGACGATTAC ATTTATGTGA    60

TTATAATTTG GAATCTATAG ACACAACGTC GACGACGCAT AAGTTGTTGT TAGAGGTGTG   120

TATGGCAGCA AAATACGAAG GAAACTCAAT AAATACACAT TATACACAAC ATCAACGAAC   180

TAATGAGGAT TCTGCTTCCC AATTATGTAC TGTATTAGCA CGAAGTTTTG CAGATATAGG   240

TGATATCGTA AGAGGAAAAG ATCTATATCT CGGTTATGAT AATAAAGAAA AGAACAAAG    300

AAAAAAATTA GAACAGAAAT TGAAAGATAT TTTCAAGAAA ATACATAAGG ACGTGATGAA   360

GACGAATGGC GCACAAGAAC GCTACATAGA TGATGCCAAA GGAGGAGATT TTTTTCAATT   420

AAGAGAAGAT TGGTGGACGT CGAATCGAGA ACAGTATGG AAAGCATTAA TATGTCATGC   480

ACCAAAAGAA GCTAATTATT TTATAAAAAC AGCGTGTAAT GTAGGAAAAG GAACTAATGG   540

TCAATGCCAT TGCATTGGTG GAGATGTTCC CACATATTTC GATTATGTGC CGCAGTATCT   600

TCGCTGGTTC GAGGAATGGG CAGAAGACTT TGCAGGAAA AAAAAAAAAA AACTAGAAAA   660

TTTGCAAAAA CAGTGTCGTG ATTACGAACA AAATTTATAT TGTAGTGGTA ATGGCTACGA   720

TTGCACAAAA ACTATATATA AAAAAGGTAA ACTTGTTATA GGTGAACATT GTACAAACTG   780

TTCTGTTTGG TGTCGTATGT ATGAAACTTG GATAGATAAC CAGAAAAAAG AATTTCTAAA   840

ACAAAAAAGA AAATACGAAA CAGAAATATC AGGTGGTGGT AGTGGTAAGA GTCCTAAAAG   900

GACAAAACGG GCTGCACGTA GTAGTAGTAG TAGTGATGAT AATGGGTATG AAAGTAAATT   960

TTATAAAAAA CTGAAAGAAG TTGGCTACCA AGATGTCGAT AAATTTTTAA AAATATTAAA  1020
```

```
CAAAGAAGGA ATATGTCAAA AACAACCTCA AGTAGGAAAT GAAAAAGCAG ATAATGTTGA      1080

TTTTACTAAT GAAAAATATG TAAAAACATT TTCTCGTACA GAAATTTGTG AACCGTGCCC      1140

ATGGTGTGGA TTGGAAAAAG GTGGTCCACC ATGGAAAGTT AAAGGTGACA AAACCTGCGG      1200

AAGTGCAAAA ACAAAGACAT ACGATCCTAA AAATATTACC GATATACCAG TACTCTACCC      1260

TGATAAATCA CAGCAAAATA TACTAAAAAA ATATAAAAAT TTTTGTGAAA AAGGTGCACC      1320

TGGTGGTGGT CAAATTAAAA AATGGCAATG TTATTATGAT GAACATAGGC CTAGTAGTAA      1380

AAATAATAAT AATTGTGTAG AAGGAACATG GGACAAGTTT ACACAAGGTA ACAAACCGT       1440

TAAGTCCTAT AATGTTTTTT TTTGGGATTG GGTTCATGAT ATGTTACACG ATTCTGTAGA      1500

GTGGAAGACA GAACTTAGTA AGTGTATAAA TAATAACACT AATGGCAACA CATGTAGAAA      1560

CAATAATAAA TGTAAAACAG ATTGTGGTTG TTTTCAAAAA TGGGTTGAAA AAAACAACA       1620

AGAATGGATG GCAATAAAAG ACCATTTTGG AAAGCAAACA GATATTGTCC AACAAAAAGG      1680

TCTTATCGTA TTTAGTCCCT ATGGAGTTCT TGACCTTGTT TTGAAGGGCG GTAATCTGTT      1740

GCAAAATATT AAAGATGTTC ATGGAGATAC AGATGACATA AAACACATTA GAAACTGTT       1800

GGATGAGGAA GACGCAGTAG CAGTTGTTCT TGGTGGCAAG GACAATACCA CAATTGATAA      1860

ATTACTACAA CACGAAAAAG AACAAGCAGA ACAATGCAAA CAAAAGCAGG AAGAATGCGA      1920

GAAAAAAGCA CAACAAGAAA GTCGTGGTCG CTCCGCCGAA ACCCGCGAAG ACGAAAGGAC      1980

ACAACAACCT GCTGATAGTG CCGGCGAAGT CGAAGAAGAA GAAGACGACG ACGACTACGA      2040

CGAAGACGAC GAAGATGACG ACGTAGTCCA GGACGTAGAT GTAAGTGAAA TAAGAGGTCC      2100

G                                                                     2101
```

(2) INFORMATION FOR SEQ ID NO:10:

(i) SEQUENCE CHARACTERISTICS:
        (A) LENGTH: 700 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:10:

```
Glu Gln Gly Asp Asn Lys Val Gly Ala Cys Ala Pro Tyr Arg Arg Leu
1               5                   10                  15

His Leu Cys Asp Tyr Asn Leu Glu Ser Ile Asp Thr Thr Ser Thr Thr
            20                  25                  30

His Lys Leu Leu Leu Glu Val Cys Met Ala Ala Lys Tyr Glu Gly Asn
        35                  40                  45

Ser Ile Asn Thr His Tyr Thr Gln His Gln Arg Thr Asn Glu Asp Ser
    50                  55                  60

Ala Ser Gln Leu Cys Thr Val Leu Ala Arg Ser Phe Ala Asp Ile Gly
65                  70                  75                  80

Asp Ile Val Arg Gly Lys Asp Leu Tyr Leu Gly Tyr Asp Asn Lys Glu
                85                  90                  95

Lys Glu Gln Arg Lys Lys Leu Glu Gln Lys Leu Lys Asp Ile Phe Lys
            100                 105                 110

Lys Ile His Lys Asp Val Met Lys Thr Asn Gly Ala Gln Glu Arg Tyr
        115                 120                 125
```

```
Ile Asp Asp Ala Lys Gly Gly Asp Phe Phe Gln Leu Arg Glu Asp Trp
130                 135                 140

Trp Thr Ser Asn Arg Glu Thr Val Trp Lys Ala Leu Ile Cys His Ala
145                 150                 155                 160

Pro Lys Glu Ala Asn Tyr Phe Ile Lys Thr Ala Cys Asn Val Gly Lys
                165                 170                 175

Gly Thr Asn Gly Gln Cys His Cys Ile Gly Gly Asp Val Pro Thr Tyr
                180                 185                 190

Phe Asp Tyr Val Pro Gln Tyr Leu Arg Trp Phe Glu Glu Trp Ala Glu
            195                 200                 205

Asp Phe Cys Arg Lys Lys Lys Leu Glu Asn Leu Gln Lys Gln
210                 215                 220

Cys Arg Asp Tyr Glu Gln Asn Leu Tyr Cys Ser Gly Asn Gly Tyr Asp
225                 230                 235                 240

Cys Thr Lys Thr Ile Tyr Lys Lys Gly Lys Leu Val Ile Gly Glu His
                245                 250                 255

Cys Thr Asn Cys Ser Val Trp Cys Arg Met Tyr Glu Thr Trp Ile Asp
                260                 265                 270

Asn Gln Lys Lys Glu Phe Leu Lys Gln Lys Arg Lys Tyr Glu Thr Glu
        275                 280                 285

Ile Ser Gly Gly Ser Gly Lys Ser Pro Lys Arg Thr Lys Arg Ala
290                 295                 300

Ala Arg Ser Ser Ser Ser Asp Asp Asn Gly Tyr Glu Ser Lys Phe
305                 310                 315                 320

Tyr Lys Lys Leu Lys Glu Val Gly Tyr Gln Asp Val Asp Lys Phe Leu
                325                 330                 335

Lys Ile Leu Asn Lys Glu Gly Ile Cys Gln Lys Gln Pro Gln Val Gly
                340                 345                 350

Asn Glu Lys Ala Asp Asn Val Asp Phe Thr Asn Glu Lys Tyr Val Lys
        355                 360                 365

Thr Phe Ser Arg Thr Glu Ile Cys Glu Pro Cys Pro Trp Cys Gly Leu
370                 375                 380

Glu Lys Gly Gly Pro Pro Trp Lys Val Lys Gly Asp Lys Thr Cys Gly
385                 390                 395                 400

Ser Ala Lys Thr Lys Thr Tyr Asp Pro Lys Asn Ile Thr Asp Ile Pro
                405                 410                 415

Val Leu Tyr Pro Asp Lys Ser Gln Gln Asn Ile Leu Lys Lys Tyr Lys
            420                 425                 430

Asn Phe Cys Glu Lys Gly Ala Pro Gly Gly Gln Ile Lys Lys Trp
        435                 440                 445

Gln Cys Tyr Tyr Asp Glu His Arg Pro Ser Ser Lys Asn Asn Asn
450                 455                 460

Cys Val Glu Gly Thr Trp Asp Lys Phe Thr Gln Gly Lys Gln Thr Val
465                 470                 475                 480

Lys Ser Tyr Asn Val Phe Phe Trp Asp Trp Val His Asp Met Leu His
            485                 490                 495

Asp Ser Val Glu Trp Lys Thr Glu Leu Ser Lys Cys Ile Asn Asn Asn
            500                 505                 510

Thr Asn Gly Asn Thr Cys Arg Asn Asn Asn Lys Cys Lys Thr Asp Cys
            515                 520                 525

Gly Cys Phe Gln Lys Trp Val Glu Lys Gln Gln Glu Trp Met Ala
        530                 535                 540

Ile Lys Asp His Phe Gly Lys Gln Thr Asp Ile Val Gln Gln Lys Gly
545                 550                 555                 560
```

```
Leu Ile Val Phe Ser Pro Tyr Gly Val Leu Asp Leu Val Leu Lys Gly
            565                 570                 575

Gly Asn Leu Leu Gln Asn Ile Lys Asp Val His Gly Asp Thr Asp Asp
        580                 585                 590

Ile Lys His Ile Lys Lys Leu Leu Asp Glu Glu Asp Ala Val Ala Val
        595                 600                 605

Val Leu Gly Gly Lys Asp Asn Thr Thr Ile Asp Lys Leu Leu Gln His
    610                 615                 620

Glu Lys Glu Gln Ala Glu Gln Cys Lys Gln Lys Gln Glu Cys Glu
625                 630                 635                 640

Lys Lys Ala Gln Gln Glu Ser Arg Gly Arg Ser Ala Glu Thr Arg Glu
                645                 650                 655

Asp Glu Arg Thr Gln Gln Pro Ala Asp Ser Ala Gly Glu Val Glu Glu
            660                 665                 670

Glu Glu Asp Asp Asp Asp Tyr Asp Glu Asp Asp Glu Asp Asp Asp Val
            675                 680                 685

Val Gln Asp Val Asp Val Ser Glu Ile Arg Gly Pro
    690                 695                 700

(2) INFORMATION FOR SEQ ID NO:11:

(i) SEQUENCE CHARACTERISTICS:
        (A) LENGTH: 8220 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Plasmodium falciparum (xi) SEQUENCE DESCRIPTION: SEQ ID NO:11:

AAAAATGGGG CCCAAGGAGG CTGCAGGTGG GGATGATATT GAGGATGAAA GTGCCAAACA     60

TATGTTTGAT AGGATAGGAA AAGATGTGTA CGATAAAGTA AAAGAGGAAG CTAAAGAACG    120

TGGTAAAGGC TTGCAAGGAC GTTTGTCAGA AGCAAAATTT GAGAAAAATG AAAGCGATCC    180

ACAAACACCA GAAGATCCAT GCGATCTTGA TCATAAATAT CATACAAATG TAACTACTAA    240

TGTAATTAAT CCGTGCGCTG ATAGATCTGA CGTGCGTTTT TCCGATGAAT ATGGAGGTCA    300

ATGTACACAT AATAGAATAA AAGATAGTCA ACAGGGTGAT AATAAAGGTG CATGTGCTCC    360

ATATAGGCGA TTGCATGTAT GCGATCAAAA TTTAGAACAG ATAGAGCCTA TAAAAATAAC    420

AAATACTCAT AATTTATTGG TAGATGTGTG TATGGCAGCA AAATTTGAAG ACAATCAAT    480

AACACAAGAT TATCCAAAAT ATCAAGCAAC ATATGGTGAT TCTCCTTCTC AAATATGTAC    540

TATGCTGGCA CGAAGTTTTG CGGACATAGG GGACATTGTC AGAGGAAGAG ATTTGTATTT    600

AGGTAATCCA CAAGAAATAA AACAAAGACA ACAATTAGAA AATAATTTGA AAACAATTTT    660

CGGGAAAATA TATGAAAAAT TGAATGGCGC AGAAGCACGC TACGGAAATG ATCCGGAATT    720

TTTTAAATTA CGAGAAGATT GGTGGACTGC TAATCGAGAA ACAGTATGGA AAGCCATCAC    780

ATGTAACGCT TGGGGTAATA CATATTTTCA TGCAACGTGC AATAGAGGAG AACGAACTAA    840

AGGTTACTGC CGGTGTAACG ACGACCAAGT TCCCACATAT TTTGATTATG TGCCGCAGTA    900

TCTTCGCTGG TTCGAGGAAT GGGCAGAAGA TTTTTGTAGG AAAAAAAATA AAAAAATAAA    960

AGATGTTAAA AGAAATTGTC GTGGAAAAGA TAAAGAGGAT AAGGATCGAT ATTGTAGCCG   1020
```

```
TAATGGCTAC GATTGCGAAA AAACTAAACG AGCGATTGGT AAGTTGCGTT ATGGTAAGCA    1080

ATGCATTAGC TGTTTGTATG CATGTAATCC TTACGTTGAT TGGATAAATA ACCAAAAAGA    1140

ACAATTTGAC AAACAGAAAA AAAAATATGA TGAAGAAATA AAAAAATATG AAAATGGAGC    1200

ATCAGGTGGT AGTAGGCAAA AACGGGATGC AGGTGGTACA ACTACTACTA ATTATGATGG    1260

ATATGAAAAA AAATTTTATG ACGAACTTAA TAAAAGTGAA TATAGAACCG TTGATAAATT    1320

TTTGGAAAAA TTAAGTAATG AAGAAATATG CACAAAAGTT AAAGACGAAG AAGGAGGAAC    1380

AATTGATTTT AAAAACGTTA ATAGTGATAG TACTAGTGGT GCTAGTGGCA CTAATGTTGA    1440

AAGTCAAGGA ACATTTTATC GTTCAAAATA TTGCCAACCC TGCCCTTATT GTGGAGTGAA    1500

AAAGGTAAAT AATGGTGGTA GTAGTAATGA ATGGGAAGAG AAAAATAATG GCAAGTGCAA    1560

GAGTGGAAAA CTTTATGAGC CTAAACCCGA CAAAGAAGGT ACTACTATTA CAATCCTTAA    1620

AAGTGGTAAA GGACATGATG ATATTGAAGA AAAATTAAAC AAATTTTGTG ATGAAAAAAA    1680

TGGTGATACA ATAAATAGTG GTGGTAGTGG TACGGGTGGT AGTGGTGGTG GTAACAGTGG    1740

TAGACAGGAA TTGTATGAAG AATGGAAATG TTATAAAGGT GAAGATGTAG TGAAAGTTGG    1800

ACACGATGAG GATGACGAGG AGGATTATGA AAATGTAAAA AATGCAGGCG GATTATGTAT    1860

ATTAAAAAAC CAAAAAAAGA ATAAAGAAGA AGGTGGAAAT ACGTCTGAAA AGGAGCCTGA    1920

TGAAATCCAA AAGACATTCA ATCCTTTTTT TTACTATTGG GTTGCACATA TGTTAAAAGA    1980

TTCCATACAT TGGAAAAAAA AACTTCAGAG ATGTTTACAA AATGGTAACA GAATAAAATG    2040

TGGAAACAAT AAATGTAATA ATGATTGTGA ATGTTTTAAA AGATGGATTA CACAAAAAAA    2100

AGACGAATGG GGGAAAATAG TACAACATTT TAAAACGCAA AATATTAAAG GTAGAGGAGG    2160

TAGTGACAAT ACGGCAGAAT TAATCCCATT TGATCACGAT TATGTTCTTC AATACAATTT    2220

GCAAGAAGAA TTTTTGAAAG GCGATTCCGA AGACGCTTCC GAAGAAAAAT CCGAAAATAG    2280

TCTGGATGCA GAGGAGGCAG AGGAACTAAA ACACCTTCGC GAAATCATTG AAAGTGAAGA    2340

CAATAATCAA GAAGCATCTG TTGGTGGTGG CGTCACTGAA CAAAAAAATA TAATGGATAA    2400

ATTGCTCAAC TACGAAAAAG ACGAAGCCGA TTTATGCCTA GAAATTCACG AAGATGAGGA    2460

AGAGGAAAAA GAAAAAGGAG ACGGAAACGA ATGTATCGAA GAGGGCGAAA ATTTTCGTTA    2520

TAATCCATGT AGTGGCGAAA GTGGTAACAA ACGATACCCC GTTCTTGCGA ACAAAGTAGC    2580

GTATCAAATG CATCACAAGG CAAAGACACA ATTGGCTAGT CGTGCTGGTA GAAGTGCGTT    2640

GAGAGGTGAT ATATCCTTAG CGCAATTTAA AAATGGTCGT AACGGAAGTA CATTGAAAGG    2700

ACAAATTTGC AAAATTAACG AAAACTATTC CAATGATAGT CGTGGTAATA GTGGTGGACC    2760

ATGTACAGGC AAAGATGGAG ATCACGGAGG TGTGCGCATG AGAATAGGAA CGGAATGGTC    2820

AAATATTGAA GGAAAAAAAC AAACGTCATA CAAAAACGTC TTTTTACCTC CCCGACGAGA    2880

ACACATGTGT ACATCCAATT TAGAAAATTT AGATGTTGGT AGTGTCACTA AAAATGATAA    2940

GGCTAGCCAC TCATTATTGG GAGATGTTCA GCTCGCAGCA AAAACTGATG CAGCTGAGAT    3000

AATAAAACGC TATAAAGATC AAAATAATAT ACAACTAACT GATCCAATAC AACAAAAAGA    3060

CCAGGAGGCT ATGTGTCGAG CTGTACGTTA TAGTTTTGCC GATTTAGGAG ACATTATTCG    3120

AGGAAGAGAT ATGTGGGATG AGGATAAGAG CTCAACAGAC ATGGAAACAC GTTTGATAAC    3180

CGTATTTAAA AACATTAAAG AAAAACATGA TGGAATCAAA GACAACCCTA AATATACCGG    3240

TGATGAAAGC AAAAAGCCCG CATATAAAAA ATTACGAGCA GATTGGTGGG AAGCAAATAG    3300

ACATCAAGTG TGGAGAGCCA TGAAATGCGC AACAAAAGGC ATCATATGTC CTGGTATGCC    3360

AGTTGACGAT TATATCCCCC AACGTTTACG CTGGATGACT GAATGGGCTG AATGGTATTG    3420
```

-continued

```
TAAAGCGCAA TCACAGGAGT ATGACAAGTT AAAAAAAATC TGTGCAGATT GTATGAGTAA      3480

GGGTGATGGA AAATGTACGC AAGGTGATGT CGATTGTGGA AAGTGCAAAG CAGCATGTGA      3540

TAAATATAAA GAGGAAATAG AAAAATGGAA TGAACAATGG AGAAAAATAT CAGATAAATA      3600

CAATCTATTA TACCTACAAG CAAAAACTAC TTCTACTAAT CCTGGCCGTA CTGTTCTTGG      3660

TGATGACGAT CCCGACTATC AACAAATGGT AGATTTTTTG ACCCCAATAC ACAAAGCAAG      3720

TATTGCCGCA CGTGTTCTTG TTAAACGTGC TGCTGGTAGT CCCACTGAGA TCGCCGCCGC      3780

CGCCCCGATC ACCCCCTACA GTACTGCTGC CGGATATATA CACCAGGAAA TAGGATATGG      3840

GGGGTGCCAG GAACAAACAC AATTTTGTGA AAAAAAACAT GGTGCAACAT CAACTAGTAC      3900

CACGAAAGAA AACAAAGAAT ACACCTTTAA ACAACCTCCG CCGGAGTATG CTACAGCGTG      3960

TGATTGCATA AATAGGTCGC AAACAGAGGA GCCGAAGAAA AAGGAAGAAA ATGTAGAGAG      4020

TGCCTGCAAA ATAGTGGAGA AAATACTTGA GGGTAAGAAT GGAAGGACTA CAGTAGGTGA      4080

ATGTAATCCA AAAGAGAGTT ATCCTGATTG GGATTGCAAA AACAATATTG ACATTAGTCA      4140

TGATGGTGCT TGTATGCCTC CAAGGAGACA AAAACTATGT TTATATTATA TAGCACATGA      4200

GAGTCAAACA GAAAATATAA AAACAGACGA TAATTTGAAA GATGCTTTTA TTAAAACTGC      4260

AGCAGCAGAA ACTTTTCTTT CATGGCAATA TTATAAGAGT AAGAATGATA GTGAAGCTAA      4320

AATATTAGAT AGAGGCCTTA TTCCATCCCA ATTTTTAAGA TCCATGATGT ACACGTTTGG      4380

AGATTATAGA GATATATGTT TGAACACAGA TATATCTAAA AACAAAATG ATGTAGCTAA       4440

GGCAAAAGAT AAAATAGGTA AATTTTTCTC AAAAGATGGC AGCAAATCTC CTAGTGGCTT      4500

ATCACGCCAA GAATGGTGGA AAACAAATGG TCCAGAGATT TGGAAAGGAA TGTTATGTGC      4560

CTTAACAAAA TACGTCACAG ATACCGATAA CAAAAGAAAA ATCAAAAACG ACTACTCATA      4620

CGATAAAGTC AACCAATCCC AAAATGGCAA CCCTTCCCTT GAAGAGTTTG CTGCTAAACC      4680

TCAATTTCTA CGTTGGATGA TCGAATGGGG AGAAGAGTTT TGTGCTGAAC GTCAGAAGAA      4740

GGAAAATATC ATAAAAGATG CATGTAATGA AATAAATTCT ACACAACAGT GTAATGATGC      4800

GAAACATCGT TGTAATCAAG CATGTAGAGC ATATCAAGAA TATGTTGAAA ATAAAAAAAA      4860

AGAATTTTCG GGACAAACAA ATAACTTTGT TCTAAAGGCA AATGTTCAGC CCCAAGATCC      4920

AGAATATAAA GGATATGAAT ATAAAGACGG CGTACAACCG ATACAGGGGA ATGAGTATTT      4980

ACTGCAAAAA TGTGATAATA ATAAATGTTC TTGCATGGAT GGAAATGTAC TTTCCGTCTC      5040

TCCAAAAGAA AAACCTTTTG GAAAATATGC CCATAAATAT CCTGAGAAAT GTGATTGTTA      5100

TCAAGGAAAA CATGTACCTA GCATACCACC TCCCCCCCCA CCTGTACAAC CACAACCGGA      5160

AGCACCAACA GTAACAGTAG ACGTTTGCAG CATAGTAAAA ACACTATTTA AAGACACAAA      5220

CAATTTTTCC GACGCTTGTG GTCTAAAATA CGGCAAAACC GCACCATCCA GTTGGAAATG      5280

TATACCAAGT GACACAAAAA GTGGTGCTGG TGCCACCACC GGCAAAAGTG GTAGTGATAG      5340

TGGTAGTATT TGTATCCCAC CCAGGAGGCG ACGATTATAT GTGGGGAAAC TACAGGAGTG      5400

GGCTACCGCG CTCCCACAAG GTGAGGGCGC CGCGCCGTCC CACTCACGCG CCGACGACTT      5460

GCGCAATGCG TTCATCCAAT CTGCTGCAAT AGAGACTTTT TTCTTATGGG ATAGATATAA      5520

AGAAGAGAAA AAACCACAGG GTGATGGGTC ACAACAAGCA CTATCACAAC TAACCAGTAC      5580

ATACAGTGAT GACGAGGAGG ACCCCCCCGA CAAACTGTTA CAAAATGGTA AGATACCCCC      5640

CGATTTTTTG AGATTAATGT TCTATACATT AGGAGATTAT AGGGATATTT TAGTACACGG      5700

TGGTAACACA AGTGACAGTG GTAACACAAA TGGTAGTAAC AACAACAATA TTGTGCTTGA      5760

AGCGAGTGGT AACAAGGAGG ACATGCAAAA AATACAAGAG AAAATAGAAC AAATTCTCCC      5820
```

```
AAAAAATGGT GGCACACCTC TTGTCCCAAA ATCTAGTGCC CAAACACCTG ATAAATGGTG    5880

GAATGAACAC GCCGAATCTA TCTGGAAAGG TATGATATGT GCATTGACAT ATACAGAAAA    5940

GAACCCTGAC ACCAGTGCAA GAGGCGACGA AAACAAAATA GAAAAGGATG ATGAAGTGTA    6000

CGAGAAATTT TTTGGCAGCA CAGCCGACAA ACATGGCACA GCCTCAACCC CAACCGGCAC    6060

ATACAAAACC CAATACGACT ACGAAAAAGT CAAACTTGAG GATACAAGTG GTGCCAAAAC    6120

CCCCTCAGCC TCTAGTGATA CACCCCTTCT CTCCGATTTC GTGTTACGCC CCCCCTACTT    6180

CCGTTACCTT GAAGAATGGG GTCAAAATTT TTGTAAAAAA AGAAAGCATA AATTGGCACA    6240

AATAAAACAT GAGTGTAAAG TAGAAGAAAA TGGTGGTGGT AGTCGTCGTG GTGGTATAAC    6300

AAGACAATAT AGTGGGGATG GCGAAGCGTG TAATGAGATG CTTCCAAAAA ACGATGGAAC    6360

TGTTCCGGAT TTAGAAAAGC CGAGTTGTGC CAAACCTTGT AGTTCTTATA GAAAATGGAT    6420

AGAAAGCAAG GGAAAAGAGT TTGAGAAACA AGAAAAGGCA TATGAACAAC AAAAAGACAA    6480

ATGTGTAAAT GGAAGTAATA AGCATGATAA TGGATTTTGT GAAACACTAA CAACGTCCTC    6540

TAAAGCTAAA GACTTTTTAA AAACGTTAGG ACCATGTAAA CCTAATAATG TAGAGGGTAA    6600

AACAATTTTT GATGATGATA AAACCTTTAA ACATACAAAA GATTGTGATC CATGTCTTAA    6660

ATTTAGTGTT AATTGTAAAA AAGATGAATG TGATAATTCT AAAGGAACCG ATTGCCGAAA    6720

TAAAAATAGT ATTGATGCAA CAGATATTGA AAATGGAGTG GATTCTACTG TACTAGAAAT    6780

GCGTGTCAGT GCTGATAGTA AAAGTGGATT TAATGGTGAT GGTTTAGAGA ATGCTTGTAG    6840

AGGTGCTGGT ATCTTTGAAG GTATTAGAAA AGATGAATGG AAATGTCGTA ATGTATGTGG    6900

TTATGTTGTA TGTAAACCGG AAAACGTTAA TGGGGAAGCA AAGGGAAAAC ACATTATACA    6960

AATTAGAGCA CTGGTTAAAC GTTGGGTAGA ATATTTTTTT GAAGATTATA ATAAAATAAA    7020

ACATAAAATT TCACATCGCA TAAAAAATGG TGAAATATCT CCATGTATAA AAAATTGTGT    7080

AGAAAAATGG GTAGATCAGA AAAGAAAAGA ATGGAAGGAA ATTACTGAAC GTTTCAAAGA    7140

TCAATATAAA AATGACAATT CAGATGATGA CAATGTGAGA AGTTTTTTGG AGACCTTGAT    7200

ACCTCAAATT ACTGATGCAA ACGCTAAAAA TAAGGTTATA AAATTAAGTA AGTTCGGTAA    7260

TTCTTGTGGA TGTAGTGCCA GTGCGAACGA ACAAAACAAA AATGGTGAAT ACAAGGACGC    7320

TATAGATTGT ATGCTTAAAA AGCTTAAAGA TAAAATTGGC GAGTGCGAAA AGAAACACCA    7380

TCAAACTAGT GATACCGAGT GTTCCGACAC ACCACAACCG CAAACCCTTG AAGACGAAAC    7440

TTTGGATGAT GATATAGAAA CAGAGGAGGC GAAGAAGAAC ATGATGCCGA AAATTTGTGA    7500

AAATGTGTTA AAAACAGCAC AACAAGAGGA TGAAGGCGGT TGTGTCCCAG CAGAAAATAG    7560

TGAAGAACCG GCAGCAACAG ATAGTGGTAA GGAAACCCCC GAACAAACCC CCGTTCTCAA    7620

ACCCGAAGAA GAAGCAGTAC CGGAACCACC ACCTCCACCC CCACAGGAAA AAGCCCCGGC    7680

ACCAATACCC CAACCACAAC CACCAACCCC CCCCACACAA CTCTTGGATA ATCCCCACGT    7740

TCTAACCGCC CTGGTGACCT CCACCCTCGC CTGGAGCGTT GGCATCGGTT TTGCTACATT    7800

CACTTATTTT TATCTAAAGG TAAATGGAAG TATATATATG GGGATGTGGA TGTATGTGGA    7860

TGTATGTGAA TGTATGTGGA TGTATGTGGA TGTATGTGGA TGTGTTTTAT GGATATGTAT    7920

TTGTGATTAT GTTTGGATAT ATATATATAT ATATATATGT TTATGTATAT GTGTTTTTGG    7980

ATATATATAT GTGTATGTAT ATGATTTTCT GTATATGTAT TTGTGGGTTA AGGATATATA    8040

TATATGGATG TACTTGTATG TGTTTTATAT ATATATTTTA TATATATGTA TTTATATTAA    8100

AAAAGAAATA TAAAAACAAA TTTATTAAAA TGAAAAAAAG AAAAATGAAA TATAAAAAAA    8160

AATTTATTAA AATAAAAAAA AAAAAAAAAA AAAAGGAGAA AAATTTTTTA AAAAATAATA    8220
```

(2) INFORMATION FOR SEQ ID NO:12:

(i) SEQUENCE CHARACTERISTICS:
        (A) LENGTH: 2710 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Plasmodium falciparum (xi) SEQUENCE DESCRIPTION: SEQ ID NO:12:

```
Asn Val Met Val Glu Leu Ala Lys Met Gly Pro Lys Glu Ala Ala Gly
1               5                   10                  15

Gly Asp Asp Ile Glu Asp Glu Ser Ala Lys His Met Phe Asp Arg Ile
            20                  25                  30

Gly Lys Asp Val Tyr Asp Lys Val Lys Glu Ala Lys Glu Arg Gly
        35                  40                  45

Lys Gly Leu Gln Gly Arg Leu Ser Glu Ala Lys Phe Glu Lys Asn Glu
    50                  55                  60

Ser Asp Pro Gln Thr Pro Glu Asp Pro Cys Asp Leu Asp His Lys Tyr
65                  70                  75                  80

His Thr Asn Val Thr Thr Asn Val Ile Asn Pro Cys Ala Asp Arg Ser
                85                  90                  95

Asp Val Arg Phe Ser Asp Glu Tyr Gly Gly Gln Cys Thr His Asn Arg
            100                 105                 110

Ile Lys Asp Ser Gln Gln Gly Asp Asn Lys Gly Ala Cys Ala Pro Tyr
        115                 120                 125

Arg Arg Leu His Val Cys Asp Gln Asn Leu Glu Gln Ile Glu Pro Ile
130                 135                 140

Lys Ile Thr Asn Thr His Asn Leu Leu Val Asp Val Cys Met Ala Ala
145                 150                 155                 160

Lys Phe Glu Gly Gln Ser Ile Thr Gln Asp Tyr Pro Lys Tyr Gln Ala
                165                 170                 175

Thr Tyr Gly Asp Ser Pro Ser Gln Ile Cys Thr Met Leu Ala Arg Ser
            180                 185                 190

Phe Ala Asp Ile Gly Asp Ile Val Arg Gly Arg Asp Leu Tyr Leu Gly
        195                 200                 205

Asn Pro Gln Glu Ile Lys Gln Arg Gln Gln Leu Glu Asn Asn Leu Lys
    210                 215                 220

Thr Ile Phe Gly Lys Ile Tyr Glu Lys Leu Asn Gly Ala Glu Ala Arg
225                 230                 235                 240

Tyr Gly Asn Asp Pro Glu Phe Phe Lys Leu Arg Glu Asp Trp Trp Thr
                245                 250                 255

Ala Asn Arg Glu Thr Val Trp Lys Ala Ile Thr Cys Asn Ala Trp Gly
            260                 265                 270

Asn Thr Tyr Phe His Ala Thr Cys Asn Arg Gly Glu Arg Thr Lys Gly
        275                 280                 285

Tyr Cys Arg Cys Asn Asp Asp Gln Val Pro Thr Tyr Phe Asp Tyr Val
    290                 295                 300

Pro Gln Tyr Leu Arg Trp Phe Glu Glu Trp Ala Glu Asp Phe Cys Arg
305                 310                 315                 320

Lys Lys Asn Lys Lys Ile Lys Asp Val Lys Arg Asn Cys Arg Gly Lys
                325                 330                 335
```

```
Asp Lys Glu Asp Lys Asp Arg Tyr Cys Ser Arg Asn Gly Tyr Asp Cys
            340                 345                 350

Glu Lys Thr Lys Arg Ala Ile Gly Lys Leu Arg Tyr Gly Lys Gln Cys
        355                 360                 365

Ile Ser Cys Leu Tyr Ala Cys Asn Pro Tyr Val Asp Trp Ile Asn Asn
        370                 375                 380

Gln Lys Glu Gln Phe Asp Lys Gln Lys Lys Tyr Asp Glu Glu Ile
385                 390                 395                 400

Lys Lys Tyr Glu Asn Gly Ala Ser Gly Gly Ser Arg Gln Lys Arg Asp
                405                 410                 415

Ala Gly Gly Thr Thr Thr Asn Tyr Asp Gly Tyr Glu Lys Lys Phe
                420                 425                 430

Tyr Asp Glu Leu Asn Lys Ser Glu Tyr Arg Thr Val Asp Lys Phe Leu
            435                 440                 445

Glu Lys Leu Ser Asn Glu Glu Ile Cys Thr Lys Val Lys Asp Glu Glu
        450                 455                 460

Gly Gly Thr Ile Asp Phe Lys Asn Val Asn Ser Asp Ser Thr Ser Gly
465                 470                 475                 480

Ala Ser Gly Thr Asn Val Glu Ser Gln Gly Thr Phe Tyr Arg Ser Lys
                485                 490                 495

Tyr Cys Gln Pro Cys Pro Tyr Cys Gly Val Lys Val Asn Asn Gly
            500                 505                 510

Gly Ser Ser Asn Glu Trp Glu Lys Asn Gly Lys Cys Lys Ser
        515                 520                 525

Gly Lys Leu Tyr Glu Pro Lys Pro Asp Lys Glu Gly Thr Thr Ile Thr
        530                 535                 540

Ile Leu Lys Ser Gly Lys Gly His Asp Asp Ile Glu Glu Lys Leu Asn
545                 550                 555                 560

Lys Phe Cys Asp Glu Lys Asn Gly Asp Thr Ile Asn Ser Gly Gly Ser
                565                 570                 575

Gly Thr Gly Gly Ser Gly Gly Asn Ser Gly Arg Gln Glu Leu Tyr
            580                 585                 590

Glu Glu Trp Lys Cys Tyr Lys Gly Glu Asp Val Val Lys Val Gly His
        595                 600                 605

Asp Glu Asp Glu Glu Asp Tyr Glu Asn Val Lys Asn Ala Gly Gly
        610                 615                 620

Leu Cys Ile Leu Lys Asn Gln Lys Lys Asn Lys Glu Glu Gly Gly Asn
625                 630                 635                 640

Thr Ser Glu Lys Glu Pro Asp Glu Ile Gln Lys Thr Phe Asn Pro Phe
                645                 650                 655

Phe Tyr Tyr Trp Val Ala His Met Leu Lys Asp Ser Ile His Trp Lys
                660                 665                 670

Lys Lys Leu Gln Arg Cys Leu Gln Asn Gly Asn Arg Ile Lys Cys Gly
            675                 680                 685

Asn Asn Lys Cys Asn Asn Asp Cys Glu Cys Phe Lys Arg Trp Ile Thr
        690                 695                 700

Gln Lys Lys Asp Glu Trp Gly Lys Ile Val Gln His Phe Lys Thr Gln
705                 710                 715                 720

Asn Ile Lys Gly Arg Gly Gly Ser Asp Asn Thr Ala Glu Leu Ile Pro
                725                 730                 735

Phe Asp His Asp Tyr Val Leu Gln Tyr Asn Leu Gln Glu Glu Phe Leu
                740                 745                 750
```

```
Lys Gly Asp Ser Glu Asp Ala Ser Glu Glu Lys Ser Glu Asn Ser Leu
        755                 760                 765

Asp Ala Glu Glu Ala Glu Leu Lys His Leu Arg Glu Ile Ile Glu
        770                 775                 780

Ser Glu Asp Asn Asn Gln Glu Ala Ser Val Gly Gly Val Thr Glu
785                 790                 795                 800

Gln Lys Asn Ile Met Asp Lys Leu Leu Asn Tyr Glu Lys Asp Glu Ala
                    805                 810                 815

Asp Leu Cys Leu Glu Ile His Glu Asp Glu Glu Glu Lys Glu Lys
                820                 825                 830

Gly Asp Gly Asn Glu Cys Ile Glu Glu Gly Glu Asn Phe Arg Tyr Asn
        835                 840                 845

Pro Cys Ser Gly Glu Ser Gly Asn Lys Arg Tyr Pro Val Leu Ala Asn
        850                 855                 860

Lys Val Ala Tyr Gln Met His His Lys Ala Lys Thr Gln Leu Ala Ser
865                 870                 875                 880

Arg Ala Gly Arg Ser Ala Leu Arg Gly Asp Ile Ser Leu Ala Gln Phe
                885                 890                 895

Lys Asn Gly Arg Asn Gly Ser Thr Leu Lys Gly Gln Ile Cys Lys Ile
                900                 905                 910

Asn Glu Asn Tyr Ser Asn Asp Ser Arg Gly Asn Ser Gly Pro Cys
        915                 920                 925

Thr Gly Lys Asp Gly Asp His Gly Gly Val Arg Met Arg Ile Gly Thr
        930                 935                 940

Glu Trp Ser Asn Ile Glu Gly Lys Lys Gln Thr Ser Tyr Lys Asn Val
945                 950                 955                 960

Phe Leu Pro Pro Arg Arg Glu His Met Cys Thr Ser Asn Leu Glu Asn
                965                 970                 975

Leu Asp Val Gly Ser Val Thr Lys Asn Asp Lys Ala Ser His Ser Leu
            980                 985                 990

Leu Gly Asp Val Gln Leu Ala Ala Lys Thr Asp Ala Ala Glu Ile Ile
        995                 1000                1005

Lys Arg Tyr Lys Asp Gln Asn Asn Ile Gln Leu Thr Asp Pro Ile Gln
        1010                1015                1020

Gln Lys Asp Gln Glu Ala Met Cys Arg Ala Val Arg Tyr Ser Phe Ala
1025                1030                1035                1040

Asp Leu Gly Asp Ile Ile Arg Gly Arg Asp Met Trp Asp Glu Asp Lys
                1045                1050                1055

Ser Ser Thr Asp Met Glu Thr Arg Leu Ile Thr Val Phe Lys Asn Ile
                1060                1065                1070

Lys Glu Lys His Asp Gly Ile Lys Asp Asn Pro Lys Tyr Thr Gly Asp
                1075                1080                1085

Glu Ser Lys Lys Pro Ala Tyr Lys Lys Leu Arg Ala Asp Trp Trp Glu
        1090                1095                1100

Ala Asn Arg His Gln Val Trp Arg Ala Met Lys Cys Ala Thr Lys Gly
1105                1110                1115                1120

Ile Ile Cys Pro Gly Met Pro Val Asp Asp Tyr Ile Pro Gln Arg Leu
                1125                1130                1135

Arg Trp Met Thr Glu Trp Ala Glu Trp Tyr Cys Lys Ala Gln Ser Gln
                1140                1145                1150

Glu Tyr Asp Lys Leu Lys Lys Ile Cys Ala Asp Cys Met Ser Lys Gly
                1155                1160                1165

Asp Gly Lys Cys Thr Gln Gly Asp Val Asp Cys Gly Lys Cys Lys Ala
        1170                1175                1180
```

```
Ala Cys Asp Lys Tyr Lys Glu Glu Ile Glu Lys Trp Asn Glu Gln Trp
1185                1190                1195                1200

Arg Lys Ile Ser Asp Lys Tyr Asn Leu Leu Tyr Leu Gln Ala Lys Thr
            1205                1210                1215

Thr Ser Thr Asn Pro Gly Arg Thr Val Leu Gly Asp Asp Pro Asp
        1220                1225                1230

Tyr Gln Gln Met Val Asp Phe Leu Thr Pro Ile His Lys Ala Ser Ile
        1235                1240                1245

Ala Ala Arg Val Leu Val Lys Arg Ala Ala Gly Ser Pro Thr Glu Ile
1250                1255                1260

Ala Ala Ala Ala Pro Ile Thr Pro Tyr Ser Thr Ala Ala Gly Tyr Ile
1265                1270                1275                1280

His Gln Glu Ile Gly Tyr Gly Gly Cys Gln Glu Gln Thr Gln Phe Cys
            1285                1290                1295

Glu Lys Lys His Gly Ala Thr Ser Thr Ser Thr Thr Lys Glu Asn Lys
            1300                1305                1310

Glu Tyr Thr Phe Lys Gln Pro Pro Glu Tyr Ala Thr Ala Cys Asp
        1315                1320                1325

Cys Ile Asn Arg Ser Gln Thr Glu Glu Pro Lys Lys Glu Glu Asn
        1330                1335                1340

Val Glu Ser Ala Cys Lys Ile Val Glu Lys Ile Leu Glu Gly Lys Asn
1345                1350                1355                1360

Gly Arg Thr Thr Val Gly Glu Cys Asn Pro Lys Glu Ser Tyr Pro Asp
            1365                1370                1375

Trp Asp Cys Lys Asn Asn Ile Asp Ile Ser His Asp Gly Ala Cys Met
            1380                1385                1390

Pro Pro Arg Arg Gln Lys Leu Cys Leu Tyr Tyr Ile Ala His Glu Ser
            1395                1400                1405

Gln Thr Glu Asn Ile Lys Thr Asp Asp Asn Leu Lys Asp Ala Phe Ile
        1410                1415                1420

Lys Thr Ala Ala Glu Thr Phe Leu Ser Trp Gln Tyr Tyr Lys Ser
1425                1430                1435                1440

Lys Asn Asp Ser Glu Ala Lys Ile Leu Asp Arg Gly Leu Ile Pro Ser
            1445                1450                1455

Gln Phe Leu Arg Ser Met Met Tyr Thr Phe Gly Asp Tyr Arg Asp Ile
            1460                1465                1470

Cys Leu Asn Thr Asp Ile Ser Lys Gln Asn Asp Val Ala Lys Ala
        1475                1480                1485

Lys Asp Lys Ile Gly Lys Phe Phe Ser Lys Asp Gly Ser Lys Ser Pro
            1490                1495                1500

Ser Gly Leu Ser Arg Gln Glu Trp Trp Lys Thr Asn Gly Pro Glu Ile
1505                1510                1515                1520

Trp Lys Gly Met Leu Cys Ala Leu Thr Lys Tyr Val Thr Asp Thr Asp
            1525                1530                1535

Asn Lys Arg Lys Ile Lys Asn Asp Tyr Ser Tyr Asp Lys Val Asn Gln
            1540                1545                1550

Ser Gln Asn Gly Asn Pro Ser Leu Glu Glu Phe Ala Ala Lys Pro Gln
        1555                1560                1565

Phe Leu Arg Trp Met Ile Glu Trp Gly Glu Glu Phe Cys Ala Glu Arg
        1570                1575                1580

Gln Lys Lys Glu Asn Ile Ile Lys Asp Ala Cys Asn Glu Ile Asn Ser
1585                1590                1595                1600
```

-continued

```
Thr Gln Gln Cys Asn Asp Ala Lys His Arg Cys Asn Gln Ala Cys Arg
        1605                1610                1615
Ala Tyr Gln Glu Tyr Val Glu Asn Lys Lys Lys Glu Phe Ser Gly Gln
        1620                1625                1630
Thr Asn Asn Phe Val Leu Lys Ala Asn Val Gln Pro Gln Asp Pro Glu
        1635                1640                1645
Tyr Lys Gly Tyr Glu Tyr Lys Asp Gly Val Gln Pro Ile Gln Gly Asn
        1650                1655                1660
Glu Tyr Leu Leu Gln Lys Cys Asp Asn Lys Cys Ser Cys Met Asp
1665            1670                1675                1680
Gly Asn Val Leu Ser Val Ser Pro Lys Glu Lys Pro Phe Gly Lys Tyr
            1685                1690                1695
Ala His Lys Tyr Pro Glu Lys Cys Asp Cys Tyr Gln Gly Lys His Val
        1700                1705                1710
Pro Ser Ile Pro Pro Pro Pro Val Gln Pro Gln Pro Glu Ala
        1715                1720                1725
Pro Thr Val Thr Val Asp Val Cys Ser Ile Val Lys Thr Leu Phe Lys
        1730                1735                1740
Asp Thr Asn Asn Phe Ser Asp Ala Cys Gly Leu Lys Tyr Gly Lys Thr
1745            1750                1755                1760
Ala Pro Ser Ser Trp Lys Cys Ile Pro Ser Asp Thr Lys Ser Gly Ala
            1765                1770                1775
Gly Ala Thr Thr Gly Lys Ser Gly Ser Asp Ser Gly Ser Ile Cys Ile
        1780                1785                1790
Pro Pro Arg Arg Arg Arg Leu Tyr Val Gly Lys Leu Gln Glu Trp Ala
        1795                1800                1805
Thr Ala Leu Pro Gln Gly Glu Gly Ala Ala Pro Ser His Ser Arg Ala
        1810                1815                1820
Asp Asp Leu Arg Asn Ala Phe Ile Gln Ser Ala Ala Ile Glu Thr Phe
1825            1830                1835                1840
Phe Leu Trp Asp Arg Tyr Lys Glu Glu Lys Lys Pro Gln Gly Asp Gly
            1845                1850                1855
Ser Gln Gln Ala Leu Ser Gln Leu Thr Ser Thr Tyr Ser Asp Asp Glu
            1860                1865                1870
Glu Asp Pro Pro Asp Lys Leu Leu Gln Asn Gly Lys Ile Pro Pro Asp
            1875                1880                1885
Phe Leu Arg Leu Met Phe Tyr Thr Leu Gly Asp Tyr Arg Asp Ile Leu
            1890                1895                1900
Val His Gly Gly Asn Thr Ser Asp Ser Gly Asn Thr Asn Gly Ser Asn
1905            1910                1915                1920
Asn Asn Asn Ile Val Leu Glu Ala Ser Gly Asn Lys Glu Asp Met Gln
            1925                1930                1935
Lys Ile Gln Glu Lys Ile Glu Gln Ile Leu Pro Lys Asn Gly Gly Thr
            1940                1945                1950
Pro Leu Val Pro Lys Ser Ser Ala Gln Thr Pro Asp Lys Trp Trp Asn
            1955                1960                1965
Glu His Ala Glu Ser Ile Trp Lys Gly Met Ile Cys Ala Leu Thr Tyr
            1970                1975                1980
Thr Glu Lys Asn Pro Asp Thr Ser Ala Arg Gly Asp Glu Asn Lys Ile
1985            1990                1995                2000
Glu Lys Asp Asp Glu Val Tyr Glu Lys Phe Phe Gly Ser Thr Ala Asp
            2005                2010                2015
Lys His Gly Thr Ala Ser Thr Pro Thr Gly Thr Tyr Lys Thr Gln Tyr
            2020                2025                2030
```

```
Asp Tyr Glu Lys Val Lys Leu Glu Asp Thr Ser Gly Ala Lys Thr Pro
        2035                2040                2045

Ser Ala Ser Ser Asp Thr Pro Leu Leu Ser Asp Phe Val Leu Arg Pro
    2050                2055                2060

Pro Tyr Phe Arg Tyr Leu Glu Glu Trp Gly Gln Asn Phe Cys Lys Lys
2065                2070                2075                2080

Arg Lys His Lys Leu Ala Gln Ile Lys His Glu Cys Lys Val Glu Glu
            2085                2090                2095

Asn Gly Gly Gly Ser Arg Arg Gly Gly Ile Thr Arg Gln Tyr Ser Gly
        2100                2105                2110

Asp Gly Glu Ala Cys Asn Glu Met Leu Pro Lys Asn Asp Gly Thr Val
            2115                2120                2125

Pro Asp Leu Glu Lys Pro Ser Cys Ala Lys Pro Cys Ser Ser Tyr Arg
        2130                2135                2140

Lys Trp Ile Glu Ser Lys Gly Lys Glu Phe Glu Lys Gln Glu Lys Ala
2145                2150                2155                2160

Tyr Glu Gln Gln Lys Asp Lys Cys Val Asn Gly Ser Asn Lys His Asp
            2165                2170                2175

Asn Gly Phe Cys Glu Thr Leu Thr Thr Ser Ser Lys Ala Lys Asp Phe
        2180                2185                2190

Leu Lys Thr Leu Gly Pro Cys Lys Pro Asn Asn Val Glu Gly Lys Thr
        2195                2200                2205

Ile Phe Asp Asp Asp Lys Thr Phe Lys His Thr Lys Asp Cys Asp Pro
        2210                2215                2220

Cys Leu Lys Phe Ser Val Asn Cys Lys Lys Asp Glu Cys Asp Asn Ser
2225                2230                2235                2240

Lys Gly Thr Asp Cys Arg Asn Lys Asn Ser Ile Asp Ala Thr Asp Ile
            2245                2250                2255

Glu Asn Gly Val Asp Ser Thr Val Leu Glu Met Arg Val Ser Ala Asp
            2260                2265                2270

Ser Lys Ser Gly Phe Asn Gly Asp Gly Leu Glu Asn Ala Cys Arg Gly
        2275                2280                2285

Ala Gly Ile Phe Glu Gly Ile Arg Lys Asp Glu Trp Lys Cys Arg Asn
    2290                2295                2300

Val Cys Gly Tyr Val Val Cys Lys Pro Glu Asn Val Asn Gly Glu Ala
2305                2310                2315                2320

Lys Gly Lys His Ile Ile Gln Ile Arg Ala Leu Val Lys Arg Trp Val
            2325                2330                2335

Glu Tyr Phe Phe Glu Asp Tyr Asn Lys Ile Lys His Lys Ile Ser His
        2340                2345                2350

Arg Ile Lys Asn Gly Glu Ile Ser Pro Cys Ile Lys Asn Cys Val Glu
        2355                2360                2365

Lys Trp Val Asp Gln Lys Arg Lys Glu Trp Lys Glu Ile Thr Glu Arg
    2370                2375                2380

Phe Lys Asp Gln Tyr Lys Asn Asp Asn Ser Asp Asp Asp Asn Val Arg
2385                2390                2395                2400

Ser Phe Leu Glu Thr Leu Ile Pro Gln Ile Thr Asp Ala Asn Ala Lys
            2405                2410                2415

Asn Lys Val Ile Lys Leu Ser Lys Phe Gly Asn Ser Cys Gly Cys Ser
            2420                2425                2430

Ala Ser Ala Asn Glu Gln Asn Lys Asn Gly Glu Tyr Lys Asp Ala Ile
        2435                2440                2445
```

```
Asp Cys Met Leu Lys Lys Leu Lys Asp Lys Ile Gly Glu Cys Glu Lys
    2450                2455                2460

Lys His His Gln Thr Ser Asp Thr Glu Cys Ser Asp Thr Pro Gln Pro
2465            2470                2475                2480

Gln Thr Leu Glu Asp Glu Thr Leu Asp Asp Ile Glu Thr Glu Glu
                2485                2490                2495

Ala Lys Lys Asn Met Met Pro Lys Ile Cys Glu Asn Val Leu Lys Thr
            2500                2505                2510

Ala Gln Gln Glu Asp Glu Gly Gly Cys Val Pro Ala Glu Asn Ser Glu
            2515                2520                2525

Glu Pro Ala Ala Thr Asp Ser Gly Lys Glu Thr Pro Glu Gln Thr Pro
        2530                2535                2540

Val Leu Lys Pro Glu Glu Glu Ala Val Pro Glu Pro Pro Pro Pro
2545                2550                2555                2560

Pro Gln Glu Lys Ala Pro Ala Pro Ile Pro Gln Pro Gln Pro Pro Thr
                2565                2570                2575

Pro Pro Thr Gln Leu Leu Asp Asn Pro His Val Leu Thr Ala Leu Val
                2580                2585                2590

Thr Ser Thr Leu Ala Trp Ser Val Gly Ile Gly Phe Ala Thr Phe Thr
            2595                2600                2605

Tyr Phe Tyr Leu Lys Val Asn Gly Ser Ile Tyr Met Gly Met Trp Met
    2610                2615                2620

Tyr Val Asp Val Cys Glu Cys Met Trp Met Tyr Val Asp Val Cys Gly
2625                2630                2635                2640

Cys Val Leu Trp Ile Cys Ile Cys Asp Tyr Val Trp Ile Tyr Ile Tyr
                2645                2650                2655

Ile Tyr Ile Cys Leu Cys Ile Cys Val Phe Gly Tyr Ile Tyr Val Tyr
            2660                2665                2670

Val Tyr Asp Phe Leu Tyr Met Tyr Leu Trp Val Lys Asp Ile Tyr Ile
            2675                2680                2685

Trp Met Tyr Leu Tyr Val Phe Tyr Ile Tyr Ile Leu Tyr Ile Cys Ile
    2690                2695                2700

Tyr Ile Lys Lys Glu Ile
2705                2710

(2) INFORMATION FOR SEQ ID NO:13:

(i) SEQUENCE CHARACTERISTICS:
        (A) LENGTH: 19124 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

ACATTTTTTC GTAATATATA TATATATATA TATATATAAT TCTCTTTTTC TAATATATAT      60

ATCCTTCTAT TTTCGATTTT TTCATTTTTT TCCAGTATTA ATTTATTTAT TTATTTGTGA    120

TATTTTATAA TATATTATTT AAATGTGTAT TTATATATGT GTTTTATTTT TGTTATTAAT    180

TTGAATAATC CGAGCGAAAA AAAATATATA ATCTCATATA AAAATTATTT ATAATACAAT    240

ATTATATAGT TTCCTATTAA AATAAATTAA TATAATATAC AATAATATTT CTTGTTATTT    300

TTATAAAATAT AACTAATTTC TTATTTTTAT TTAACTTTAT TCCTTTTTAA TTTCTTAATT    360
```

```
CTTTTATGCA AACAAAAAAC ATAAAGTAAT TCTACATATC AACAAAAAAA AAAAAAAAAA      420

AAAAAAAAAA ATTTATTATA ATATAATAAA AAATATAAAG ACATACGTTC ACTTATTATT      480

ATAAATGATT TATTACGATT AAAACATATT GAGATTATAA TAATATAATT TAACATAGAA      540

AGAGTTAAGA ATACATTTTT TTTTTTTTTT TGATATGTAA TTCAACATAT ATATATATAT      600

ATATCTTTTT AATTTAATTA AATAAAATTC CTTATTATTC ATATTGTTTC TTTTATCACA      660

TGTGAAATAT TAAAAATAAT TTTCGATTTT ATCGATATAT TTATGTCGTT TATATACTTA      720

TATAGGTCTT TATAACTATT GATTAATAGA AGGTAATAGC CTAATAATAT AAATACTCGT      780

ATTTATAAAT TCATTTATAT ATTTCAAATA TATTTCGATG GTTTATTTTC AAATACAATT      840

AATTAGATTT CTTAAATATT TCTTCATTTA TTCATTTTTA TAGCATATAC ATGCACATTA      900

TAAATTATTA ATAAAAAATT TTTATTTTAA TATATAATAA CAATTTTCAT ACATTACATT      960

TTTCACACAA CATTTAAGTT GTCATAATGT AACACATTAA ATAATATATT ACTTATATAT     1020

ATATAATTAT TAATTATATA TTAAATAAAA ATGTATTATC GCCTGTATTA TCATAGTATA     1080

TATAATGTTG TATAACGCTT CAAAATATAT ATAATAATAT AATTAAAAAT ATATATATAG     1140

TAATTAATTA TTTTGTTATG TTATGTAATA ATGCAATTAA TATAAGATAA AATTCTATAG     1200

CTATTATTTA AAATATATAT ATATATATAT ATATATATAT ATATTAGTAT ATGTTATCAA     1260

AATATTATAA TATGTAAATT ATTAATAAAA TATATTTGTA TAACATACAA GACTAAAGAA     1320

AACTATACAA TCTGGTATCT AATAGTATAT ATATATAATA TCTTTTTTAT TTAATTGTTC     1380

TCTCTTTTTT TTTTTTTTAA ATAATAATAA ATATTAATAT ATTTTTTTTC ATAATTATAT     1440

GATTTAGTAT TTTAATAATA AATAAATCTT TTAAAAAACT TCAAAACATT TTTGCATAAA     1500

ATAATATTAA TATTAGTAAC CACCTAGATA AATTAGAGAG AAACGTAGAA CATACCAAAA     1560

AAAATTAGAA CAAAAGAAT ATTACAAAAA ATAATAAAAT TAAATTATTT CTTTACTATT     1620

AATTTAAAGT TTTTTTTCAT ATCATATATT ATGATACACA ATGTTGTTG TTAAATGTTT     1680

TATATACATG CAATGATATG TTTCTGTTGG AATATGTATT ATATACTTAT ATGTTCTAAT     1740

AAATGTATTG TACACCTTTA GCAACTATTA CTACACACAT TTTTATATAA TTTATAACAG     1800

GAAAATATGT TATATTATTA CAATATCTTA ATGTGTTTTT GCAAAAATAT AAAAAACAAG     1860

AAAATTACAA TTGTAATTAA TCGTATGACA TAAAATTATA TTATATTAGA AATTAAAATT     1920

CAAAATTATA AAAAATATGG AAATGTTTTG TTATATTATT TTTTAAAAA TTTAATTATT     1980

TTATTTATT ATTTATTTTT TTTTTTTTTT GTGTTCTAAA TAAAAAGGCA AATATGATTC     2040

AAGTAAAAAA TATATATATT TACATAATGG CAAAATAATT GTTATTATA TTATATGACT     2100

ATAATAAATAT TTTAGATTAA ACATATGTAA TTCATTTAAC AGAATAAAAT AAAATATTAT     2160

ATATATATAT TAATTATTAA GTTATAGATT TAATAAAAAT ATATTATACA TATGAGATTA     2220

AAAATGAAAG TTCACTACAG TAATATATTA TTATATGTCG TCAATTTAAG TATATTCTTA     2280

ATATCACGTA TGCACTAAAT AATGACAATA ATAATATATA TGTAACATTT TATAATTGAT     2340

GTAAATAAAA AAATATACAT ATATACAAAA ACATATATGA TATTTACATT CTTTTTTATA     2400

GATAAATATC CAGAAGAACT ATTACATCAC TTCACTTCAT ATACCAAACA CGAAAAAAAT     2460

ACAACCACTA GGTTATTATG CGAATGTGAC TTATATACGT CCATTTATGA TAATGACCCG     2520

GAAATGATAT TAGTGATGGA AAATTTCAAT AAACAGACAG AAGAAAGGTT TCATGAATAC     2580

AATGAACGCA TGCAAGAAAA ACGAAAAATA TGTAAAGAAC AATGCGAAAA GGATATACAA     2640

AAAATTATTT TAAAAGATAA AATCGAAAAG GAATTAACAG AAAAGTTAGA GGCATTGGAA     2700

ACGAATATAA AGACTGAGGA TATACCTACT TGTGTATGCG AAAAATCAGT AGCAGATAAA     2760
```

```
GTGGAAAAAA CGTGTTTGAA ATGTGGAGGT ATATTGGGTG TTGGTGTGAC TCCATCTTTA    2820

GGTTTATTAG GAGAAATAGG TGGACTTGTT ATAAATAATT GGACAAATAC TCCTTTTTAT    2880

AAAGCTTTTC TTACTTTTGC TCAAAAGGAA GGTATAGCTG CCGGTAAAAT TGCTAGTGAT    2940

ACTGCTCGTA TTGATACAGT TATTTAAGGA ATAATATCAA ATTTTGATGT GCACACTATA    3000

AATGGTTCTA CGTTGGGGAA AGTTATTACC GTAGAAGCTC TTAAGGATGA CACTACTCTT    3060

ACTACGGCAC TATATAATGA ATATGTAAGC ATGTGTGTAA ATACGAACCC TGTCGAAGAC    3120

AAATTAATTT GTGCTTTTGG GATGAGAGAC GGTCTAGTTG CAGGGCAATA TGCTTCATCG    3180

CGAGACGTTA TAGGATCAAG TGTAAAAGGA ATTATTAGAA AAGCTGCAAA CGCTGCTTCA    3240

CAAGCTGCTG AGACAGCTGC TAACGAAACT ACTTCCGGAA TGATCGAAGC CGAGTTAAGT    3300

AAAATAACAT CTGCAGGTGC TAATTTACAC AGTGCAATTA CTTACTCAGT AACTGCGATA    3360

TTGGTTATAG TTTTGGTTAT GGTAATTATT TATTTAATAT TACGTTATCG TAGAAAAAAA    3420

AAAATGAAGA AAAAATTGCA ATATATAAAA TTATTAAAGG AATAGATATA CGATGTCGAG    3480

CTATTAGCGG TAATTTAAAG TATTGTGAAT TTTTCATTTA ATATGCTATG ATCATTTGAT    3540

AATTAATTTT TTTTTATAAT ATTATATTTT TTTATACCTT GGATTCTTAC ATTGTTTTAT    3600

TATTATATGA TTATTTAATT ATTATACTTA TATATATATA TATTTTTACA TTAAGATATT    3660

ATATATGTAT CTATCTATCT ATCTATCTAT ATATATATAT ATATATATAT ATTATAATAA    3720

TTATTATTAT TAGATGCATA TTAGTGATGA TTATAATAAT AACCTATTGA AGAGAATAGA    3780

ACATAATAAT ATATTAAATT AATAGAACTT CATTTTTATT GTTATATGTA TATAAAAATA    3840

AGAAATTTGA AAAAGTAATT TACACATGAT AATGTATTTT ATTTTATTTG TGTTGTTTTA    3900

TATTTATTTA TAAAAATTGT TTAATATAAG TTGTTATTAT AATTTTTTAA TATGGCACCA    3960

TTAGCTTTCC ATTATACAAA TATATATTTC CTCATTAGAA TCTGAATATT TATTGTATTA    4020

TAAAAAAAGT ATAATATAAT AAAATATCTA AGATTTTTTC TAATTTGTTT AATTTATAAT    4080

AAATTTTAAT TTTATACGAT AGAATAAATT ATAATCAACA TATATATATG TATTCATCTT    4140

AAGAACCTAT TACAATATAG TAACAACTGG TTCCTTTTTA TTATAAATAA CATAAGAATG    4200

TGTAAAAGGA TAGTTGTTAA AGGCTTTTTT AATATTGATT ATAAATGTTT GTAAGATATA    4260

TATAATAGAT ATCTTAACAT ACAACTTTGC ATAATTGTAA TTAAAAAAAT ATATATAATA    4320

AGAAATATTA TAAATAATAT TATAAAAAAT TAAGCATAAA TGTCACAATA AATTTTTTTT    4380

TATTAATTTA ATTTTATTTT ATTGTTCTAA AATATATTGA TTATGAGAAT ATTATTGTG     4440

TCTAATATAA TTAAGATATT TCTAATATTA ATTTATATAT ATATATTTAA AAGTATTTTA    4500

AGAATAATTT TTTACTTATT TATTATAATA TGAAATATGC ATGGAGTATA TATAAATATT    4560

GATGACAAAA AAAAAACTTT TAAAATGGAA AATATGCATA TAATAAAATA CTATATAGTA    4620

TAATTGGTGA AATAGTTGTA ACTTATACAA ACATGTTGCA TTCATAATTT AGAGATTATG    4680

TAATATTGTT TATGTATCGT AATATATATT AATATAATTG TTTTTTTAGT ATGTATGGTA    4740

TTCTAATAAT ATATTCATAT GTAGTCATAG TGTCAATGAA TATAAATAT GGTATATTTA     4800

TATTATTGTA TATATTAAAT AAGTAACACA GAACATTATA TATAGTAATA AATAGAAGAA    4860

ATAATATATT TTTATGTTAT ATATTATTAG TTATTATAAA GGGGAAAATT CATAATATTT    4920

ATGAAAATTT TTGTATATGA TATAGTTATA AGTTAAAAAA AAAAAAAAAC AAGAACAAAA    4980

ATGGAAAGCA TAAAAAATGT TACTGTAATA GGATAAAATA TATTATATAA AATGTTTATT    5040

TTATCTTAAA AAGGTTCCTA TTATAACATT AAAAAAAATT TGTCCCATTT TATAAATAAT    5100

TAACTACATT TACATAATGA AATTTCGATT TTGTGTTTTT TTGATGAATA TTATGGACTA    5160
```

| | | | | |
|---|---|---|---|---|
| ATTATTTATA | TGTGAATGCG | TTCTATATAA | TAATAATAAT | TTTATTTAAA AAAATGAAAA 5220 |
| ATAAGAAATA | AATATCCTGA | TTTTGTAGTT | CCAATAGCTT | AATATAATTA TGGACTCATA 5280 |
| TATATATTAT | ATATATCTTT | ACAACAAGTA | ATAAGTAAAT | ATTATTTTAA TCTTAATAAG 5340 |
| GAAAATAAAA | ATAATAAAAT | AAGAATACTG | AATAATAAGT | CATATTATAC ATTTTTTAAA 5400 |
| AATGTAACAT | AATTACAAAT | ACGTAACATG | TATTATAGAA | ATAATAAGAA TTTAATATTA 5460 |
| AGGATAAATA | TAAATATTTA | AAATTATATT | TTTTTATGTC | AATTTATGTT ATATTATATT 5520 |
| ATATTAACAT | GATTAGTTTT | TTGAAAAATA | TTTAAATATC | ATATAATAAT AATAAATTAG 5580 |
| TTAAAATAAT | AGTATTTCAT | ACAAAATACT | AACTTATAAG | TATATCATAT AATATTATAT 5640 |
| ATATATATAT | TTATGTGTTT | TTGATTGGGT | GTATATAAGG | CTATAAGTAT ATATGGGTTG 5700 |
| TTCATTATAT | ATTTATATGT | GAATAGATAC | ATATAAGTTA | ATATATTTAT TTGTGTATAT 5760 |
| GTCTGTGTTA | AGATAGATAT | GCATTACAGT | TAAGGGTTAT | AGTTTTTTTT TTTTTTTTTT 5820 |
| GTACATATAT | ATAAAAAATA | GATAACTAAC | AATATGCATA | TTACAAGAAT AATATTTGTA 5880 |
| TAAAATATAT | ATATATATAT | ATATATAAAG | ACATTAAAAC | TATACTAATA GGTAATTAGT 5940 |
| TTTATTTATAT | CATCCTTTTA | TTATTATAAT | TTTTTTTGTT | TTACTTCTTG TCGTTCTTTT 6000 |
| TTGTTATTAT | AATATAACAA | ATATAAAACA | ATATCAGTAT | TTGGAATATA AATAAATTTA 6060 |
| TTCTACATAT | ATGCATATAT | ATATATATAT | ATATATATAT | ATATATATAT ATATATATAT 6120 |
| ATATGTATGA | TTTTATACTA | TTTTTATACA | TGCATTTTTA | TATATTTTAG TATATACTTT 6180 |
| AAAGATATTA | TTAATATTTA | TATAGTAGCA | TATATGTATT | TATATTATAA CAAATATTTT 6240 |
| CATTTATATA | AATATATAGA | ACATGAACAT | TTTATTAATA | ACTCATATTT GAATATATAT 6300 |
| ATTTATAATG | TGTATTTTTA | CTTATTTTTT | TATATTATAC | AATAAAATTT TGAAATTCAT 6360 |
| AAAATGCATG | AAATACATAA | AAAAATACAA | CAAAACAAAT | GATAAAAACA TTTTTATTAA 6420 |
| TATAATATAA | TATAATATAA | TAATATATTT | TTCCTGTTAT | TTATTTATCA TTTTTTTTTT 6480 |
| GATGCTATAT | ATATTATTAT | ATAATAAATT | ATAATATATA | ACAACAAAAA TTAATAATAA 6540 |
| TAATATACTA | CTTTTAATAT | AATACAACAA | TACAAAGAAT | ATGTATCTAT ATCAATTATA 6600 |
| TATATATGAA | TATATAAATA | TGATAGATAA | TATAGATAGA | GAGAAACGAA GAACATATTT 6660 |
| GTCTCTTTTG | TTATCTCTAA | TATATATATA | TATATAATAA | ATTAAAATAA AGTCAAAAAA 6720 |
| AATATACATA | TATTAATGTT | AATAATTAAA | TATATAAACA | CGTTGCATAT ATACTTTTTT 6780 |
| ATATGTTTGT | ATTTTCGTAT | TTTTTTTTTC | TCATTTATAA | TTTTACTTAA TAAATAAAAC 6840 |
| ATAAAAAAAA | TAATATATAT | ATAATTAAAT | AGATAAATAA | AGGAATACAT AAAATATAAT 6900 |
| ATTTCTGATT | ATATTTTTTT | TTTGTTAGAA | TATTTAAATT | TATTATAAAT TTATTAATAT 6960 |
| ATATATATAT | TTTTTTTAAA | AATATATAAA | ACTAATAATT | ATTATTATAT ACATATTAAA 7020 |
| TATTATTTTT | TTAACATATA | CATATATTGT | AATATTATAA | TAGTACAACT ATTAATATAT 7080 |
| ATATATATAT | ATATACAATA | TTTATATATA | TTGTAATACA | TAAATTATAC CTTACATATA 7140 |
| TATATACATT | CACAAAAGTG | TTATTATTCT | TATTCTACCA | TATTATAATA CTACTGTAAT 7200 |
| ATACATATAT | ACATACCCCC | ACGTACGTAC | GAAACACCAC | CAAACCATGT ATCACGTATG 7260 |
| TATGTATGCC | ACGATATAAA | CCACGTACCA | CGTATGACAT | AATGTAATGG TGGAGTTAGC 7320 |
| AAAAATGGGG | CCCAAGGAGG | CTGCAGGTGG | GGATGATATT | GAGGATGAAA GTGCCAAACA 7380 |
| TATGTTTGAT | AGGATAGGAA | AAGATGTGTA | CGATAAAGTA | AAAGAGGAAG CTAAAGAACG 7440 |
| TGGTAAAGGC | TTGCAAGGAC | GTTTGTCAGA | AGCAAAATTT | GAGAAAAATG AAAGCGATCC 7500 |
| ACAAACACCA | GAAGATCCAT | GCGATCTTGA | TCATAAATAT | CATACAAATG TAACTACTAA 7560 |

```
TGTAATTAAT CCGTGCGCTG ATAGATCTGA CGTGCGTTTT TCCGATGAAT ATGGAGGTCA    7620

ATGTACACAT AATAGAATAA AAGATAGTCA ACAGGGTGAT AATAAAGGTG CATGTGCTCC    7680

ATATAGGCGA TTGCATGTAT GCGATCAAAA TTTAGAACAG ATAGAGCCTA TAAAAATAAC    7740

AAATACTCAT AATTTATTGG TAGATGTGTG TATGGCAGCA AAATTTGAAG GACAATCAAT    7800

AACACAAGAT TATCCAAAAT ATCAAGCAAC ATATGGTGAT TCTCCTTCTC AAATATGTAC    7860

TATGCTGGCA CGAAGTTTTG CGGACATAGG GGACATTGTC AGAGGAAGAG ATTTGTATTT    7920

AGGTAATCCA CAAGAAATAA AACAAAGACA ACAATTAGAA AATAATTTGA AAACAATTTT    7980

CGGGAAAATA TATGAAAAAT TGAATGGCGC AGAAGCACGC TACGGAAATG ATCCGGAATT    8040

TTTTAAATTA CGAGAAGATT GGTGGACTGC TAATCGAGAA ACAGTATGGA AAGCCATCAC    8100

ATGTAACGCT TGGGGTAATA CATATTTTCA TGCAACGTGC AATAGAGGAG AACGAACTAA    8160

AGGTTACTGC CGGTGTAACG ACGACCAAGT TCCCACATAT TTTGATTATG TGCCGCAGTA    8220

TCTTCGCTGG TTCGAGGAAT GGGCAGAAGA TTTTTGTAGG AAAAAAAATA AAAAAATAAA    8280

AGATGTTAAA AGAAATTGTC GTGGAAAAGA TAAAGAGGAT AAGGATCGAT ATTGTAGCCG    8340

TAATGGCTAC GATTGCGAAA AAACTAAACG AGCGATTGGT AAGTTGCGTT ATGGTAAGCA    8400

ATGCATTAGC TGTTTGTATG CATGTAATCC TTACGTTGAT TGGATAAATA ACCAAAAAGA    8460

ACAATTTGAC AAACAGAAAA AAAAATATGA TGAAGAAATA AAAAAATATG AAAATGGAGC    8520

ATCAGGTGGT AGTAGGCAAA AACGGGATGC AGGTGGTACA ACTACTACTA ATTATGATGG    8580

ATATGAAAAA AAATTTTATG ACGAACTTAA TAAAAGTGAA TATAGAACCG TTGATAAATT    8640

TTTGGAAAAA TTAAGTAATG AAGAAATATG CACAAAAGTT AAAGACGAAG AAGGAGGAAC    8700

AATTGATTTT AAAAACGTTA ATAGTGATAG TACTAGTGGT GCTAGTGGCA CTAATGTTGA    8760

AAGTCAAGGA ACATTTTATC GTTCAAAATA TTGCCAACCC TGCCCTTATT GTGGAGTGAA    8820

AAAGGTAAAT AATGGTGGTA GTAGTAATGA ATGGAAGAG AAAAATAATG GCAAGTGCAA    8880

GAGTGGAAAA CTTTATGAGC CTAAACCCGA CAAAGAAGGT ACTACTATTA CAATCCTTAA    8940

AAGTGGTAAA GGACATGATG ATATTGAAGA AAAATTAAAC AAATTTTGTG ATGAAAAAAA    9000

TGGTGATACA ATAAATAGTG GTGGTAGTGG TACGGGTGGT AGTGGTGGTG GTAACAGTGG    9060

TAGACAGGAA TTGTATGAAG AATGGAAATG TTATAAAGGT GAAGATGTAG TGAAAGTTGG    9120

ACACGATGAG GATGACGAGG AGGATTATGA AAATGTAAAA AATGCAGGCG GATTATGTAT    9180

ATTAAAAAAC CAAAAAAAGA ATAAAGAAGA AGGTGGAAAT ACGTCTGAAA AGGAGCCTGA    9240

TGAAATCCAA AAGACATTCA ATCCTTTTTT TTACTATTGG GTTGCACATA TGTTAAAAGA    9300

TTCCATACAT TGGAAAAAAA AACTTCAGAG ATGTTTACAA AATGGTAACA GAATAAAATG    9360

TGGAAACAAT AAATGTAATA ATGATTGTGA ATGTTTTAAA AGATGGATTA CACAAAAAAA    9420

AGACGAATGG GGGAAAATAG TACAACATTT TAAAACGCAA AATATTAAAG GTAGAGGAGG    9480

TAGTGACAAT ACGGCAGAAT TAATCCCATT TGATCACGAT TATGTTCTTC AATACAATTT    9540

GCAAGAAGAA TTTTTGAAAG GCGATTCCGA AGACGCTTCC GAAGAAAAAT CCGAAAATAG    9600

TCTGGATGCA GAGGAGGCAG AGGAACTAAA ACACCTTCGC GAAATCATTG AAAGTGAAGA    9660

CAATAATCAA GAAGCATCTG TTGGTGGTGG CGTCACTGAA CAAAAAAATA TAATGGATAA    9720

ATTGCTCAAC TACGAAAAAG ACGAAGCCGA TTTATGCCTA GAAATTCACG AAGATGAGGA    9780

AGAGGAAAAA GAAAAAGGAG ACGGAAACGA ATGTATCGAA GAGGGCGAAA ATTTTCGTTA    9840

TAATCCATGT AGTGGCGAAA GTGGTAACAA ACGATACCCC GTTCTTGCGA ACAAAGTAGC    9900

GTATCAAATG CATCACAAGG CAAAGACACA ATTGGCTAGT CGTGCTGGTA GAAGTGCGTT    9960
```

```
GAGAGGTGAT ATATCCTTAG CGCAATTTAA AAATGGTCGT AACGGAAGTA CATTGAAAGG   10020

ACAAATTTGC AAAATTAACG AAAACTATTC CAATGATAGT CGTGGTAATA GTGGTGGACC   10080

ATGTACAGGC AAAGATGGAG ATCACGGAGG TGTGCGCATG AGAATAGGAA CGGAATGGTC   10140

AAATATTGAA GGAAAAAAAC AAACGTCATA CAAAAACGTC TTTTTACCTC CCCGACGAGA   10200

ACACATGTGT ACATCCAATT TAGAAAATTT AGATGTTGGT AGTGTCACTA AAAATGATAA   10260

GGCTAGCCAC TCATTATTGG GAGATGTTCA GCTCGCAGCA AAAACTGATG CAGCTGAGAT   10320

AATAAAACGC TATAAAGATC AAAATAATAT ACAACTAACT GATCCAATAC AACAAAAGA    10380

CCAGGAGGCT ATGTGTCGAG CTGTACGTTA TAGTTTTGCC GATTTAGGAG ACATTATTCG   10440

AGGAAGAGAT ATGTGGGATG AGGATAAGAG CTCAACAGAC ATGGAAACAC GTTTGATAAC   10500

CGTATTTAAA AACATTAAAG AAAAACATGA TGGAATCAAA GACAACCCTA AATATACCGG   10560

TGATGAAAGC AAAAAGCCCG CATATAAAAA ATTACGAGCA GATTGGTGGG AAGCAAATAG   10620

ACATCAAGTG TGGAGAGCCA TGAAATGCGC AACAAAAGGC ATCATATGTC CTGGTATGCC   10680

AGTTGACGAT TATATCCCCC AACGTTTACG CTGGATGACT GAATGGGCTG AATGGTATTG   10740

TAAAGCGCAA TCACAGGAGT ATGACAAGTT AAAAAAAATC TGTGCAGATT GTATGAGTAA   10800

GGGTGATGGA AAATGTACGC AAGGTGATGT CGATTGTGGA AAGTGCAAAG CAGCATGTGA   10860

TAAATATAAA GAGGAAATAG AAAAATGGAA TGAACAATGG AGAAAAATAT CAGATAAATA   10920

CAATCTATTA TACCTACAAG CAAAAACTAC TTCTACTAAT CCTGGCCGTA CTGTTCTTGG   10980

TGATGACGAT CCCGACTATC AACAAATGGT AGATTTTTTG ACCCCAATAC ACAAAGCAAG   11040

TATTGCCGCA CGTGTTCTTG TTAAACGTGC TGCTGGTAGT CCCACTGAGA TCGCCGCCGC   11100

CGCCCCGATC ACCCCCTACA GTACTGCTGC CGGATATATA CACCAGGAAA TAGGATATGG   11160

GGGGTGCCAG GAACAAACAC AATTTTGTGA AAAAAAACAT GGTGCAACAT CAACTAGTAC   11220

CACGAAAGAA AACAAAGAAT ACACCTTTAA ACAACCTCCG CCGGAGTATG CTACAGCGTG   11280

TGATTGCATA AATAGGTCGC AAACAGAGGA GCCGAAGAAA AAGGAAGAAA ATGTAGAGAG   11340

TGCCTGCAAA ATAGTGGAGA AAATACTTGA GGGTAAGAAT GGAAGGACTA CAGTAGGTGA   11400

ATGTAATCCA AAAGAGAGTT ATCCTGATTG GGATTGCAAA AACAATATTG ACATTAGTCA   11460

TGATGGTGCT TGTATGCCTC CAAGGAGACA AAAACTATGT TTATATTATA TAGCACATGA   11520

GAGTCAAACA GAAAATATAA AAACAGACGA TAATTTGAAA GATGCTTTTA TTAAAACTGC   11580

AGCAGCAGAA ACTTTTCTTT CATGGCAATA TTATAAGAGT AAGAATGATA GTGAAGCTAA   11640

AATATTAGAT AGAGGCCTTA TTCCATCCCA ATTTTTAAGA TCCATGATGT ACACGTTTGG   11700

AGATTATAGA GATATATGTT TGAACACAGA TATATCTAAA AAACAAAATG ATGTAGCTAA   11760

GGCAAAAGAT AAAATAGGTA AATTTTTCTC AAAAGATGGC AGCAAATCTC CTAGTGGCTT   11820

ATCACGCCAA GAATGGTGGA AAACAAATGG TCCAGAGATT TGGAAAGGAA TGTTATGTGC   11880

CTTAACAAAA TACGTCACAG ATACCGATAA CAAAAGAAAA ATCAAAAACG ACTACTCATA   11940

CGATAAAGTC AACCAATCCC AAAATGGCAA CCCTTCCCTT GAAGAGTTTG CTGCTAAACC   12000

TCAATTTCTA CGTTGGATGA TCGAATGGGG AGAAGAGTTT TGTGCTGAAC GTCAGAAGAA   12060

GGAAAATATC ATAAAAGATG CATGTAATGA AATAAATTCT ACACAACAGT GTAATGATGC   12120

GAAACATCGT TGTAATCAAG CATGTAGAGC ATATCAAGAA TATGTTGAAA ATAAAAAAAA   12180

AGAATTTTCG GGACAAACAA ATAACTTTGT TCTAAAGGCA AATGTTCAGC CCCAAGATCC   12240

AGAATATAAA GGATATGAAT ATAAAGACGG CGTACAACCG ATACAGGGGA ATGAGTATTT   12300

ACTGCAAAAA TGTGATAATA ATAAATGTTC TTGCATGGAT GGAAATGTAC TTTCCGTCTC   12360
```

```
TCCAAAAGAA AAACCTTTTG GAAAATATGC CCATAAATAT CCTGAGAAAT GTGATTGTTA    12420

TCAAGGAAAA CATGTACCTA GCATACCACC TCCCCCCCCA CCTGTACAAC CACAACCGGA    12480

AGCACCAACA GTAACAGTAG ACGTTTGCAG CATAGTAAAA ACACTATTTA AAGACACAAA    12540

CAATTTTTCC GACGCTTGTG GTCTAAAATA CGGCAAAACC GCACCATCCA GTTGGAAATG    12600

TATACCAAGT GACACAAAAA GTGGTGCTGG TGCCACCACC GGCAAAAGTG GTAGTGATAG    12660

TGGTAGTATT TGTATCCCAC CCAGGAGGCG ACGATTATAT GTGGGGAAAC TACAGGAGTG    12720

GGCTACCGCG CTCCCACAAG GTGAGGGCGC CGCGCCGTCC CACTCACGCG CCGACGACTT    12780

GCGCAATGCG TTCATCCAAT CTGCTGCAAT AGAGACTTTT TTCTTATGGG ATAGATATAA    12840

AGAAGAGAAA AAACCACAGG GTGATGGGTC ACAACAAGCA CTATCACAAC TAACCAGTAC    12900

ATACAGTGAT GACGAGGAGG ACCCCCCCGA CAAACTGTTA CAAAATGGTA AGATACCCCC    12960

CGATTTTTTG AGATTAATGT TCTATACATT AGGAGATTAT AGGGATATTT TAGTACACGG    13020

TGGTAACACA AGTGACAGTG GTAACACAAA TGGTAGTAAC AACAACAATA TTGTGCTTGA    13080

AGCGAGTGGT AACAAGGAGG ACATGCAAAA AATACAAGAG AAAATAGAAC AAATTCTCCC    13140

AAAAAATGGT GGCACACCTC TTGTCCCAAA ATCTAGTGCC CAAACACCTG ATAAATGGTG    13200

GAATGAACAC GCCGAATCTA TCTGGAAAGG TATGATATGT GCATTGACAT ATACAGAAAA    13260

GAACCCTGAC ACCAGTGCAA GAGGCGACGA AAACAAAATA GAAAAGGATG ATGAAGTGTA    13320

CGAGAAATTT TTTGGCAGCA CAGCCGACAA ACATGGCACA GCCTCAACCC CAACCGGCAC    13380

ATACAAAACC CAATACGACT ACGAAAAAGT CAAACTTGAG GATACAAGTG GTGCCAAAAC    13440

CCCCTCAGCC TCTAGTGATA CACCCCTTCT CTCCGATTTC GTGTTACGCC CCCCCTACTT    13500

CCGTTACCTT GAAGAATGGG GTCAAAATTT TTGTAAAAAA AGAAAGCATA AATTGGCACA    13560

AATAAAACAT GAGTGTAAAG TAGAAGAAAA TGGTGGTGGT AGTCGTCGTG GTGGTATAAC    13620

AAGACAATAT AGTGGGGATG GCGAAGCGTG TAATGAGATG CTTCCAAAAA ACGATGGAAC    13680

TGTTCCGGAT TTAGAAAAGC CGAGTTGTGC CAAACCTTGT AGTTCTTATA GAAAATGGAT    13740

AGAAAGCAAG GGAAAAGAGT TTGAGAAACA AGAAAAGGCA TATGAACAAC AAAAAGACAA    13800

ATGTGTAAAT GGAAGTAATA AGCATGATAA TGGATTTTGT GAAACACTAA CAACGTCCTC    13860

TAAAGCTAAA GACTTTTTAA AAACGTTAGG ACCATGTAAA CCTAATAATG TAGAGGGTAA    13920

AACAATTTTT GATGATGATA AAACCTTTAA ACATACAAAA GATTGTGATC CATGTCTTAA    13980

ATTTAGTGTT AATTGTAAAA AAGATGAATG TGATAATTCT AAAGGAACCG ATTGCCGAAA    14040

TAAAAATAGT ATTGATGCAA CAGATATTGA AAATGGAGTG GATTCTACTG TACTAGAAAT    14100

GCGTGTCAGT GCTGATAGTA AAAGTGGATT TAATGGTGAT GGTTTAGAGA ATGCTTGTAG    14160

AGGTGCTGGT ATCTTTGAAG GTATTAGAAA AGATGAATGG AAATGTCGTA ATGTATGTGG    14220

TTATGTTGTA TGTAAACCGG AAAACGTTAA TGGGGAAGCA AAGGGAAAAC ACATTATACA    14280

AATTAGAGCA CTGGTTAAAC GTTGGGTAGA ATATTTTTTT GAAGATTATA ATAAAATAAA    14340

ACATAAAATT TCACATCGCA TAAAAAATGG TGAAATATCT CCATGTATAA AAAATTGTGT    14400

AGAAAAATGG GTAGATCAGA AAAGAAAAGA ATGGAAGGAA ATTACTGAAC GTTTCAAAGA    14460

TCAATATAAA AATGACAATT CAGATGATGA CAATGTGAGA AGTTTTTTGG AGACCTTGAT    14520

ACCTCAAATT ACTGATGCAA ACGCTAAAAA TAAGGTTATA AAATTAAGTA AGTTCGGTAA    14580

TTCTTGTGGA TGTAGTGCCA GTGCGAACGA ACAAAACAAA AATGGTGAAT ACAAGGACGC    14640

TATAGATTGT ATGCTTAAAA AGCTTAAAGA TAAAATTGGC GAGTGCGAAA AGAAACACCA    14700

TCAAACTAGT GATACCGAGT GTTCCGACAC ACCACAACCG CAAACCCTTG AAGACGAAAC    14760
```

```
TTTGGATGAT GATATAGAAA CAGAGGAGGC GAAGAAGAAC ATGATGCCGA AAATTTGTGA   14820

AAATGTGTTA AAAACAGCAC AACAAGAGGA TGAAGGCGGT TGTGTCCCAG CAGAAAATAG   14880

TGAAGAACCG GCAGCAACAG ATAGTGGTAA GGAAACCCCC GAACAAACCC CCGTTCTCAA   14940

ACCCGAAGAA GAAGCAGTAC CGGAACCACC ACCTCCACCC CCACAGGAAA AAGCCCCGGC   15000

ACCAATACCC CAACCACAAC CACCAACCCC CCCCACACAA CTCTTGGATA ATCCCCACGT   15060

TCTAACCGCC CTGGTGACCT CCACCCTCGC CTGGAGCGTT GGCATCGGTT TTGCTACATT   15120

CACTTATTTT TATCTAAAGG TAAATGGAAG TATATATATG GGGATGTGGA TGTATGTGGA   15180

TGTATGTGAA TGTATGTGGA TGTATGTGGA TGTATGTGGA TGTGTTTTAT GGATATGTAT   15240

TTGTGATTAT GTTTGGATAT ATATATATAT ATATATATGT TTATGTATAT GTGTTTTTGG   15300

ATATATATAT GTGTATGTAT ATGATTTTCT GTATATGTAT TTGTGGGTTA AGGATATATA   15360

TATATGGATG TACTTGTATG TGTTTTATAT ATATATTTTA TATATATGTA TTTATATTAA   15420

AAAAGAAATA TAAAAACAAA TTTATTAAAA TGAAAAAAAG AAAAATGAAA TATAAAAAAA   15480

AATTTATTAA AATAAAAAAA AAAAAAAAAA AAAAGGAGAA AAATTTTTTA AAAAATAATA   15540

AAAATTATAA TAAAATATAA ATTTTGATAG AATAAAAAAT GAAAAAGATT ATCAAAAAAA   15600

AATTAAAAAA AAATTTTATA TAAAAAAAAA ATGATTATAA AAAAAATAAA AACAAAAGAA   15660

GAAAAAAAAA AACATTAAAA AAAAAAAAAT ATATATCATA AAAACAAAAA AAAAAGAAAA   15720

AAATATATTA AAATAAAAAT ATATATCATA AAATAAAAAA AAATTAAAAA AATGTTAAAA   15780

AAAAAATATA TACATAAAAT AAAAAAAATT TATTTAAATA AAAAAAAATA ATAAATAAAA   15840

AAATTTAATT AAATAAAAAA AAATAATAAA TAAAAAAATT TAATTAAATA AAAAAAAATT   15900

AAAAAAATTT AATGAAATAA AAAAAAATAA AAAAATTTAA TTAAATAAAA AAAATAAAAT   15960

AAAATTAATT ACATGCACAT ATACATACAT ATATATATAT ATATACCCAT AACTACATAC   16020

AACATTTACA CATACATATA TATATATATA TATACCCATA ACTACATACA CATTTACACA   16080

TACATATATA TATTATATAT ATATATATAT ATACCCATAA CTACATACAT ATATACATTA   16140

ACAAACACAT ATATAATACC TAAATACATA TATACATACA CATATATGTT CATTTTTTTT   16200

TTTAGAAAAA AACCAAATCA TCTGTTGGAA ATTTATTCCA AATACTGCAA ATACCCAAAA   16260

GTGATTATGA TATACCGACA AAACTTTCAC CCAATAGATA TATACCTTAT ACTAGTGGTA   16320

AATACAGAGG CAAACGGTAC ATTTACCTTG AAGGAGATAG TGGAACAGAT AGTGGTTACA   16380

CCGATCATTA TAGTGATATA ACTTCCTCAG AAAGTGAATA TGAAGAGATG GATATAAATG   16440

ATATATATGT ACCAGGTAGT CCTAAATATA AAACATTAAT TGAAGTGGTA CTTGAACCTA   16500

GTGGTAACAA CACAACAGCT AGTGGTAACA ACACAACAGC TAGTGGTAAC AACACAACAG   16560

CTAGTGGTAA AAACACACCT AGTGATACAC AAAATGATAT ACAAAATGAT GGTATACCTA   16620

GTAGTAAAAT TACAGATAAT GAATGGAATC AATTGAAAGA TGAATTTATA TCACAATATC   16680

TACAAAGTGA ACCAAATACA GAACCAAATA TGTTAGGTTA TAATGTGGAT AATAATACCC   16740

ATCCTACCAC GTCACATCAT AATGTGGAAG AAAAACCTTT TATTATGTCC ATTCATGATA   16800

GAAATTTATT TAGTGGAGAA GAATACAATT ATGATATGTT TAATAGTGGG AATAATCCAA   16860

TAAACATTAG TGATTCAACA AATAGTATGG ATAGTCTAAC AAGTAACAAC CATAGTCCAT   16920

ATAATGATAA AAATGATTTA TATAGTGGTA TCGACCTAAT CAACGACGCA CTAAGTGGTA   16980

ATCATATTGA TATATATGAT GAAATGCTCA AACGAAAGA AAATGAATTA TTTGGAACAA   17040

AACATCATAC AAAACATACA AATACATATA ATGTCGCCAA ACCTGCACGT GACGACCCTA   17100

TAACCAATCA AATAAATTTG TTCCATAAAT GGTTAGATAG GCATAGAGAT ATGTGCGAAA   17160
```

```
AGTGGAAAAA TAATCACGAA CGGTTACCCA AATTGAAAGA ATTGTGGGAA AATGAGACAC   17220

ATAGTGGTGA CATAAATAGT GGTATACCTA GTGGTAACCA TGTGTTGAAT ACTGATGTTT   17280

CTATTCAAAT AGATATGGAT AATCCTAAAA CAAAGAATGA AATTACGAAT ATGGATACAA   17340

ACCCAGACAA ATCTACTATG GATACTATAC TGGATGATCT GGAAAAATAT AATGAACCCT   17400

ACTACTATGA TTTTTATGAA GATGATATCA TCTATCATGA TGTAGATGTT GAAAAATCAT   17460

CTATGGATGA TATATATGTG GATCATAATA ATGTGACTAA TAATAATATG GATGTACCTA   17520

CTAAAATGCA CATCGAAATG AATATTGTTA ATAATAAAAA GGAGATTTTC GAAGAGGAAT   17580

ATCCTATATC AGATATATGG AATATCTAAA ATTAATATAC TTTTTTTGTG TGTGTCATAT   17640

ATATTTGTA TTATTTGTAT ATGTTTTTAT TTTATTTATT TATTTATTTA TTTATTGTTT   17700

TTGGTATATT TGTAAAAAAT ATGTTTTTGT TTATAATCAT ATTATTATAT TTTTAATAAT   17760

TTGCAACATG ATTTTTTTTT TTCTTTCTTA TTGTGTAATT TTTTTCATAA TATTTATATA   17820

TATATATGTA TTTTATTTTT TAGTATAATA ATTGTATCTA TATTTGATTA ATAATTATGT   17880

ATATTATGGT TATTTTGTTT CTTTTTCTGT ACATTTTTTC GTAATATATA TATATATATA   17940

TATATATAAT TCTCTTTTTC TAATATATAT ATCCTTCTAT TTTCGATTTT TTCATTTTTT   18000

TCCAGTATTA ATTTATTTAT TTATTTGTGA TATTTTATAA TATATTATTT AAATGTGTAT   18060

TTATATATGT GTTTTATATA TGTGTTTTAT TTTTGTTACT CTAATTCTGA ATAATCCGAG   18120

CGAAAAAAAA ATATATAATC TCATATAAAA ATTATTTATA ATACAATATT ATATAGTTTC   18180

CTATTAAAAT AAATTAATAT AATATACAAT AATATTTCTT GTTATTTTTA TAAATATAAC   18240

TAATTTCTTA TTTTTATTTA ACTTTATTCC TTTTTAATTT CTTAATTCTT TTATCAAACA   18300

AAAAACATAA AGTAATTCTA CATATCAACA AAAAAAAAAA AAAAAAAAAA AAAAAAATT   18360

TATTATAATA TAATAAAAAA TATAAAGACA TACGTTCACT TATTATTATA AATGATTTAT   18420

TACGATTAAA ACATATTGAG ATTATAATAA TATAATTTAA CATAGAAAGA GTTAAGAATA   18480

CATTTTTTTT TTTATTTCGA TATGTAATTC AACATATATA TATATATATA TCTTTTTAAT   18540

TTAATTAAAT AAAATTCCTT ATTATTCATA TTGTTTCTTT TATCACATGT GAAATATTAA   18600

AAATAATTTT CGATTTTATC GATATATTTA TGTCGTTTAT ATACTTATAT AGGTCTTTAT   18660

AACTATTGAT TAATAGAAGG TAATAGCCTA ATAAATAAAA TACTCGTATT TATAAATTCA   18720

TTTATATATT TCAAATATAT TTGCATGGTT TATTTTCAAA TACAATTAAT TAGATTTCTT   18780

AAATATTTCT TCATTTATTC ATTTTTATAG CATATACATG CACATTATAA ATTATTAATA   18840

AAAAATTTTT ATTTTAATAT ATAATAACAA TTTTCATACA TTACATTTTT CACACAACAT   18900

TTAAGTTGTC ATAATGTAAC ACATTAAATA ATATATTACT TATATATATA TAATTATTAA   18960

TTATATATTA AATAAAAATG TATTATCGCC TGTATTATCA TAGTATATAT AATGTTGTAT   19020

AACGCTTCAA AATATATATA ATAATATAAT TAAAATATA TATATAGTAA TTAATTATTT   19080

TGTTATGTTA TGTAATAATG CAATTAATAT AAGATAAAAT TCAT              19124
```

(2) INFORMATION FOR SEQ ID NO:14:

(i) SEQUENCE CHARACTERISTICS:
        (A) LENGTH: 3060 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Met Val Glu Leu Ala Lys Met Gly Pro Lys Glu Ala Gly Gly Asp
 1               5                  10                  15

Asp Ile Glu Asp Glu Ser Ala Lys His Met Phe Asp Arg Ile Gly Lys
                20                  25                  30

Asp Val Tyr Asp Lys Val Lys Glu Ala Lys Glu Arg Gly Lys Gly
                35                  40                  45

Leu Gln Gly Arg Leu Ser Glu Ala Lys Phe Glu Lys Asn Glu Ser Asp
 50                  55                  60

Pro Gln Thr Pro Glu Asp Pro Cys Asp Leu Asp His Lys Tyr His Thr
 65                  70                  75                  80

Asn Val Thr Thr Asn Val Ile Asn Pro Cys Ala Asp Arg Ser Asp Val
                85                  90                  95

Arg Phe Ser Asp Glu Tyr Gly Gly Gln Cys Thr His Asn Arg Ile Lys
                100                 105                 110

Asp Ser Gln Gln Gly Asp Asn Lys Gly Ala Cys Ala Pro Tyr Arg Arg
                115                 120                 125

Leu His Val Cys Asp Gln Asn Leu Glu Gln Ile Glu Pro Ile Lys Ile
                130                 135                 140

Thr Asn Thr His Asn Leu Leu Val Asp Val Cys Met Ala Ala Lys Phe
145                 150                 155                 160

Glu Gly Gln Ser Ile Thr Gln Asp Tyr Pro Lys Tyr Gln Ala Thr Tyr
                165                 170                 175

Gly Asp Ser Pro Ser Gln Ile Cys Thr Met Leu Ala Arg Ser Phe Ala
                180                 185                 190

Asp Ile Gly Asp Ile Val Arg Gly Arg Asp Leu Tyr Leu Gly Asn Pro
                195                 200                 205

Gln Glu Ile Lys Gln Arg Gln Gln Leu Glu Asn Asn Leu Lys Thr Ile
                210                 215                 220

Phe Gly Lys Ile Tyr Glu Lys Leu Asn Gly Ala Glu Ala Arg Tyr Gly
225                 230                 235                 240

Asn Asp Pro Glu Phe Phe Lys Leu Arg Glu Asp Trp Trp Thr Ala Asn
                245                 250                 255

Arg Glu Thr Val Trp Lys Ala Ile Thr Cys Asn Ala Trp Gly Asn Thr
                260                 265                 270

Tyr Phe His Ala Thr Cys Asn Arg Gly Glu Arg Thr Lys Gly Tyr Cys
                275                 280                 285

Arg Cys Asn Asp Asp Gln Val Pro Thr Tyr Phe Asp Tyr Val Pro Gln
                290                 295                 300

Tyr Leu Arg Trp Phe Glu Glu Trp Ala Glu Asp Phe Cys Arg Lys Lys
305                 310                 315                 320

Asn Lys Lys Ile Lys Asp Val Lys Arg Asn Cys Arg Gly Lys Asp Lys
                325                 330                 335

Glu Asp Lys Asp Arg Tyr Cys Ser Arg Asn Gly Tyr Asp Cys Glu Lys
                340                 345                 350

Thr Lys Arg Ala Ile Gly Lys Leu Arg Tyr Gly Lys Gln Cys Ile Ser
                355                 360                 365

Cys Leu Tyr Ala Cys Asn Pro Tyr Val Asp Trp Ile Asn Asn Gln Lys
370                 375                 380

Glu Gln Phe Asp Lys Gln Lys Lys Tyr Asp Glu Ile Lys Lys
385                 390                 395                 400

Tyr Glu Asn Gly Ala Ser Gly Gly Ser Arg Gln Lys Arg Asp Ala Gly
                405                 410                 415
```

-continued

```
Gly Thr Thr Thr Thr Asn Tyr Asp Gly Tyr Glu Lys Lys Phe Tyr Asp
            420                 425                 430

Glu Leu Asn Lys Ser Glu Tyr Arg Thr Val Asp Lys Phe Leu Glu Lys
            435                 440                 445

Leu Ser Asn Glu Glu Ile Cys Thr Lys Val Lys Asp Glu Glu Gly Gly
450                 455                 460

Thr Ile Asp Phe Lys Asn Val Asn Ser Asp Ser Thr Ser Gly Ala Ser
465                 470                 475                 480

Gly Thr Asn Val Glu Ser Gln Gly Thr Phe Tyr Arg Ser Lys Tyr Cys
                485                 490                 495

Gln Pro Cys Pro Tyr Cys Gly Val Lys Lys Val Asn Asn Gly Gly Ser
                500                 505                 510

Ser Asn Glu Trp Glu Lys Asn Asn Gly Lys Cys Lys Ser Gly Lys
                515                 520                 525

Leu Tyr Glu Pro Lys Pro Asp Lys Glu Gly Thr Thr Ile Thr Ile Leu
530                 535                 540

Lys Ser Gly Lys Gly His Asp Ile Glu Glu Lys Leu Asn Lys Phe
545                 550                 555                 560

Cys Asp Glu Lys Asn Gly Asp Thr Ile Asn Ser Gly Ser Gly Thr
                565                 570                 575

Gly Gly Ser Gly Gly Asn Ser Gly Arg Gln Glu Leu Tyr Glu Glu
            580                 585                 590

Trp Lys Cys Tyr Lys Gly Glu Asp Val Val Lys Val Gly His Asp Glu
            595                 600                 605

Asp Asp Glu Glu Asp Tyr Glu Asn Val Lys Asn Ala Gly Gly Leu Cys
            610                 615                 620

Ile Leu Lys Asn Gln Lys Lys Asn Lys Glu Glu Gly Gly Asn Thr Ser
625                 630                 635                 640

Glu Lys Glu Pro Asp Glu Ile Gln Lys Thr Phe Asn Pro Phe Tyr
                645                 650                 655

Tyr Trp Val Ala His Met Leu Lys Asp Ser Ile His Trp Lys Lys Lys
            660                 665                 670

Leu Gln Arg Cys Leu Gln Asn Gly Asn Arg Ile Lys Cys Gly Asn Asn
            675                 680                 685

Lys Cys Asn Asn Asp Cys Glu Cys Phe Lys Arg Trp Ile Thr Gln Lys
690                 695                 700

Lys Asp Glu Trp Gly Lys Ile Val Gln His Phe Lys Thr Gln Asn Ile
705                 710                 715                 720

Lys Gly Arg Gly Gly Ser Asp Asn Thr Ala Glu Leu Ile Pro Phe Asp
                725                 730                 735

His Asp Tyr Val Leu Gln Tyr Asn Leu Gln Glu Phe Leu Lys Gly
            740                 745                 750

Asp Ser Glu Asp Ala Ser Glu Glu Lys Ser Glu Asn Ser Leu Asp Ala
            755                 760                 765

Glu Glu Ala Glu Glu Leu Lys His Leu Arg Glu Ile Ile Glu Ser Glu
770                 775                 780

Asp Asn Asn Gln Glu Ala Ser Val Gly Gly Val Thr Glu Gln Lys
785                 790                 795                 800

Asn Ile Met Asp Lys Leu Leu Asn Tyr Glu Lys Asp Glu Ala Asp Leu
                805                 810                 815

Cys Leu Glu Ile His Glu Asp Glu Glu Glu Lys Glu Lys Gly Asp
            820                 825                 830

Gly Asn Glu Cys Ile Glu Glu Gly Glu Asn Phe Arg Tyr Asn Pro Cys
            835                 840                 845
```

-continued

Ser Gly Glu Ser Gly Asn Lys Arg Tyr Pro Val Leu Ala Asn Lys Val
    850                 855                 860

Ala Tyr Gln Met His His Lys Ala Lys Thr Gln Leu Ala Ser Arg Ala
865                 870                 875                 880

Gly Arg Ser Ala Leu Arg Gly Asp Ile Ser Leu Ala Gln Phe Lys Asn
                885                 890                 895

Gly Arg Asn Gly Ser Thr Leu Lys Gly Gln Ile Cys Lys Ile Asn Glu
            900                 905                 910

Asn Tyr Ser Asn Asp Ser Arg Gly Asn Ser Gly Pro Cys Thr Gly
        915                 920                 925

Lys Asp Gly Asp His Gly Val Arg Met Arg Ile Gly Thr Glu Trp
    930                 935                 940

Ser Asn Ile Glu Gly Lys Lys Gln Thr Ser Tyr Lys Asn Val Phe Leu
945                 950                 955                 960

Pro Pro Arg Arg Glu His Met Cys Thr Ser Asn Leu Glu Asn Leu Asp
                965                 970                 975

Val Gly Ser Val Thr Lys Asn Asp Lys Ala Ser His Ser Leu Leu Gly
            980                 985                 990

Asp Val Gln Leu Ala Ala Lys Thr Asp Ala Ala Glu Ile Ile Lys Arg
        995                 1000                1005

Tyr Lys Asp Gln Asn Asn Ile Gln Leu Thr Asp Pro Ile Gln Gln Lys
    1010                1015                1020

Asp Gln Glu Ala Met Cys Arg Ala Val Arg Tyr Ser Phe Ala Asp Leu
1025                1030                1035                1040

Gly Asp Ile Ile Arg Gly Arg Asp Met Trp Asp Glu Asp Lys Ser Ser
                1045                1050                1055

Thr Asp Met Glu Thr Arg Leu Ile Thr Val Phe Lys Asn Ile Lys Glu
            1060                1065                1070

Lys His Asp Gly Ile Lys Asp Asn Pro Lys Tyr Thr Gly Asp Glu Ser
        1075                1080                1085

Lys Lys Pro Ala Tyr Lys Lys Leu Arg Ala Asp Trp Trp Glu Ala Asn
    1090                1095                1100

Arg His Gln Val Trp Arg Ala Met Lys Cys Ala Thr Lys Gly Ile Ile
1105                1110                1115                1120

Cys Pro Gly Met Pro Val Asp Asp Tyr Ile Pro Gln Arg Leu Arg Trp
                1125                1130                1135

Met Thr Glu Trp Ala Glu Trp Tyr Cys Lys Ala Gln Ser Gln Glu Tyr
            1140                1145                1150

Asp Lys Leu Lys Lys Ile Cys Ala Asp Cys Met Ser Lys Gly Asp Gly
        1155                1160                1165

Lys Cys Thr Gln Gly Asp Val Asp Cys Gly Lys Cys Lys Ala Ala Cys
    1170                1175                1180

Asp Lys Tyr Lys Glu Glu Ile Glu Lys Trp Asn Glu Gln Trp Arg Lys
1185                1190                1195                1200

Ile Ser Asp Lys Tyr Asn Leu Leu Tyr Leu Gln Ala Lys Thr Thr Ser
                1205                1210                1215

Thr Asn Pro Gly Arg Thr Val Leu Gly Asp Asp Asp Tyr Gln
            1220                1225                1230

Gln Met Val Asp Phe Leu Thr Pro Ile His Lys Ala Ser Ile Ala Ala
        1235                1240                1245

Arg Val Leu Val Lys Arg Ala Ala Gly Ser Pro Thr Glu Ile Ala Ala
    1250                1255                1260

```
Ala Ala Pro Ile Thr Pro Tyr Ser Thr Ala Ala Gly Tyr Ile His Gln
1265                1270                1275                1280

Glu Ile Gly Tyr Gly Gly Cys Gln Glu Gln Thr Gln Phe Cys Glu Lys
            1285                1290                1295

Lys His Gly Ala Thr Ser Thr Ser Thr Thr Lys Glu Asn Lys Glu Tyr
            1300                1305                1310

Thr Phe Lys Gln Pro Pro Pro Glu Tyr Ala Thr Ala Cys Asp Cys Ile
        1315                1320                1325

Asn Arg Ser Gln Thr Glu Glu Pro Lys Lys Glu Glu Asn Val Glu
        1330                1335                1340

Ser Ala Cys Lys Ile Val Glu Lys Ile Leu Glu Gly Lys Asn Gly Arg
1345                1350                1355                1360

Thr Thr Val Gly Glu Cys Asn Pro Lys Glu Ser Tyr Pro Asp Trp Asp
                1365                1370                1375

Cys Lys Asn Asn Ile Asp Ile Ser His Asp Gly Ala Cys Met Pro Pro
            1380                1385                1390

Arg Arg Gln Lys Leu Cys Leu Tyr Tyr Ile Ala His Glu Ser Gln Thr
            1395                1400                1405

Glu Asn Ile Lys Thr Asp Asp Asn Leu Lys Asp Ala Phe Ile Lys Thr
        1410                1415                1420

Ala Ala Ala Glu Thr Phe Leu Ser Trp Gln Tyr Tyr Lys Ser Lys Asn
1425                1430                1435                1440

Asp Ser Glu Ala Lys Ile Leu Asp Arg Gly Leu Ile Pro Ser Gln Phe
                1445                1450                1455

Leu Arg Ser Met Met Tyr Thr Phe Gly Asp Tyr Arg Asp Ile Cys Leu
                1460                1465                1470

Asn Thr Asp Ile Ser Lys Lys Gln Asn Asp Val Ala Lys Ala Lys Asp
        1475                1480                1485

Lys Ile Gly Lys Phe Phe Ser Lys Asp Gly Ser Lys Ser Pro Ser Gly
        1490                1495                1500

Leu Ser Arg Gln Glu Trp Trp Lys Thr Asn Gly Pro Glu Ile Trp Lys
1505                1510                1515                1520

Gly Met Leu Cys Ala Leu Thr Lys Tyr Val Thr Asp Thr Asp Asn Lys
                1525                1530                1535

Arg Lys Ile Lys Asn Asp Tyr Ser Tyr Asp Lys Val Asn Gln Ser Gln
        1540                1545                1550

Asn Gly Asn Pro Ser Leu Glu Glu Phe Ala Ala Lys Pro Gln Phe Leu
        1555                1560                1565

Arg Trp Met Ile Glu Trp Gly Glu Glu Phe Cys Ala Glu Arg Gln Lys
1570                1575                1580

Lys Glu Asn Ile Ile Lys Asp Ala Cys Asn Glu Ile Asn Ser Thr Gln
1585                1590                1595                1600

Gln Cys Asn Asp Ala Lys His Arg Cys Asn Gln Ala Cys Arg Ala Tyr
        1605                1610                1615

Gln Glu Tyr Val Glu Asn Lys Lys Glu Phe Ser Gly Gln Thr Asn
        1620                1625                1630

Asn Phe Val Leu Lys Ala Asn Val Gln Pro Gln Asp Pro Glu Tyr Lys
        1635                1640                1645

Gly Tyr Glu Tyr Lys Asp Gly Val Gln Pro Ile Gln Gly Asn Glu Tyr
1650                1655                1660

Leu Leu Gln Lys Cys Asp Asn Asn Lys Cys Ser Cys Met Asp Gly Asn
1665                1670                1675                1680

Val Leu Ser Val Ser Pro Lys Glu Lys Pro Phe Gly Lys Tyr Ala His
                1685                1690                1695
```

-continued

Lys Tyr Pro Glu Lys Cys Asp Cys Tyr Gln Gly Lys His Val Pro Ser
            1700                1705                1710

Ile Pro Pro Pro Pro Pro Val Gln Pro Gln Pro Glu Ala Pro Thr
            1715                1720                1725

Val Thr Val Asp Val Cys Ser Ile Val Lys Thr Leu Phe Lys Asp Thr
            1730                1735                1740

Asn Asn Phe Ser Asp Ala Cys Gly Leu Lys Tyr Gly Lys Thr Ala Pro
1745                1750                1755                1760

Ser Ser Trp Lys Cys Ile Pro Ser Asp Thr Lys Ser Gly Ala Gly Ala
                1765                1770                1775

Thr Thr Gly Lys Ser Gly Ser Asp Ser Gly Ser Ile Cys Ile Pro Pro
            1780                1785                1790

Arg Arg Arg Arg Leu Tyr Val Gly Lys Leu Gln Glu Trp Ala Thr Ala
            1795                1800                1805

Leu Pro Gln Gly Glu Gly Ala Ala Pro Ser His Ser Arg Ala Asp Asp
            1810                1815                1820

Leu Arg Asn Ala Phe Ile Gln Ser Ala Ala Ile Glu Thr Phe Phe Leu
1825                1830                1835                1840

Trp Asp Arg Tyr Lys Glu Lys Lys Pro Gln Gly Asp Gly Ser Gln
                1845                1850                1855

Gln Ala Leu Ser Gln Leu Thr Ser Thr Tyr Ser Asp Asp Glu Glu Asp
            1860                1865                1870

Pro Pro Asp Lys Leu Leu Gln Asn Gly Lys Ile Pro Pro Asp Phe Leu
            1875                1880                1885

Arg Leu Met Phe Tyr Thr Leu Gly Asp Tyr Arg Asp Ile Leu Val His
            1890                1895                1900

Gly Gly Asn Thr Ser Asp Ser Gly Asn Thr Asn Gly Ser Asn Asn Asn
1905                1910                1915                1920

Asn Ile Val Leu Glu Ala Ser Gly Asn Lys Glu Asp Met Gln Lys Ile
                1925                1930                1935

Gln Glu Lys Ile Glu Gln Ile Leu Pro Lys Asn Gly Gly Thr Pro Leu
            1940                1945                1950

Val Pro Lys Ser Ser Ala Gln Thr Pro Asp Lys Trp Trp Asn Glu His
            1955                1960                1965

Ala Glu Ser Ile Trp Lys Gly Met Ile Cys Ala Leu Thr Tyr Thr Glu
            1970                1975                1980

Lys Asn Pro Asp Thr Ser Ala Arg Gly Asp Glu Asn Lys Ile Glu Lys
1985                1990                1995                2000

Asp Asp Glu Val Tyr Glu Lys Phe Phe Gly Ser Thr Ala Asp Lys His
            2005                2010                2015

Gly Thr Ala Ser Thr Pro Thr Gly Thr Tyr Lys Thr Gln Tyr Asp Tyr
            2020                2025                2030

Glu Lys Val Lys Leu Glu Asp Thr Ser Gly Ala Lys Thr Pro Ser Ala
            2035                2040                2045

Ser Ser Asp Thr Pro Leu Leu Ser Asp Phe Val Leu Arg Pro Pro Tyr
2050                2055                2060

Phe Arg Tyr Leu Glu Glu Trp Gly Gln Asn Phe Cys Lys Lys Arg Lys
2065                2070                2075                2080

His Lys Leu Ala Gln Ile Lys His Glu Cys Lys Val Glu Glu Asn Gly
            2085                2090                2095

Gly Gly Ser Arg Arg Gly Gly Ile Thr Arg Gln Tyr Ser Gly Asp Gly
            2100                2105                2110

-continued

```
Glu Ala Cys Asn Glu Met Leu Pro Lys Asn Asp Gly Thr Val Pro Asp
    2115                2120                2125

Leu Glu Lys Pro Ser Cys Ala Lys Pro Cys Ser Ser Tyr Arg Lys Trp
2130                2135                2140

Ile Glu Ser Lys Gly Lys Glu Phe Glu Lys Gln Glu Lys Ala Tyr Glu
    2145                2150                2155                2160

Gln Gln Lys Asp Lys Cys Val Asn Gly Ser Asn Lys His Asp Asn Gly
                2165                2170                2175

Phe Cys Glu Thr Leu Thr Thr Ser Ser Lys Ala Lys Asp Phe Leu Lys
            2180                2185                2190

Thr Leu Gly Pro Cys Lys Pro Asn Asn Val Glu Gly Lys Thr Ile Phe
        2195                2200                2205

Asp Asp Asp Lys Thr Phe Lys His Thr Lys Asp Cys Asp Pro Cys Leu
    2210                2215                2220

Lys Phe Ser Val Asn Cys Lys Lys Asp Glu Cys Asp Asn Ser Lys Gly
2225                2230                2235                2240

Thr Asp Cys Arg Asn Lys Asn Ser Ile Asp Ala Thr Asp Ile Glu Asn
                2245                2250                2255

Gly Val Asp Ser Thr Val Leu Glu Met Arg Val Ser Ala Asp Ser Lys
            2260                2265                2270

Ser Gly Phe Asn Gly Asp Gly Leu Glu Asn Ala Cys Arg Gly Ala Gly
        2275                2280                2285

Ile Phe Glu Gly Ile Arg Lys Asp Glu Trp Lys Cys Arg Asn Val Cys
    2290                2295                2300

Gly Tyr Val Val Cys Lys Pro Glu Asn Val Asn Gly Glu Ala Lys Gly
2305                2310                2315                2320

Lys His Ile Ile Gln Ile Arg Ala Leu Val Lys Arg Trp Val Glu Tyr
                2325                2330                2335

Phe Phe Glu Asp Tyr Asn Lys Ile Lys His Lys Ile Ser His Arg Ile
            2340                2345                2350

Lys Asn Gly Glu Ile Ser Pro Cys Ile Lys Asn Cys Val Glu Lys Trp
        2355                2360                2365

Val Asp Gln Lys Arg Lys Glu Trp Lys Glu Ile Thr Glu Arg Phe Lys
    2370                2375                2380

Asp Gln Tyr Lys Asn Asp Asn Ser Asp Asp Asn Val Arg Ser Phe
2385                2390                2395                2400

Leu Glu Thr Leu Ile Pro Gln Ile Thr Asp Ala Asn Ala Lys Asn Lys
                2405                2410                2415

Val Ile Lys Leu Ser Lys Phe Gly Asn Ser Cys Gly Cys Ser Ala Ser
            2420                2425                2430

Ala Asn Glu Gln Asn Lys Asn Gly Glu Tyr Lys Asp Ala Ile Asp Cys
        2435                2440                2445

Met Leu Lys Lys Leu Lys Asp Lys Ile Gly Glu Cys Glu Lys Lys His
    2450                2455                2460

His Gln Thr Ser Asp Thr Glu Cys Ser Asp Thr Pro Gln Pro Gln Thr
2465                2470                2475                2480

Leu Glu Asp Glu Thr Leu Asp Asp Ile Glu Thr Glu Glu Ala Lys
                2485                2490                2495

Lys Asn Met Met Pro Lys Ile Cys Glu Asn Val Leu Lys Thr Ala Gln
            2500                2505                2510

Gln Glu Asp Glu Gly Gly Cys Val Pro Ala Glu Asn Ser Glu Pro
        2515                2520                2525

Ala Ala Thr Asp Ser Gly Lys Glu Thr Pro Glu Gln Thr Pro Val Leu
    2530                2535                2540
```

```
Lys Pro Glu Glu Ala Val Pro Glu Pro Pro Pro Pro Pro Gln
2545                2550                2555                2560

Glu Lys Ala Pro Ala Pro Ile Pro Gln Pro Gln Pro Thr Pro Pro
            2565                2570                2575

Thr Gln Leu Leu Asp Asn Pro His Val Leu Thr Ala Leu Val Thr Ser
                2580                2585                2590

Thr Leu Ala Trp Ser Val Gly Ile Gly Phe Ala Thr Phe Thr Tyr Phe
            2595                2600                2605

Tyr Leu Lys Lys Lys Thr Lys Ser Ser Val Gly Asn Leu Phe Gln Ile
        2610                2615                2620

Leu Gln Ile Pro Lys Ser Asp Tyr Asp Ile Pro Thr Lys Leu Ser Pro
2625                2630                2635                2640

Asn Arg Tyr Ile Pro Tyr Thr Ser Gly Lys Tyr Arg Gly Lys Arg Tyr
                2645                2650                2655

Ile Tyr Leu Glu Gly Asp Ser Gly Thr Asp Ser Gly Tyr Thr Asp His
            2660                2665                2670

Tyr Ser Asp Ile Thr Ser Ser Glu Ser Glu Tyr Glu Glu Met Asp Ile
            2675                2680                2685

Asn Asp Ile Tyr Val Pro Gly Ser Pro Lys Tyr Lys Thr Leu Ile Glu
2690                2695                2700

Val Val Leu Glu Pro Ser Gly Asn Asn Thr Thr Ala Ser Gly Asn Asn
2705                2710                2715                2720

Thr Thr Ala Ser Gly Asn Asn Thr Thr Ala Ser Gly Lys Asn Thr Pro
            2725                2730                2735

Ser Asp Thr Gln Asn Asp Ile Gln Asn Asp Gly Ile Pro Ser Ser Lys
                2740                2745                2750

Ile Thr Asp Asn Glu Trp Asn Gln Leu Lys Asp Glu Phe Ile Ser Gln
            2755                2760                2765

Tyr Leu Gln Ser Glu Pro Asn Thr Glu Pro Asn Met Leu Gly Tyr Asn
            2770                2775                2780

Val Asp Asn Asn Thr His Pro Thr Thr Ser His His Asn Val Glu Glu
2785                2790                2795                2800

Lys Pro Phe Ile Met Ser Ile His Asp Arg Asn Leu Phe Ser Gly Glu
                2805                2810                2815

Glu Tyr Asn Tyr Asp Met Phe Asn Ser Gly Asn Asn Pro Ile Asn Ile
            2820                2825                2830

Ser Asp Ser Thr Asn Ser Met Asp Ser Leu Thr Ser Asn Asn His Ser
            2835                2840                2845

Pro Tyr Asn Asp Lys Asn Asp Leu Tyr Ser Gly Ile Asp Leu Ile Asn
    2850                2855                2860

Asp Ala Leu Ser Gly Asn His Ile Asp Ile Tyr Asp Glu Met Leu Lys
2865                2870                2875                2880

Arg Lys Glu Asn Glu Leu Phe Gly Thr Lys His His Thr Lys His Thr
                2885                2890                2895

Asn Thr Tyr Asn Val Ala Lys Pro Ala Arg Asp Asp Pro Ile Thr Asn
            2900                2905                2910

Gln Ile Asn Leu Phe His Lys Trp Leu Asp Arg His Arg Asp Met Cys
            2915                2920                2925

Glu Lys Trp Lys Asn Asn His Glu Arg Leu Pro Lys Leu Lys Glu Leu
            2930                2935                2940

Trp Glu Asn Glu Thr His Ser Gly Asp Ile Asn Ser Gly Ile Pro Ser
2945                2950                2955                2960
```

```
Gly Asn His Val Leu Asn Thr Asp Val Ser Ile Gln Ile Asp Met Asp
            2965                2970                2975

Asn Pro Lys Thr Lys Asn Glu Ile Thr Asn Met Asp Thr Asn Pro Asp
            2980                2985                2990

Lys Ser Thr Met Asp Thr Ile Leu Asp Asp Leu Glu Lys Tyr Asn Glu
            2995                3000                3005

Pro Tyr Tyr Tyr Asp Phe Tyr Glu Asp Ile Ile Tyr His Asp Val
            3010                3015                3020

Asp Val Glu Lys Ser Ser Met Asp Asp Ile Tyr Val Asp His Asn Asn
3025            3030                3035                3040

Val Thr Asn Asn Asn Met Asp Val Pro Thr Lys Met His Ile Glu Met
                3045                3050                3055

Asn Ile Val Asn
            3060

(2) INFORMATION FOR SEQ ID NO:15:

(i) SEQUENCE CHARACTERISTICS:
        (A) LENGTH: 7295 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

TCCAAGCTGT TTTTTTTTCT TTTTCTAGTT TTTCCATTGT ATATTCGTCA AATACGTACA      60

CATATATATA TATGTATA ACATGTGAGT ATTATTTTAT ACATCACATC GATTACATTT       120

TAGCGTTTTT TTTCCCCAGA TCACATATAG TACGACTAAG AAACAAAATA ACATCATAAC     180

AAACATAGTG ATTATCAATA CATGATATTA CCACATAATA TAAAGTATTA ATAATATTA     240

TTGCATGTTA GTGATAACTA CTATATCATA TACACCACTA CTAACTATCA CTACATAGTA    300

ACAGTAGTAG TCACAATCAT AGCATCATGG TAATATAGAT TTTCATTTCA TATCTTCCTT    360

ATTGTTTGTT ATACATACAC TATTAATATG TATTTATGTT ATAATGGTAG ACTATGTTAA   420

CAATGTATGA ATGACCATCA TAAATTAATA ACAGACGCAT CAAAACAGTG TATATGTGTG   480

CATTTATGAC ATAATGTAGT CGGGAAGCAT ACAAAAATGG AGCCAGGAGG TAGCGGTGGT    540

CGTGGTAGTG GCGGTAGTAG TAGTGGTAAA GGGAAGAAGG ATACATCTGA GTATATTTAT    600

GTGAGCGATG CTAAGGATCT TTTGATAGA GTTGGAGAAA AAGTGTACGA AGAAAAAGTG    660

AAAAATGGTG ATGCTAAAAA ATATATTGAG GCGTTGAAAG GAAATTTGAA CACAGCAAAT   720

GGTCGTAGTT CGGAAACAGC TAGCAGTATT GAAACGTGCA CCCTTGTAAA AGAATATTAT   780

GAGCGTGTTA ATGGTGATGG TAAAAGGCAT CCGTGCAGAA AAGACGCAAA AAATGAAGAT   840

GTAAACCGTT TTTCGGATAC ACTTGGTGGC CAATGTACAT ACAATAGGAT AAAAGATAGT   900

CAACAGGGTG ATAATAAAGT AGGAGCCTGT GCTCCGTATA GACGATTACA TTTATGTGAT   960

TATAATTTGG AATCTATAGA CACAACGTCG ACGACGCATA AGTTGTTGTT AGAGGTGTGT  1020

ATGGCAGCAA AATACGAAGG AAACTCAATA AATCACATT ATACACAACA TCAACGAACT  1080

AATGAGGATT CTGCTTCCCA ATTATGTACT GTATTAGCAC GAAGTTTTGC AGATATAGGT  1140

GATATCGTAA GAGGAAAAGA TCTATATCTC GGTTATGATA ATAAAGAAAA AGAACAAAGA  1200

AAAAAATTAG AACAGAAATT GAAAGATATT TTCAAGAAAA TACATAAGGA CGTGATGAAG  1260
```

-continued

```
ACGAATGGCG CACAAGAACG CTACATAGAT GATGCCAAAG GAGGAGATTT TTTTCAATTA    1320

AGAGAAGATT GGTGGACGTC GAATCGAGAA ACAGTATGGA AAGCATTAAT ATGTCATGCA    1380

CCAAAAGAAG CTAATTATTT TATAAAAACA GCGTGTAATG TAGGAAAAGG AACTAATGGT    1440

CAATGCCATT GCATTGGTGG AGATGTTCCC ACATATTTCG ATTATGTGCC GCAGTATCTT    1500

CGCTGGTTCG AGGAATGGGC AGAAGACTTT TGCAGGAAAA AAAAAAAAAA ACTAGAAAAT    1560

TTGCAAAAAC AGTGTCGTGA TTACGAACAA AATTTATATT GTAGTGGTAA TGGCTACGAT    1620

TGCACAAAAA CTATATATAA AAAAGGTAAA CTTGTTATAG GTAACATTG TACAAACTGT     1680

TCTGTTTGGT GTCGTATGTA TGAAACTTGG ATAGATAACC AGAAAAAGA ATTTCTAAAA     1740

CAAAAAAGAA AATACGAAAC AGAAATATCA GGTGGTGGTA GTGGTAAGAG TCCTAAAAGG    1800

ACAAAACGGG CTGCACGTAG TAGTAGTAGT AGTGATGATA ATGGGTATGA AAGTAAATTT    1860

TATAAAAAAC TGAAAGAAGT TGGCTACCAA GATGTCGATA AATTTTTAAA AATATTAAAC    1920

AAAGAAGGAA TATGTCAAAA ACAACCTCAA GTAGGAAATG AAAAAGCAGA TAATGTTGAT    1980

TTTACTAATG AAAATATGT AAAAACATTT TCTCGTACAG AAATTTGTGA ACCGTGCCCA     2040

TGGTGTGGAT TGGAAAAAGG TGGTCCACCA TGGAAAGTTA AAGGTGACAA AACCTGCGGA    2100

AGTGCAAAAA CAAAGACATA CGATCCTAAA AATATTACCG ATATACCAGT ACTCTACCCT    2160

GATAAATCAC AGCAAAATAT ACTAAAAAAA TATAAAAATT TTTGTGAAAA AGGTGCACCT    2220

GGTGGTGGTC AAATTAAAAA ATGGCAATGT TATTATGATG AACATAGGCC TAGTAGTAAA    2280

AATAATAATA ATTGTGTAGA AGGAACATGG GACAAGTTTA CACAAGGTAA ACAAACCGTT    2340

AAGTCCTATA ATGTTTTTTT TTGGGATTGG GTTCATGATA TGTTACACGA TTCTGTAGAG    2400

TGGAAGACAG AACTTAGTAA GTGTATAAAT AATAACACTA ATGGCAACAC ATGTAGAAAC    2460

AATAATAAAT GTAAAACAGA TTGTGGTTGT TTTCAAAAAT GGGTTGAAAA AAAACAACAA    2520

GAATGGATGG CAATAAAAGA CCATTTTGGA AAGCAAACAG ATATTGTCCA ACAAAAAGGT    2580

CTTATCGTAT TTAGTCCCTA TGGAGTTCTT GACCTTGTTT TGAAGGGCGG TAATCTGTTG    2640

CAAAATATTA AAGATGTTCA TGGAGATACA GATGACATAA AACACATTAA GAAACTGTTG    2700

GATGAGGAAG ACGCAGTAGC AGTTGTTCTT GGTGGCAAGG ACAATACCAC AATTGATAAA    2760

TTACTACAAC ACGAAAAAGA ACAAGCAGAA CAATGCAAAC AAAAGCAGGA AGAATGCGAG    2820

AAAAAAGCAC AACAAGAAAG TCGTGGTCGC TCCGCCGAAA CCCGCGAAGA CGAAAGGACA    2880

CAACAACCTG CTGATAGTGC CGGCGAAGTC GAAGAAGAAG AAGACGACGA CGACTACGAC    2940

GAAGACGACG AAGATGACGA CGTAGTCCAG GAGGAGGAAG AGGGAAAGGA GGAAGGAACG    3000

GTCACAGAGG TAACAGAGGT AACAGAGGTC GTGGAAGAGA CGGTAACAGA ACAGGAAGGG    3060

GTGAAGCCAT GTGACATAGT GGGCAAACTA TTTGAGGACG ACAAAAGTCT CAAAGAGGCA    3120

TGTGGTCTAA AATACGGTCC AGGTGGAAAA GAAAAATTCC CCAATTGGAA GTGTGTCACA    3180

CCAAGTGGTG TCAGTACTGC CACTAGTGGA AAAGACGGCG CTATATGTGT GCCACCCAGG    3240

AGACGACGAT TATACGTAGG TGGTTTATCA CAATGGGCAA GTCGTGGTGG TGACGAGACC    3300

ACGGAGGTGT CGAGTGAAGC CACTTCGGCG CCGTCACAGT CAGAAAGTGA AAAACTACGT    3360

ACTGCGTTTA TTGAGTCCGC TGCAATAGAG ACGTTTTTTT TGTGGCATAA GTATAAAGAA    3420

GAGAAAAAAC CACCAGCAAC ACAAGATGGA GCGGGACTTG GAGTATCACT CCCAGAACCG    3480

TCACCACCGG GAGAGGACCC CCAAACACAA TTACAACAAA CTGGTGTTAT ACCCCCCGAT    3540

TTTTTGCGTC AAATGTTTTA TACATTAGCA GACTACAAAG ACATATTATA CAGTGGTAGT    3600

AACGACACAA GTGACACAAC TGGTAAACAG ACACCTAGTA GTAGTAATGA CAACCTCAAA    3660
```

```
AATATTGTTC TGGAAGCAAG TGGTAGTACT GAGCAGGAGA AGGAGAAAAT GAAACAAATA    3720

CAAGCGAAAA TAAAAAAAAT TTTAAACGGT GCCACATCTG GTGTCCCACC TGTCACCAAA    3780

AATAGTGTCA AAACCCCCCA ACAAACCTGG TGGGAAAACA TCGCGAAGGA TATCTGGAAT    3840

GCTATGGTAT GTGCACTAAC ATATAAAGAA AATGACGCCA GAGGCACAAG TGCCAAAATA    3900

GAACAGAATA AGGATTTGAA AAAGGCACTT TGGGACGAAG CCAACAAAAA CACCCCCATA    3960

GAGAAATACC AATACACAAA TGTCAAACTC GAAGATGAAA GTGGTGCCAA AAGCAACGAC    4020

ACCATCCAAC CCCCCACGTT AAAAAATTTT GTGGAAATAC CTACATTTTT TCGTTGGTTA    4080

CATGAGTGGG GAAACAGTTT TTGTTTTGAG AGAGCAAAAC GATTGGCACA AATAAAACAT    4140

GAGTGTATGG ATGAGGATGG TGAAAAACAA TATAGTGGGG ATGGGAATA TTGTGAAGAA     4200

ATTTTTAGTA AGCAATATAA TGTTCTCCAG GATTTAAGTT CCAGTTGCGC TAAACCTTGT    4260

AGATTGTATA AAACGTGGAT AGAAAAAAAA AAAACAGAAT ATGAGAAACA ACAAAAGGCA    4320

TATGAACAAC AAAAAAGTAA TTACGAAAAT GAACAAAAAG ACAAATGCCA AACACAAAGT    4380

AATAATAATG CTAATGAATT TTCTAGAACA CTAGGAGCGT CCCCTACAGC TGCAGAATTT    4440

TTACAAAAGT TAGGATCATG TAAAAATGAT AATGGATATG AGAATGGAGA GGATAATAAA    4500

ATAGATTTTA AAAATCCAGA TAAAACATTT AAGGAAGCAC ACAGTTGTGA TCCATGTCCT    4560

ATAACTGGAG TTAAATGTCA AAATGGTCAT TGTGTGGGTT CTGCTAATGG AAAGGAGTGC    4620

AAAAACAATA AGATTACTGC AGAAGATATT AAAAATAAGA CAGATCCTAA TGGAAACATA    4680

GAAATGGTTG TCAGTGATGA CAGTACAAAT ACATTTGAAC ATTTAGGCGA TTGTAAAAGC    4740

TCAGGTATCT TTAAAGGTAT CAGAAAAGAT GAATGGAAAT GCGCTAATGT ATGTGGTGTA    4800

GATATATGTA CTCTGGAAAA AAAAATTAAG AATGGGCAAG AAGGTGATAA AAAATATATC    4860

ACAATGAAAG AATTGCTTAA ACGATGGCTA GAATATTTTT TAGAAGATTA TAATAGAATT    4920

AGAAAAAAAA TAAAGCTATG TACGAAAAAG GAAGATGGAT GCAAATGTAT AAAAGGTTGT    4980

ATAGAAAAAT GGGTACAAGA AAAAACGAAA GAATGGCAAA AATAAACGA TACTTATCTT     5040

GAACAATATA AAAATGATGA TGGTAATACT TTAACTAATT TTTTGGAGCA ATTCCAATAT    5100

CGAACTGAAT TTAAAAACGC TATAAAACCT TGTGATGGTT TAGACCAGTT CAAGACTTCG    5160

TGTGGTCTTA ATAGTACTGA TAATTCACAA AATGGTAATA ATAACGATCT TGTTCTATGT    5220

TTGCTTAATA AACTTCAAAA AAAAATTAGT GAGTGTAAAG AACAACATAG TGGCCAAACC    5280

CAAACACCGT GTGATAACTC TTCCCTTAGT GGTAAAGAAT CCACCCTCGT TGAAGACGTT    5340

GATGATTATG AGGAACAAAA CCCAGAAAAC AAAGTGGAAC AACCTAAATT TTGTCCAGAT    5400

ATGAAAGAAC CAAAAAAGA AAACGATGAA GAAGTAGGCA CTTGTGGCGG AGACGAAGAA     5460

AAAAAAAAAG TGGAAGACAG TGTAATCGAA CAAAAAGAGG AAGAAGCAGC TAGTGCCCCA    5520

GAGGAATCTC CTCCATTAAC CCCGGAAGCA CCAAAAAAAG AGGAAAATGT GGTACCAAAA    5580

CCACCACCAC CACCAAAAAA ACGCCGAATC AAAACCCGTA ATGTGTTGGA CCACCCCGCT    5640

GTCATACCCG CCCTCATGTC TTCTACCATC ATGTGGAGTA TTGGCATCGG TTTTGCTGCG    5700

TTCACTTATT TTTATCTAAA GAAAAAAACC AAATCATCTG TTGGAAATTT ATTCCAAATA    5760

CTGCAAATAC CCAAAAGTGA TTATGATATA CCTACATTGA AATCAAGCAA TCGTTATATA    5820

CCCTATGCAA GTGATAGACA TAAAGGCAAA ACATATATTT ATATGGAAGG AGATAGCAGT    5880

GGAGATGAAA AATATGCATT TATGTCTGAT ACTACTGATA TAACTTCATC CGAAAGTGAG    5940

TATGAAGAAT TGGATATTAA TGATATATAT GTACCAGGTA GTCCTAAATA TAAAACATTG    6000

ATAGAAGTAG TACTTGAACC ATCAAAAAGA GATACACAAA ATGATATACA CAATGATATA    6060
```

```
CCTAGTGATA TACCAAATAG TGACACACCA CCACCCATTA CTGATGATGA ATGGAATCAA      6120

TTGAAAAAAG ATTTTATATC TAATATGTTA CAAAATACAC AAAATACGGA ACCAAATATT      6180

TTACATGATA ATGTGGATAA TAATACCCAT CCTACCATGT CACGTCATAA TATGGACCAA      6240

AAACCTTTTA TTATGTCCAT ACATGATAGA AATTTATTTA GTGGAGAAGA ATACAATTAT      6300

GATATGTTTA ATAGTGGGAA TAATCCAATA AACATTAGTG ATTCAACAAA TAGTATGGAT      6360

AGTCTAACAA GTAACAACCA TAGTCCATAT AATGATAAAA ATGATTTATA TAGTGGTATC      6420

GACCTAATCA ACGACGCACT AAGTGGTAAT CATATTGATA TATATGATGA AATGCTCAAA      6480

CGAAAAGAAA ATGAATTATT CGGGACGCAA CATCATCCAA AAAATATAAC GTCTAACCGT      6540

GTCGTTACCC AAACAAGTAG TGACGACCCT ATAACCAATC AAATAAATTT GTTCCATAAA      6600

TGGTTAGATA GGCATAGAGA TATGTGCGAA AAGTGGAAAA ATAATCACGA ACGGTTACCC      6660

AAATTGAAAG AATTGTGGGA AAATGAGACA CATAGTGGTG ACATAAATAG TGGTATACCT      6720

AGTGGTAACC ATGTGTTGAA TACTGATGTT TCTATTCAAA TAGATATGGA TAATCCGAAA      6780

ACAATGAATG AATTTACTAA TATGGATACA AACCCCGACA AATCTACTAT GGATACTATA      6840

TTGGATGATC TAGAAAAATA TAACGAACCC TACTACTATG ATTTTTATAA ACATGATATC      6900

TATTATGATG TAAATGATGA TAAAGCATCT GAGGATCATA TAAATATGGA TCATAATAAG      6960

ATGGATAATA ATAATTCGGA TGTCCCCACT AACGTACAAA TTGAAATGAA TGTCATTAAT      7020

AATCAGGAGT TACTACAAAA TGAATATCCT ATATCGCATA TGTAGGGAAT ATGAAAATAA      7080

TAGATGTATA TATGTTTTTT TCTTTTTTTG TGTGTGTGCA GTTTATATTT TTTATTTGTA      7140

GATGTTATAT ATTTTTTTTA TTTGTGGGTT ATATTATAAT TTTTATTTAT GGGTTATATA      7200

TATATTTTTT TTTTTGTGCA TTTGTCTATT TTTTATTTGT GCTTTATATA TATATATATT      7260

TTATTCAGCT TGGACTTAAC CAGGCTGAAC TTGCT                                 7295
```

(2) INFORMATION FOR SEQ ID NO:16:

(i) SEQUENCE CHARACTERISTICS:
        (A) LENGTH: 2182 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:16:

```
Met Glu Pro Gly Gly Ser Gly Gly Arg Gly Ser Gly Ser Ser Ser
1               5                   10                  15

Gly Lys Gly Lys Lys Asp Thr Ser Glu Tyr Ile Tyr Val Ser Asp Ala
            20                  25                  30

Lys Asp Leu Leu Asp Arg Val Gly Glu Lys Val Tyr Glu Glu Lys Val
        35                  40                  45

Lys Asn Gly Asp Ala Lys Lys Tyr Ile Glu Ala Leu Lys Gly Asn Leu
    50                  55                  60

Asn Thr Ala Asn Gly Arg Ser Ser Glu Thr Ala Ser Ser Ile Glu Thr
65                  70                  75                  80

Cys Thr Leu Val Lys Glu Tyr Tyr Glu Arg Val Asn Gly Asp Gly Lys
                85                  90                  95
```

-continued

```
Arg His Pro Cys Arg Lys Asp Ala Lys Asn Glu Asp Val Asn Arg Phe
        100                 105                 110
Ser Asp Thr Leu Gly Gly Gln Cys Thr Tyr Asn Arg Ile Lys Asp Ser
            115                 120                 125
Gln Gln Gly Asp Asn Lys Val Gly Ala Cys Ala Pro Tyr Arg Arg Leu
130                 135                 140
His Leu Cys Asp Tyr Asn Leu Glu Ser Ile Asp Thr Thr Ser Thr Thr
145                 150                 155                 160
His Lys Leu Leu Leu Glu Val Cys Met Ala Ala Lys Tyr Glu Gly Asn
                165                 170                 175
Ser Ile Asn Thr His Tyr Thr Gln His Gln Arg Thr Asn Glu Asp Ser
                180                 185                 190
Ala Ser Gln Leu Cys Thr Val Leu Ala Arg Ser Phe Ala Asp Ile Gly
            195                 200                 205
Asp Ile Val Arg Gly Lys Asp Leu Tyr Leu Gly Tyr Asp Asn Lys Glu
210                 215                 220
Lys Glu Gln Arg Lys Lys Leu Glu Gln Lys Leu Lys Asp Ile Phe Lys
225                 230                 235                 240
Lys Ile His Lys Asp Val Met Lys Thr Asn Gly Ala Gln Glu Arg Tyr
                245                 250                 255
Ile Asp Asp Ala Lys Gly Gly Asp Phe Phe Gln Leu Arg Glu Asp Trp
            260                 265                 270
Trp Thr Ser Asn Arg Glu Thr Val Trp Lys Ala Leu Ile Cys His Ala
            275                 280                 285
Pro Lys Glu Ala Asn Tyr Phe Ile Lys Thr Ala Cys Asn Val Gly Lys
        290                 295                 300
Gly Thr Asn Gly Gln Cys His Cys Ile Gly Gly Asp Val Pro Thr Tyr
305                 310                 315                 320
Phe Asp Tyr Val Pro Gln Tyr Leu Arg Trp Phe Glu Glu Trp Ala Glu
                325                 330                 335
Asp Phe Cys Arg Lys Lys Lys Lys Leu Glu Asn Leu Gln Lys Gln
            340                 345                 350
Cys Arg Asp Tyr Glu Gln Asn Leu Tyr Cys Ser Gly Asn Gly Tyr Asp
            355                 360                 365
Cys Thr Lys Thr Ile Tyr Lys Lys Gly Lys Leu Val Ile Gly Glu His
370                 375                 380
Cys Thr Asn Cys Ser Val Trp Cys Arg Met Tyr Glu Thr Trp Ile Asp
385                 390                 395                 400
Asn Gln Lys Lys Glu Phe Leu Lys Gln Lys Arg Lys Tyr Glu Thr Glu
                405                 410                 415
Ile Ser Gly Gly Gly Ser Gly Lys Ser Pro Lys Arg Thr Lys Arg Ala
            420                 425                 430
Ala Arg Ser Ser Ser Ser Asp Asp Asn Gly Tyr Glu Ser Lys Phe
            435                 440                 445
Tyr Lys Lys Leu Lys Glu Val Gly Tyr Gln Asp Val Asp Lys Phe Leu
        450                 455                 460
Lys Ile Leu Asn Lys Glu Gly Ile Cys Gln Lys Gln Pro Gln Val Gly
465                 470                 475                 480
Asn Glu Lys Ala Asp Asn Val Asp Phe Thr Asn Glu Lys Tyr Val Lys
                485                 490                 495
Thr Phe Ser Arg Thr Glu Ile Cys Glu Pro Cys Pro Trp Cys Gly Leu
            500                 505                 510
Glu Lys Gly Gly Pro Pro Trp Lys Val Lys Gly Asp Lys Thr Cys Gly
        515                 520                 525
```

-continued

```
Ser Ala Lys Thr Lys Thr Tyr Asp Pro Lys Asn Ile Thr Asp Ile Pro
        530                 535                 540

Val Leu Tyr Pro Asp Lys Ser Gln Gln Asn Ile Leu Lys Lys Tyr Lys
545                 550                 555                 560

Asn Phe Cys Glu Lys Gly Ala Pro Gly Gly Gln Ile Lys Lys Trp
                565                 570                 575

Gln Cys Tyr Tyr Asp Glu His Arg Pro Ser Ser Lys Asn Asn Asn Asn
                580                 585                 590

Cys Val Glu Gly Thr Trp Asp Lys Phe Thr Gln Gly Lys Gln Thr Val
        595                 600                 605

Lys Ser Tyr Asn Val Phe Phe Trp Asp Trp Val His Asp Met Leu His
        610                 615                 620

Asp Ser Val Glu Trp Lys Thr Glu Leu Ser Lys Cys Ile Asn Asn Asn
625                 630                 635                 640

Thr Asn Gly Asn Thr Cys Arg Asn Asn Asn Lys Cys Lys Thr Asp Cys
                645                 650                 655

Gly Cys Phe Gln Lys Trp Val Glu Lys Lys Gln Gln Glu Trp Met Ala
                660                 665                 670

Ile Lys Asp His Phe Gly Lys Gln Thr Asp Ile Val Gln Gln Lys Gly
                675                 680                 685

Leu Ile Val Phe Ser Pro Tyr Gly Val Leu Asp Val Leu Lys Gly
        690                 695                 700

Gly Asn Leu Leu Gln Asn Ile Lys Asp Val His Gly Asp Thr Asp Asp
705                 710                 715                 720

Ile Lys His Ile Lys Lys Leu Leu Asp Glu Glu Asp Ala Val Ala Val
                725                 730                 735

Val Leu Gly Gly Lys Asp Asn Thr Thr Ile Asp Lys Leu Leu Gln His
                740                 745                 750

Glu Lys Glu Gln Ala Glu Gln Cys Lys Gln Lys Gln Glu Glu Cys Glu
                755                 760                 765

Lys Lys Ala Gln Gln Glu Ser Arg Gly Arg Ser Ala Glu Thr Arg Glu
        770                 775                 780

Asp Glu Arg Thr Gln Gln Pro Ala Asp Ser Ala Gly Glu Val Glu Glu
785                 790                 795                 800

Glu Glu Asp Asp Asp Tyr Asp Glu Asp Glu Asp Asp Val
                805                 810                 815

Val Gln Glu Glu Glu Gly Lys Glu Glu Gly Thr Val Thr Glu Val
        820                 825                 830

Thr Glu Val Thr Glu Val Val Glu Glu Thr Val Thr Glu Gln Glu Gly
                835                 840                 845

Val Lys Pro Cys Asp Ile Val Gly Lys Leu Phe Glu Asp Asp Lys Ser
        850                 855                 860

Leu Lys Glu Ala Cys Gly Leu Lys Tyr Gly Pro Gly Lys Glu Lys
865                 870                 875                 880

Phe Pro Asn Trp Lys Cys Val Thr Pro Ser Gly Val Ser Thr Ala Thr
                885                 890                 895

Ser Gly Lys Asp Gly Ala Ile Cys Val Pro Pro Arg Arg Arg Leu
                900                 905                 910

Tyr Val Gly Gly Leu Ser Gln Trp Ala Ser Arg Gly Gly Asp Glu Thr
                915                 920                 925

Thr Glu Val Ser Ser Glu Ala Thr Ser Ala Pro Ser Gln Ser Glu Ser
        930                 935                 940
```

```
Glu Lys Leu Arg Thr Ala Phe Ile Glu Ser Ala Ala Ile Glu Thr Phe
945                 950                 955                 960

Phe Leu Trp His Lys Tyr Lys Glu Glu Lys Lys Pro Pro Ala Thr Gln
            965                 970                 975

Asp Gly Ala Gly Leu Gly Val Ser Leu Pro Glu Pro Ser Pro Pro Gly
        980                 985                 990

Glu Asp Pro Gln Thr Gln Leu Gln Gln Thr Gly Val Ile Pro Pro Asp
    995                 1000                1005

Phe Leu Arg Gln Met Phe Tyr Thr Leu Ala Asp Tyr Lys Asp Ile Leu
1010                1015                1020

Tyr Ser Gly Ser Asn Asp Thr Ser Asp Thr Thr Gly Lys Gln Thr Pro
1025                1030                1035                1040

Ser Ser Ser Asn Asp Asn Leu Lys Asn Ile Val Leu Glu Ala Ser Gly
            1045                1050                1055

Ser Thr Glu Gln Glu Lys Glu Lys Met Lys Gln Ile Gln Ala Lys Ile
            1060                1065                1070

Lys Lys Ile Leu Asn Gly Ala Thr Ser Gly Val Pro Pro Val Thr Lys
            1075                1080                1085

Asn Ser Val Lys Thr Pro Gln Gln Thr Trp Trp Glu Asn Ile Ala Lys
            1090                1095                1100

Asp Ile Trp Asn Ala Met Val Cys Ala Leu Thr Tyr Lys Glu Asn Asp
1105                1110                1115                1120

Ala Arg Gly Thr Ser Ala Lys Ile Glu Gln Asn Lys Asp Leu Lys Lys
            1125                1130                1135

Ala Leu Trp Asp Glu Ala Asn Lys Asn Thr Pro Ile Glu Lys Tyr Gln
            1140                1145                1150

Tyr Thr Asn Val Lys Leu Glu Asp Glu Ser Gly Ala Lys Ser Asn Asp
            1155                1160                1165

Thr Ile Gln Pro Pro Thr Leu Lys Asn Phe Val Glu Ile Pro Thr Phe
            1170                1175                1180

Phe Arg Trp Leu His Glu Trp Gly Asn Ser Phe Cys Phe Glu Arg Ala
1185                1190                1195                1200

Lys Arg Leu Ala Gln Ile Lys His Glu Cys Met Asp Glu Asp Gly Glu
            1205                1210                1215

Lys Gln Tyr Ser Gly Asp Gly Leu Tyr Cys Glu Glu Ile Phe Ser Lys
            1220                1225                1230

Gln Tyr Asn Val Leu Gln Asp Leu Ser Ser Cys Ala Lys Pro Cys
            1235                1240                1245

Arg Leu Tyr Lys Thr Trp Ile Glu Lys Lys Thr Glu Tyr Glu Lys
            1250                1255                1260

Gln Gln Lys Ala Tyr Glu Gln Gln Lys Ser Asn Tyr Glu Asn Glu Gln
1265                1270                1275                1280

Lys Asp Lys Cys Gln Thr Gln Ser Asn Asn Ala Asn Glu Phe Ser
            1285                1290                1295

Arg Thr Leu Gly Ala Ser Pro Thr Ala Ala Glu Phe Leu Gln Lys Leu
            1300                1305                1310

Gly Ser Cys Lys Asn Asp Asn Gly Tyr Glu Asn Gly Glu Asp Asn Lys
            1315                1320                1325

Ile Asp Phe Lys Asn Pro Asp Lys Thr Phe Lys Glu Ala His Ser Cys
            1330                1335                1340

Asp Pro Cys Pro Ile Thr Gly Val Lys Cys Gln Asn Gly His Cys Val
1345                1350                1355                1360

Gly Ser Ala Asn Gly Lys Glu Cys Lys Asn Asn Lys Ile Thr Ala Glu
            1365                1370                1375
```

```
Asp Ile Lys Asn Lys Thr Asp Pro Asn Gly Asn Ile Glu Met Val Val
        1380                1385                1390

Ser Asp Asp Ser Thr Asn Thr Phe Glu His Leu Gly Asp Cys Lys Ser
        1395                1400                1405

Ser Gly Ile Phe Lys Gly Ile Arg Lys Asp Glu Trp Lys Cys Ala Asn
        1410                1415                1420

Val Cys Gly Val Asp Ile Cys Thr Leu Glu Lys Lys Ile Lys Asn Gly
1425                1430                1435                1440

Gln Glu Gly Asp Lys Lys Tyr Ile Thr Met Lys Glu Leu Leu Lys Arg
                1445                1450                1455

Trp Leu Glu Tyr Phe Leu Glu Asp Tyr Asn Arg Ile Arg Lys Lys Ile
        1460                1465                1470

Lys Leu Cys Thr Lys Lys Glu Asp Gly Cys Lys Cys Ile Lys Gly Cys
        1475                1480                1485

Ile Glu Lys Trp Val Gln Glu Lys Thr Lys Glu Trp Gln Lys Ile Asn
        1490                1495                1500

Asp Thr Tyr Leu Glu Gln Tyr Lys Asn Asp Asp Gly Asn Thr Leu Thr
1505                1510                1515                1520

Asn Phe Leu Glu Gln Phe Gln Tyr Arg Thr Glu Phe Lys Asn Ala Ile
        1525                1530                1535

Lys Pro Cys Asp Gly Leu Asp Gln Phe Lys Thr Ser Cys Gly Leu Asn
        1540                1545                1550

Ser Thr Asp Asn Ser Gln Asn Gly Asn Asn Asp Leu Val Leu Cys
        1555                1560                1565

Leu Leu Asn Lys Leu Gln Lys Lys Ile Ser Glu Cys Lys Glu Gln His
        1570                1575                1580

Ser Gly Gln Thr Gln Thr Pro Cys Asp Asn Ser Ser Leu Ser Gly Lys
1585                1590                1595                1600

Glu Ser Thr Leu Val Glu Asp Val Asp Asp Tyr Glu Glu Gln Asn Pro
        1605                1610                1615

Glu Asn Lys Val Glu Gln Pro Lys Phe Cys Pro Asp Met Lys Glu Pro
        1620                1625                1630

Lys Lys Glu Asn Asp Glu Glu Val Gly Thr Cys Gly Gly Asp Glu Glu
        1635                1640                1645

Lys Lys Lys Val Glu Asp Ser Val Ile Glu Gln Lys Glu Glu Ala
        1650                1655                1660

Ala Ser Ala Pro Glu Glu Ser Pro Leu Thr Pro Glu Ala Pro Lys
1665                1670                1675                1680

Lys Glu Glu Asn Val Val Pro Lys Pro Pro Pro Lys Lys Arg
        1685                1690                1695

Arg Ile Lys Thr Arg Asn Val Leu Asp His Pro Ala Val Ile Pro Ala
                1700                1705                1710

Leu Met Ser Ser Thr Ile Met Trp Ser Ile Gly Ile Gly Phe Ala Ala
        1715                1720                1725

Phe Thr Tyr Phe Tyr Leu Lys Lys Lys Thr Lys Ser Ser Val Gly Asn
        1730                1735                1740

Leu Phe Gln Ile Leu Gln Ile Pro Lys Ser Asp Tyr Asp Ile Pro Thr
1745                1750                1755                1760

Leu Lys Ser Ser Asn Arg Tyr Ile Pro Tyr Ala Ser Asp Arg His Lys
                1765                1770                1775

Gly Lys Thr Tyr Ile Tyr Met Glu Gly Asp Ser Ser Gly Asp Glu Lys
        1780                1785                1790
```

Tyr Ala Phe Met Ser Asp Thr Thr Asp Ile Thr Ser Ser Glu Ser Glu
            1795                1800                1805

Tyr Glu Glu Leu Asp Ile Asn Asp Ile Tyr Val Pro Gly Ser Pro Lys
1810                1815                1820

Tyr Lys Thr Leu Ile Glu Val Val Leu Glu Pro Ser Lys Arg Asp Thr
1825                1830                1835                1840

Gln Asn Asp Ile His Asn Asp Ile Pro Ser Asp Ile Pro Asn Ser Asp
            1845                1850                1855

Thr Pro Pro Pro Ile Thr Asp Asp Glu Trp Asn Gln Leu Lys Lys Asp
            1860                1865                1870

Phe Ile Ser Asn Met Leu Gln Asn Thr Gln Asn Thr Glu Pro Asn Ile
            1875                1880                1885

Leu His Asp Asn Val Asp Asn Asn Thr His Pro Thr Met Ser Arg His
            1890                1895                1900

Asn Met Asp Gln Lys Pro Phe Ile Met Ser Ile His Asp Arg Asn Leu
1905                1910                1915                1920

Phe Ser Gly Glu Glu Tyr Asn Tyr Asp Met Phe Asn Ser Gly Asn Asn
            1925                1930                1935

Pro Ile Asn Ile Ser Asp Ser Thr Asn Ser Met Asp Ser Leu Thr Ser
            1940                1945                1950

Asn Asn His Ser Pro Tyr Asn Asp Lys Asn Asp Leu Tyr Ser Gly Ile
            1955                1960                1965

Asp Leu Ile Asn Asp Ala Leu Ser Gly Asn His Ile Asp Ile Tyr Asp
            1970                1975                1980

Glu Met Leu Lys Arg Lys Glu Asn Glu Leu Phe Gly Thr Gln His His
1985                1990                1995                2000

Pro Lys Asn Ile Thr Ser Asn Arg Val Val Thr Gln Thr Ser Ser Asp
            2005                2010                2015

Asp Pro Ile Thr Asn Gln Ile Asn Leu Phe His Lys Trp Leu Asp Arg
            2020                2025                2030

His Arg Asp Met Cys Glu Lys Trp Lys Asn Asn His Glu Arg Leu Pro
            2035                2040                2045

Lys Leu Lys Glu Leu Trp Glu Asn Glu Thr His Ser Gly Asp Ile Asn
            2050                2055                2060

Ser Gly Ile Pro Ser Gly Asn His Val Leu Asn Thr Asp Val Ser Ile
2065                2070                2075                2080

Gln Ile Asp Met Asp Asn Pro Lys Thr Met Asn Glu Phe Thr Asn Met
            2085                2090                2095

Asp Thr Asn Pro Asp Lys Ser Thr Met Asp Thr Ile Leu Asp Asp Leu
            2100                2105                2110

Glu Lys Tyr Asn Glu Pro Tyr Tyr Tyr Asp Phe Tyr Lys His Asp Ile
            2115                2120                2125

Tyr Tyr Asp Val Asn Asp Asp Lys Ala Ser Glu Asp His Ile Asn Met
            2130                2135                2140

Asp His Asn Lys Met Asp Asn Asn Ser Asp Val Pro Thr Asn Val
2145                2150                2155                2160

Gln Ile Glu Met Asn Val Ile Asn Asn Gln Glu Leu Leu Gln Asn Glu
            2165                2170                2175

Tyr Pro Ile Ser His Met
            2180

(2) INFORMATION FOR SEQ ID NO:17:

(i) SEQUENCE CHARACTERISTICS:
        (A) LENGTH: 30 base pairs

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:17:

ATCGATCAGC TGGGAAGAAA TACTTCATCT                                              30

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:18:

ATCGATGGGC CCCGAAGTTT GTTCATTATT                                              30

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:19:

TCTCGTCAGC TGACGATCTC TAGTGCTATT                                              30

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:
```

(vi) ORIGINAL SOURCE:

(xi) SEQUENCE DESCRIPTION: SEQ ID NO:20:

ACGAGTGGGC CCTGTCACAA CTTCCTGAGT                                              30

(2) INFORMATION FOR SEQ ID NO:21:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

AGACCTCAAT TTCTAAG                                                            17

(2) INFORMATION FOR SEQ ID NO:22:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

AATCGCGAGC ATCATCTG                                                           18

(2) INFORMATION FOR SEQ ID NO:23:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

CCRAGRAGRC AARAAYTATG                                                         20

(2) INFORMATION FOR SEQ ID NO:24:

(i) SEQUENCE CHARACTERISTICS:

(A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

CCAWCKKARR AATTGWGG                                                            18

(2) INFORMATION FOR SEQ ID NO:25:

(i) SEQUENCE CHARACTERISTICS:
            (A) LENGTH: 291 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

Cys Xaa Xaa Xaa Xaa Xaa Xaa Xaa Xaa Xaa Xaa Xaa Cys Xaa Xaa
 1               5                  10                  15

Xaa Xaa Xaa Val Cys Ile Pro Asp Arg Arg Tyr Gln Leu Cys Met Lys
            20                  25                  30

Glu Leu Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Asp Phe Cys Lys Asp Ile Arg Trp Ser Leu Gly Asp Phe Gly Asp
                85                  90                  95

Ile Ile Met Gly Thr Asp Met Glu Gly Ile Gly Tyr Ser Lys Xaa Xaa
                100                 105                 110

Xaa Xaa Xaa Xaa Xaa Xaa Xaa Xaa Xaa Thr Asp Glu Lys Ala Gln Gln
            115                 120                 125

Arg Arg Lys Gln Trp Trp Asn Glu Ser Lys Ala Gln Ile Trp Thr Ala
    130                 135                 140

Met Met Tyr Ser Val Xaa Xaa Xaa Xaa Xaa Xaa Xaa Xaa Xaa Xaa Xaa
145                 150                 155                 160

Cys Xaa Xaa Xaa Xaa Xaa Xaa Xaa Xaa Glu Pro Gln Ile Tyr Arg Trp
                165                 170                 175

Ile Arg Glu Trp Gly Arg Asp Tyr Val Ser Glu Leu Pro Thr Glu Val
                180                 185                 190

Gln Lys Leu Lys Glu Lys Cys Xaa Xaa Xaa Xaa Xaa Xaa Xaa Xaa
                195                 200                 205

```
Xaa Xaa Cys Xaa Val Pro Pro Cys Gln Asn Ala Cys Lys Ser Tyr Asp
    210             215             220

Gln Trp Ile Thr Arg Lys Lys Asn Xaa Xaa Xaa Xaa Xaa Xaa Xaa Xaa
225                 230             235             240

Xaa Xaa Xaa Xaa Xaa Xaa Xaa Xaa Xaa Xaa Xaa Xaa Xaa Xaa Xaa Xaa
            245             250             255

Xaa Xaa Xaa Xaa Xaa Xaa Xaa Xaa Xaa Xaa Xaa Xaa Xaa Xaa Xaa Xaa
        260             265             270

Xaa Xaa Xaa Xaa Xaa Xaa Xaa Xaa Xaa Xaa Xaa Xaa Xaa Xaa Xaa Xaa
    275             280             285

Cys Xaa Cys
    290
```

(2) INFORMATION FOR SEQ ID NO:26:

(i) SEQUENCE CHARACTERISTICS:
        (A) LENGTH: 271 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:26:

```
Cys Xaa Xaa Xaa Xaa Xaa Xaa Xaa Xaa Xaa Cys Xaa Xaa Xaa Xaa Xaa
1               5               10              15

Xaa Xaa Xaa Xaa Val Cys Ile Pro Asp Arg Arg Ile Gln Leu Cys Ile
            20              25              30

Val Asn Leu Xaa Xaa Xaa Xaa Xaa Xaa Xaa Xaa Xaa Xaa Xaa Xaa Xaa
        35              40              45

Xaa Xaa Xaa Xaa Xaa Xaa Xaa Xaa Xaa Xaa Xaa Xaa Xaa Xaa Xaa Xaa
    50              55              60

Xaa Xaa Xaa Xaa Xaa Xaa Xaa Xaa Lys Phe Cys Asn Asp Leu Lys Asn
65                  70              75                  80

Ser Phe Leu Asp Tyr Gly His Leu Ala Met Gly Asn Asp Met Asp Phe
                85              90              95

Gly Gly Tyr Ser Thr Xaa Xaa Xaa Xaa Xaa Xaa Xaa Xaa Xaa Xaa Xaa
            100             105             110

Xaa Xaa Xaa Xaa Xaa Xaa Ser Glu His Lys Ile Lys Asn Phe Arg Lys
        115             120             125

Glu Trp Trp Asn Glu Phe Arg Glu Lys Leu Trp Glu Ala Met Leu Ser
130             135             140

Glu His Xaa Xaa Xaa Xaa Xaa Xaa Cys Xaa Xaa Xaa Xaa Xaa Xaa Glu
145             150             155             160

Leu Gln Ile Thr Gln Trp Ile Lys Glu Trp His Gly Glu Phe Leu Leu
                165             170             175

Glu Arg Asp Asn Arg Ser Lys Leu Pro Lys Ser Lys Cys Xaa Xaa Xaa
            180             185             190

Xaa Xaa Xaa Xaa Xaa Cys Xaa Glu Lys Glu Cys Ile Asp Pro Cys Met
        195             200             205

Lys Tyr Arg Asp Trp Ile Ile Arg Ser Lys Phe Xaa Xaa Xaa Xaa Xaa
210             215             220
```

```
Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Cys Xaa Xaa Xaa Xaa Xaa Xaa Xaa Cys Xaa Cys
        260                 265                 270
```

(2) INFORMATION FOR SEQ ID NO:27:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:27:

```
Cys Xaa Xaa Xaa Xaa Xaa Xaa Xaa Xaa Xaa Xaa Xaa Xaa Cys Xaa
1               5                   10                  15

Xaa Xaa Xaa Xaa Xaa Xaa Xaa Xaa Xaa Val Cys Val Pro Arg Arg
            20                  25                  30

Gln Glu Leu Cys Leu Gly Asn Ile Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Glu Val Cys Lys
65                  70                  75                  80

Ile Ile Asn Lys Thr Phe Ala Asp Ile Arg Asp Ile Ile Gly Gly Thr
                85                  90                  95

Asp Tyr Trp Asn Asp Leu Ser Asn Arg Xaa Xaa Xaa Xaa Xaa Xaa
            100                 105                 110

Xaa Xaa Xaa Xaa Xaa Xaa Xaa Asn Lys Lys Asn Asp Lys Leu Phe
            115                 120                 125

Arg Asp Glu Trp Trp Lys Val Ile Lys Lys Asp Val Trp Asn Val Ile
130                 135                 140

Ser Trp Phe Xaa Xaa Xaa Xaa Xaa Cys Xaa Xaa Xaa Xaa Xaa Xaa Xaa
145                 150                 155                 160

Ile Pro Gln Phe Phe Arg Trp Phe Ser Glu Trp Gly Asp Asp Tyr Cys
                165                 170                 175

Gln Asp Lys Thr Lys Met Ile Glu Thr Leu Lys Val Glu Cys Xaa Xaa
            180                 185                 190

Xaa Xaa Cys Xaa Asp Asp Asn Cys Lys Ser Lys Cys Asn Ser Tyr Lys
            195                 200                 205

Glu Trp Ile Ser Lys Lys Lys Xaa Xaa Xaa Xaa Xaa Xaa Xaa
            210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Cys Xaa Xaa Xaa
                245                 250                 255
```

Xaa Xaa Xaa Xaa Xaa Xaa Xaa Xaa Xaa Xaa Xaa Xaa Xaa Xaa
        260                 265                 270

Xaa Cys Xaa Xaa Cys
        275

(2) INFORMATION FOR SEQ ID NO:28:

(i) SEQUENCE CHARACTERISTICS:
      (A) LENGTH: 282 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:28:

Cys Xaa Xaa Xaa Xaa Xaa Xaa Xaa Xaa Xaa Xaa Cys Xaa Xaa
1               5                   10                  15

Xaa Xaa Xaa Xaa Xaa Xaa Xaa Xaa Xaa Val Cys Gly Pro Arg Arg
            20                  25                  30

Gln Gln Leu Cys Leu Gly Tyr Ile Xaa Xaa Xaa Xaa Xaa Xaa Xaa
            35                  40                  45

Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Lys Ile Cys Asn
65                  70                  75                  80

Ala Ile Leu Gly Ser Tyr Ala Asp Ile Gly Asp Ile Val Arg Gly Leu
                85                  90                  95

Asp Val Trp Arg Asp Ile Asn Thr Asn Xaa Xaa Xaa Xaa Xaa Xaa
            100                 105                 110

Xaa Xaa Xaa Xaa Xaa Xaa Xaa Xaa Xaa Lys Lys Gln Asn Asp Asn
            115                 120                 125

Asn Glu Arg Asn Lys Trp Trp Glu Lys Gln Arg Asn Leu Ile Trp Ser
130                 135                         140

Ser Met Val Lys His Ile Xaa Xaa Xaa Xaa Cys Xaa Xaa Xaa Xaa
145                 150                 155                 160

Xaa Xaa Xaa Xaa Ile Pro Gln Phe Leu Arg Trp Leu Lys Glu Trp Gly
                165                 170                 175

Asp Glu Phe Cys Glu Glu Met Gly Thr Glu Val Lys Gln Leu Glu Lys
            180                 185                 190

Ile Cys Xaa Xaa Xaa Xaa Cys Xaa Glu Lys Lys Cys Lys Asn Ala Cys
        195                 200                 205

Ser Ser Tyr Glu Lys Trp Ile Lys Glu Arg Lys Asn Xaa Xaa Xaa Xaa
210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa
            245                 250                 255

Xaa Xaa Cys Xaa Xaa Xaa Xaa Xaa Xaa Xaa Xaa Xaa Xaa Xaa
        260                 265                 270

Xaa Xaa Xaa Xaa Xaa Xaa Cys Xaa Xaa Cys
        275                 280

(2) INFORMATION FOR SEQ ID NO:29:

(i) SEQUENCE CHARACTERISTICS:
        (A) LENGTH: 324 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:29:

```
Cys Xaa Xaa Xaa Xaa Xaa Xaa Xaa Xaa Cys Xaa Xaa Xaa Xaa
 1               5                  10                  15

Xaa Xaa Xaa Xaa Xaa Xaa Xaa Ala Cys Ile Pro Pro Arg Arg Gln Lys
                20                  25                  30

Leu Cys Leu His Tyr Leu Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Asp Phe Lys Arg Gln Met Phe
                 85                  90                  95

Tyr Thr Phe Ala Asp Tyr Arg Asp Ile Cys Leu Gly Thr Asp Ile Ser
                100                 105                 110

Ser Lys Lys Asp Thr Ser Xaa Xaa Xaa Xaa Xaa Xaa Xaa Xaa
        115                 120                 125

Xaa Xaa Xaa Xaa Xaa Lys Ile Ser Asn Ser Ile Arg Tyr Arg Lys Ser
130                 135                 140

Trp Trp Glu Thr Asn Gly Pro Val Ile Trp Glu Gly Met Leu Cys Ala
145                 150                 155                 160

Leu Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Arg Pro Gln Phe Leu
                195                 200                 205

Arg Trp Leu Thr Glu Trp Gly Glu Asn Phe Cys Lys Glu Gln Lys Lys
210                 215                 220

Glu Tyr Lys Val Leu Leu Ala Lys Cys Xaa Xaa Xaa Xaa Xaa Xaa
225                 230                 235                 240

Xaa Xaa Xaa Xaa Cys Xaa Xaa Xaa Cys Val Ala Cys Lys Asp Gln Cys
                245                 250                 255

Lys Gln Tyr His Ser Trp Ile Gly Ile Trp Ile Asp Xaa Xaa Xaa
                260                 265                 270

Xaa Xaa Xaa Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
                290                 295                 300
```

```
Xaa Xaa Xaa Xaa Xaa Xaa Cys Xaa Xaa Xaa Xaa Xaa Xaa Xaa Cys
305                 310                 315                 320

Xaa Xaa Xaa Cys
```

(2) INFORMATION FOR SEQ ID NO:30:

(i) SEQUENCE CHARACTERISTICS:
        (A) LENGTH: 362 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:30:

```
Ala Cys Ala Pro Tyr Arg Arg Leu His Leu Cys Asp Tyr Asn Leu Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Gln Leu Cys Thr Val Leu
            50                  55                  60

Ala Arg Ser Phe Ala Asp Ile Gly Asp Ile Val Arg Gly Lys Asp Leu
65              70                  75                  80

Tyr Leu Gly Tyr Asp Asn Lys Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Lys Gly Gly Asp
            115                 120                 125

Phe Phe Gln Leu Arg Glu Asp Trp Trp Thr Ser Asn Arg Glu Thr Val
130                 135                 140

Trp Lys Ala Leu Ile Cys His Ala Xaa Xaa Xaa Xaa Xaa Xaa Xaa Xaa
145                 150                 155                 160

Xaa Xaa Xaa Cys Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Val Pro Gln Tyr Leu
            180                 185                 190

Arg Trp Phe Glu Glu Trp Ala Glu Asp Phe Cys Arg Lys Lys Lys
                195                 200                 205

Lys Leu Glu Asn Leu Gln Lys Gln Cys Xaa Xaa Xaa Xaa Xaa Cys
210                 215                 220

Xaa Xaa Xaa Xaa Xaa Xaa Xaa Xaa Xaa Xaa Xaa Xaa Xaa Xaa Cys
225                 230                 235                 240

Thr Asn Cys Ser Val Trp Cys Arg Met Tyr Glu Thr Trp Ile Asp Asn
                245                 250                 255

Gln Lys Lys Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
            275                 280                 285
```

```
Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Cys Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Cys Xaa Xaa Cys
            355                 360
```

(2) INFORMATION FOR SEQ ID NO:31:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:31:

```
Cys Xaa Xaa Xaa Xaa Xaa Xaa Xaa Xaa Xaa Xaa Xaa Xaa Xaa Xaa
1                   5                   10                  15

Cys Xaa Xaa Xaa Xaa Xaa Xaa Xaa Xaa Xaa Xaa Xaa Xaa Xaa Xaa
                20                  25                  30

Ala Cys Ala Pro Tyr Arg Arg Leu His Val Cys Asp Gln Asn Leu Xaa
        35                  40                  45

Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Gln Ile Cys Thr
                85                  90                  95

Met Leu Ala Arg Ser Phe Ala Asp Ile Gly Asp Ile Val Arg Gly Arg
                100                 105                 110

Asp Leu Tyr Leu Gly Asn Pro Gln Glu Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Asn Asp Pro Glu Phe Phe Lys Leu Arg
145                 150                 155                 160

Glu Asp Trp Trp Thr Ala Asn Arg Glu Thr Val Trp Lys Ala Ile Thr
                165                 170                 175

Cys Asn Ala Xaa Xaa Xaa Xaa Xaa Xaa Xaa Cys Xaa Xaa Xaa
            180                 185                 190

Xaa Xaa Xaa Xaa Xaa Xaa Xaa Xaa Xaa Xaa Xaa Xaa Xaa Xaa
            195                 200                 205

Xaa Xaa Xaa Xaa Val Pro Gln Tyr Leu Arg Trp Phe Glu Glu Trp Ala
210                 215                 220

Glu Asp Phe Cys Arg Lys Lys Asn Lys Lys Ile Lys Asp Val Lys Arg
225                 230                 235                 240
```

Asn Cys Xaa Xaa Xaa Xaa Xaa Xaa Xaa Xaa Xaa Xaa Cys Xaa
                245                 250                 255

Xaa Xaa Xaa Xaa Xaa Xaa Xaa Xaa Xaa Xaa Xaa Xaa Xaa Xaa
            260                 265                 270

Xaa Xaa Xaa Xaa Xaa Cys Ile Ser Cys Leu Tyr Ala Cys Asn Pro Tyr
        275                 280                 285

Val Asp Trp Ile Asn Asn Gln Lys Glu Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Cys Xaa
            355                 360                 365

Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Cys Xaa Xaa Cys
            405                 410

(2) INFORMATION FOR SEQ ID NO:32:

(i) SEQUENCE CHARACTERISTICS:
        (A) LENGTH: 411 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:32:

Cys Xaa Xaa Xaa Xaa Xaa Xaa Xaa Xaa Xaa Xaa Xaa Xaa Xaa Xaa
1               5                   10                  15

Xaa Xaa Cys Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Val Phe Leu Pro Pro Arg Arg Glu His Met Cys Thr Ser Asn
    50                  55                  60

Leu Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Ala Met Cys Arg Ala Val Arg Tyr
            115                 120                 125

```
Ser Phe Ala Asp Leu Gly Asp Ile Ile Arg Gly Arg Asp Met Trp Asp
        130                 135                 140

Glu Asp Lys Ser Ser Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Lys Lys Pro Ala Tyr Lys Lys Leu Arg Ala Asp
            180                 185                 190

Trp Trp Glu Ala Asn Arg His Gln Val Trp Arg Ala Met Lys Cys Ala
        195                 200                 205

Thr Xaa Xaa Xaa Xaa Cys Xaa Xaa Xaa Xaa Xaa Xaa Xaa Xaa Ile Pro
        210                 215                 220

Gln Arg Leu Arg Trp Met Thr Glu Trp Ala Glu Trp Tyr Cys Lys Ala
225                 230                 235                 240

Gln Ser Gln Glu Tyr Asp Lys Leu Lys Lys Ile Cys Xaa Xaa Xaa Xaa
                245                 250                 255

Xaa Xaa Xaa Xaa Xaa Xaa Xaa Cys Xaa Xaa Xaa Xaa Xaa Xaa Cys Gly
            260                 265                 270

Lys Cys Lys Ala Ala Cys Asp Lys Tyr Lys Glu Ile Glu Lys Trp
        275                 280                 285

Asn Glu Gln Trp Arg Lys Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Cys
        355                 360                 365

Xaa Xaa Xaa Xaa Xaa Xaa Xaa Cys Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Cys Xaa Xaa Cys
                405                 410
```

(2) INFORMATION FOR SEQ ID NO:33:

(i) SEQUENCE CHARACTERISTICS:
        (A) LENGTH: 311 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:33:

```
Cys Xaa Xaa Xaa Xaa Xaa Xaa Xaa Xaa Xaa Cys Xaa Xaa Xaa Xaa
1                   5                   10                  15

Xaa Xaa Xaa Xaa Xaa Ala Cys Met Pro Pro Arg Gln Lys Leu
            20                  25                  30
```

Cys Leu Tyr Tyr Ile Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Gln Phe Leu Arg Ser Met Met
                85                  90                  95

Tyr Thr Phe Gly Asp Tyr Arg Asp Ile Cys Leu Asn Thr Asp Ile Ser
                100                 105                 110

Lys Lys Gln Asn Asp Val Xaa Xaa Xaa Xaa Xaa Xaa Xaa Xaa
            115                 120                 125

Xaa Xaa Xaa Xaa Xaa Ser Lys Ser Pro Ser Gly Leu Ser Arg Gln Glu
 130                 135                 140

Trp Trp Lys Thr Asn Gly Pro Glu Ile Trp Lys Gly Met Leu Cys Ala
145                 150                 155                 160

Leu Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa
 180                 185                 190

Xaa Xaa Xaa Xaa Xaa Lys Pro Gln Phe Leu Arg Trp Met Ile Glu
 195                 200                 205

Trp Gly Glu Glu Phe Cys Ala Glu Arg Gln Lys Lys Glu Asn Ile Ile
210                 215                 220

Lys Asp Ala Cys Xaa Xaa Xaa Xaa Xaa Xaa Xaa Cys Xaa Xaa Xaa
225                 230                 235                 240

Lys His Arg Cys Asn Gln Ala Cys Arg Ala Tyr Gln Glu Tyr Val Glu
                245                 250                 255

Asn Lys Lys Lys Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa
 275                 280                 285

Xaa Xaa Xaa Xaa Xaa Xaa Xaa Xaa Xaa Xaa Xaa Xaa Xaa Cys
 290                 295                 300

Xaa Xaa Xaa Xaa Cys Xaa Cys
305                 310

(2) INFORMATION FOR SEQ ID NO:34:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:34:

Pro Arg Arg Gln Xaa Leu Cys
 1                   5

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:35:

CCRAGRAGRC AARAAYTATG        20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:36:

CCSMGSMGSC AGCAGYTSTG        20

(2) INFORMATION FOR SEQ ID NO:37:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:37:

Phe Ala Asp Xaa Xaa Asp Ile
1             5

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:38:

TTTGCWGATW WWSGWGATAT                                                             20

(2) INFORMATION FOR SEQ ID NO:39:

(i) SEQUENCE CHARACTERISTICS:
                 (A) LENGTH: 20 base pairs
                 (B) TYPE: nucleic acid
                 (C) STRANDEDNESS: single
                 (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:39:

TTCGCSGATW WCSGSGACAT                                                             20

(2) INFORMATION FOR SEQ ID NO:40:

(i) SEQUENCE CHARACTERISTICS:
                 (A) LENGTH: 6 amino acids
                 (B) TYPE: amino acid
                 (C) STRANDEDNESS: single
                 (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:40:

Pro Gln Phe Xaa Arg Trp
  1               5

(2) INFORMATION FOR SEQ ID NO:41:

(i) SEQUENCE CHARACTERISTICS:
                 (A) LENGTH: 18 base pairs
                 (B) TYPE: nucleic acid
                 (C) STRANDEDNESS: single
                 (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:41:

CCAWCKKARR AATTGWGG                                          18

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:42:

CCASCKGWAG AWCTGSGG                                          18

(2) INFORMATION FOR SEQ ID NO:43:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:43:

Glu Trp Gly Xaa Xaa Xaa Cys
 1               5

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:44:

CAAWAWTCWT CWCCCCATTC                                        20

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear -continued

```
    (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:45:

CAGWASTCST CSCCCCACTC                                              20
```

BINDING DOMAINS FROM PLASMODIUM VIVAX AND PLASMODIUM FALCIPARUM ERYTHROCYTE BINDING PROTEINS

This application is a continuation-in-part of U.S. application Ser. No. 08/119,667, filed Sep. 10, 1993. It also claims priority under 35 USC 119 from PCT Application No. PCT/US94/10230 filed Sep. 7, 1994.

BACKGROUND OF THE INVENTION

Malaria infects 200–400 million people each year causing 1–2 million deaths, thus remaining one of the most important infectious diseases in the world. Approximately 25 percent of all deaths of children in rural Africa between the ages of one and four years are caused by malaria. Due to the importance of the disease as a worldwide health problem, considerable effort is being expended to identify and develop malaria vaccines.

Malaria in humans is caused by four species of the parasite Plasmodium: *P. falciparum, P. vivax, P. knowlesi* and *P. malariae*. The major cause of malaria in humans is *P. falciparum* which infects 200 million to 400 million people every year, killing 1 to 4 million.

Duffy Antigen Binding Protein (DABP) and Sialic Acid Binding Protein (SABP) are soluble proteins that appear in the culture supernatant after infected erythrocytes release merozoites. Immunochemical data indicate that DABP and SABP which are the respective ligands for the *P. vivax* and *P. falciparum* Duffy and sialic acid receptors on erythrocytes, possess specificities of binding which are identical either in soluble or membrane bound form.

DABP is a 135 kDa protein which binds specifically to Duffy blood group determinants (Wertheimer et al., Exp. Parasitol. 69: 340–350 (1989); Barnwell, et al., J. Exp. Med. 169: 1795–1802 (1989)). Thus, binding of DABP is specific to human Duffy positive erythrocytes. There are four major Duffy phenotypes for human erythrocytes: Fy(a), Fy(b), Fy(ab) and Fy(negative), as defined by the anti-Fy$^a$ and anti-Fy$^b$ sera (Hadley et al., In Red Cell Antigens and Antibodies, G. Garratty, ed. (Arlington, Va.:American Association of Blood Banks) pp. 17–33 (1986)). DABP binds equally to both Fy(a) and Fy(b) erythrocytes which are equally susceptible to invasion by *P. vivax;* but not to Fy(negative) erythrocytes.

In the case of SABP, a 175 kDa protein, binding is specific to the glycophorin sialic acid residues on erythrocytes (Camus and Hadley, Science 230:553–556 (1985); Orlandi, et al., J. Cell Biol. 116:901–909 (1992)). Thus, neuraminidase treatment (which cleaves off sialic acid residues) render erythrocytes immune to *P. falciparum* invasion.

The specificities of binding and correlation to invasion by the parasite thus indicate that DABP and SABP are the proteins of *P. vivax* and *P. falciparum* which interact with sialic acids and the Duffy antigen on the erythrocyte. The genes encoding both proteins have been cloned and the DNA and predicted protein sequences have been determined (B. Kim Lee Sim, et al., J. Cell Biol. 111: 1877–1884 (1990); Fang, X., et al., Mol. Biochem Parasitol. 44: 125–132 (1991)).

Despite considerable research efforts worldwide, because of the complexity of the Plasmodium parasite and its interaction with its host, it has not been possible to discover a satisfactory solution for prevention or abatement of the blood stage of malaria. Because malaria is a such a large worldwide health problem, there is a need for methods that abate the impact of this disease. The present invention provides effective preventive and therapeutic measures against Plasmodium invasion.

SUMMARY OF THE INVENTION

The present invention provides compositions comprising an isolated DABP binding domain polypeptides and/or isolated SABP binding domain polypeptides. The DABP binding domain polypeptides preferably comprise between about 200 and about 300 amino acid residues while the SABP binding domain polypeptides preferably comprises between about 200 and about 600 amino acid residues. A preferred DABP binding domain polypeptide has residues 1 to about 325 of the amino acid sequence found in SEQ ID No. 2. A preferred SABP binding domain polypeptide has residues 1 to about 616 of the amino acid sequence of SEQ ID No. 4.

The present invention also includes pharmaceutical compositions comprising a pharmaceutically acceptable carrier and an isolated DABP binding domain polypeptide in an amount sufficient to induce a protective immune response to *Plasmodium vivax* merozoites in an organism. In addition, isolated SABP binding domain polypeptide in an amount sufficient to induce a protective immune response to *Plasmodium falciparum* may be added to the pharmaceutical composition.

Also provided are pharmaceutical compositions comprising a pharmaceutically acceptable carrier and an isolated SABP binding domain polypeptide in an amount sufficient to induce a protective immune response to *Plasmodium falciparum* merozoites in an organism. In addition, isolated DABP binding domain polypeptide in an amount sufficient to induce a protective immune response to *Plasmodium vivax* may be added to the pharmaceutical composition.

Isolated polynucleotides which encode a DABP binding domain polypeptides or SABP binding domain polypeptides are also disclosed. In addition, the present invention includes a recombinant cell comprising the polynucleotide encoding the DABP binding domain polypeptide.

The current invention further includes methods of inducing a protective immune response to Plasmodium merozoites in a patient. The methods comprise administering to the patient an immunologically effective amount of a pharmaceutical composition comprising a pharmaceutically acceptable carrier and an isolated DABP binding domain polypeptide, an SABP binding domain polypeptide or a combination thereof.

The present disclosure also provides DNA sequences from additional *P. falciparum* genes in the Duffy-binding like (DBL) family that have regions conserved with the *P. falciparum* 175 kD and *P. vivax* 135 kD binding proteins.

DEFINITIONS

As used herein a "DABP binding domain polypeptide" or a "SABP binding domain polypeptide" are polypeptides substantially identical (as defined below) to a sequence from the cysteine-rich, amino-terminal region of the Duffy antigen binding protein (DABP) or sialic acid binding protein (SABP), respectively. Such polypeptides are capable of binding either the Duffy antigen or sialic acid residues on glycophorin. In particular, DABP binding domain polypeptides consist of amino acid residues substantially similar to a sequence of SABP within a binding domain from the N-terminal amino acid (residue 1) to about residue 325. SABP binding domain polypeptides consist of residues substantially similar to a sequence of DABP within a binding domain from the N-terminal amino acid (residue 1) to about residue 325.

The binding domain polypeptides encoded by the genes of the DBL family consist of those residues substantially identical to the sequence of the binding domains of DABP and SABP as defined above. The DBL family comprises sequences with substantial similarity to the conserved regions of the DABP and SABP. These include those sequences reported here as ebl-1 (SEQ ID NO:5 and SEQ ID NO:6), (SEQ ID NO:7 and SEQ ID NO:6), var-7 (SEQ ID NO:13 and SEQ ID NO:14), GenBank Accession No. L42636) and var-1 (SEQ ID NO:15 and SEQ ID NO:16, GenBank Accession No. L40608). The sequence ebl-2, (SEQ ID NO:9 and SEQ ID NO:10) represents the binding domains of var-7, and Proj3 (SEQ ID NO:11 and SEQ ID NO:12) is the binding domain of var-1. The DBL family also includes two other members var-2 and var-3 (GenBank Accession No. L40609).

The polypeptides of the invention can consist of the full length binding domain or a fragment thereof. Typically DABP binding domain polypeptides will consist of from about 50 to about 325 residues, preferably between about 75 and 300, more preferably between about 100 and about 250 residues. SABP binding domain polypeptides will consist of from about 50 to about 616 residues, preferably between about 75 and 300, more preferably between about 100 and about 250 residues.

Particularly preferred polypeptides of the invention are those within the binding domain that are conserved between SABP and the DBL family. Residues within these conserved domains are shown in FIG. 1, below.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The term "substantial identity" means that a polypeptide comprises a sequence that has at least 80% sequence identity, preferably 90%, more preferably 95% or more, compared to a reference sequence over a comparison window of about 20 residues to about 600 residues—typically about 50 to about 500 residues usually about 250 to 300 residues. The values of percent identity are determined using the programs above. Particularly preferred peptides of the present invention comprise a sequence in which at least 70% of the cysteine residues conserved in DABP and SABP are present. Additionally, the peptide will comprise a sequence in which at least 50% of the tryptophan residues conserved in DABP and SABP are present. The term substantial similarity is also specifically defined here with respect to those amino acid residues found to be conserved between DABP, SABP and the sequences of the DBL family. These conserved amino acids consist prominently of tryptophan and cysteine residues conserved among all sequences reported here. In addition the conserved amino acid residues include phenylalanine residues which may be substituted with tyrosine. These amino acid residues may be determined to be conserved after the sequences have been aligned using methods outlined above by someone skilled in the art.

Another indication that polypeptide sequences are substantially identical is if one protein is immunologically reactive with antibodies raised against the other protein. Thus, the polypeptides of the invention include polypeptides immunologically reactive with antibodies raised against the SABP binding domain, the DABP binding domain or raised against the conserved regions of the DBL family.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

Nucleotide sequences are also substaintially identical for purposes of this application when the polypeptides which they encode are substantially identical. Thus, where one nucleic acid sequence encodes essentially the same polypeptide as a second nucleic acid sequence, the two nucleic acid sequences are substantially identical, even if they would not hybridize under stringent conditions due to silent substitutions permitted by the genetic code (see, Darnell et al. (1990) *Molecular Cell Biology,* Second Edition *Scientific American Books* W. H. Freeman and Company New York for an explanation of codon degeneracy and the genetic code).

The phrases "isolated" or "biologically pure" refer to material which is substantially or essentially free from components which normally accompany it as found in its native state. Thus, the binding domain polypeptides of this invention do not contain materials normally associated with their in situ environment, e.g., other proteins from a merozoite membrane. Typically, isolated proteins of the invention are at least about 80% pure, usually at least about 90%, and preferrably at least about 95% as measured by band intensity on a silver stained gel.

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

BRIEF DESCRIPTION OF THE DRAWINGS

FIG. 3 shows primers useful for isolating sequences encoding the conserved motifs of the invention.

DESCRIPTION OF THE PREFERRED EMBODIMENT

Figure 1:
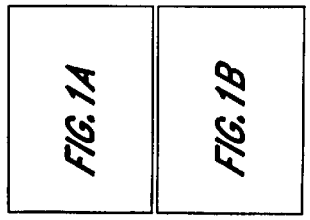
FIG. 1 represents an alignment of the predicted amino acid sequences of the DABP binding domain (Vivax) (SEQ ID NO:25), the two homologous SABP domains (SABP F1 (SEQ ID NO:26) and SABP F2 (SEQ ID NO:27)) and the sequenced members of the DBL gene family (ebl-1 (SEQ ID NO:28), E31a (SEQ ID NO:29), EBL-2 (SEQ ID NO:30) and the three homologous Proj3 domains: F1 (SEQ ID NO:31), F2 (SEQ ID NO:32) and F3 (SEQ ID NO:33).

The binding of merozoites and schizonts to erythrocytes is mediated by specific binding proteins on the surface of the merozoite or schizont and is necessary for erythrocyte invasion. In the case of *P. falciparum*, this binding involves specific interaction between sialic acid glycophorin residues on the erythrocyte and the sialic acid binding protein (SABP) on the surface of the merozoite or schizont. The ability of purified SABP to bind erythrocytes with chemically or enzymatically altered sialic acid residues paralleled the ability of *P. falciparum* to invade these erythrocytes. Furthermore, sialic acid deficient erythrocytes neither bind SABP nor support invasion by *P. falciparum*. The DNA encoding SABP from *P. falciparum* has also been cloned and sequenced.

In *P. vivax*, specific binding to the erythrocytes involves interaction between the Duffy blood group antigen on the erythrocyte and the Duffy antigen binding protein (DABP) on the merozoite. Duffy binding proteins were defined biologically as those soluble proteins that appear in the culture supernatant after the infected erythrocytes release merozoites which bind to human Duffy positive, but not to human Duffy negative erythrocytes. It has been shown that binding of the *P. vivax* DABP protein to Duffy positive erythrocytes is blocked by antisera to the Duffy blood group determinants. Purified Duffy blood group antigens also block the binding to erythrocytes. DABP has also been shown to bind Duffy blood group determinants on Western blots.

Duffy positive blood group determinants on human erythrocytes are essential for invasion of human erythrocytes by *Plasmodium vivax*. Both attachment and reorientation of *P. vivax* merozoites occur equally well on Duffy positive and negative erythrocytes. A junction then forms between the apical end of the merozoite and the Duffy-positive erythrocyte, followed by vacuole formation and entry of the merozoite into the vacuole. Junction formation and merozoite entry into the erythrocyte do not occur on Duffy negative cells, suggesting that the receptor specific for the Duffy determinant is involved in apical junction formation but not initial attachment. The DNA sequences encoding the DABP from *P. vivax* and *P. knowlesi* have been cloned and sequenced.

*P. vivax* red cell invasion has an absolute requirement for the Duffy blood group antigen. Isolates of *P. falciparum*, however, vary in their dependency on sialic acid for invasion. Certain *P. falciparum* clones have been developed which invade sialic acid deficient erythrocytes at normal rates. This suggests that certain strains of *P. falciparum* can interact with other ligands on the erythrocyte and so may possess multiple erythrocyte binding proteins with differing specificities.

A basis for the present invention is the discovery of the binding domains in both DABP and SABP. Comparison of the predicted protein sequences of DABP and SABP reveals an amino-terminal, cysteine-rich region in both proteins with a high degree of similarity between the two proteins. The amino-terminal, cysteine-rich region of DABP contains about 325 amino acids, whereas the amino-terminal, cysteine-rich region of SABP contains about 616 amino acids. This is due to an apparent duplication of the amino-terminal, cysteine-rich region in the SABP protein. The cysteine residues are conserved between the two regions of SABP and DABP, as are the amino acids surrounding the cysteine residues and a number of aromatic amino acid residues in this region. The amino-terminal cysteine rich region and another cysteine-rich region near the carboxyl-terminus show the most similarity between the DABP and SABP proteins. The region of the amino acid sequence between these two cysteine-rich regions show only limited similarity between DABP and SABP.

Other *P. falciparum* open reading frames and genes with regions that have substantial identity to binding domains of SABP and DABP have been identified. Multiple copies of these sequences exist in the parasite genome, indicating their important activity in host-parasite interactions. A family of these sequences (the DBL family) have been cloned from chromosome 7 subsegment libraries that were constructed during genetic studies of the chloroquine resistance locus (Wellems et. al., *PNAS* 88: 3382–3386 (1991)). Certain of these transcripts are known to be from the var family of genes that modulate cytoadherence and antigenic variation of *P. falciparum*-infected erythrocytes (see, Example 3, below).

Genes of the *P. falciparum* var family encode 200–350 kD variant surface molecules that determine antigenic and adhesive properties of parasitized erythrocytes. The large repertoire of var genes (50–150 copies, having sufficient DNA to account for 2–6% of the haploid genome), the dramatic sequence variation among the gene copies, their variable expression in different parasite lines, the ready detection of DNA rearrangements, and the receptor binding features of the encoded extracellular domains all implicate var genes as the major determinants of antigenic variation and cytoadherence in *P. falciparum* malaria.

A second class of DBL-encoding transcripts includes single-copy genes such as ebl-1. Genetic linkage studies have placed this gene within a region of chromosome 13 that affects invasion of malarial parasites in human red blood cells (Wellems et al., *Cell* 49:633–642 (1987)). Both SABP and ebl-1 show restriction patterns that are well conserved among different parasite isolates. This conservation of gene structure and the sequence relationships between the ebl-1 and SABP domains suggest that ebl-1 encodes a novel erythrocyte binding molecule having receptor properties distinct from those of SABP.

Southern hybridization experiments using probes from these open reading frames have indicated that additional copies of these conserved sequences are located elsewhere in the genome. The largest of the open reading frames on chromosome 7 is 8 kilobases and contains four tandem repeats homologous to the N-terminal, cysteine-rich unit of SABP and DABP.

FIG. 1 represents an alignment of the DBL family with the DABP binding domain and two homologous regions of SABP ($F_1$ and $F_2$). The DBL family is divided into two sub-families to achieve optimal alignment. Conserved cysteine residues are shown in bold face and conserved aromatic residues are underlined.

The polypeptides of the invention can be used to raise monoclonal antibodies specific for the binding domains of SABP, DABP or the conserved regions in the DBL gene family. The antibodies can be used for diagnosis of malarial infection or as therapeutic agents to inhibit binding of merozoites to erythrocytes. The production of monoclonal antibodies against a desired antigen is well known to those of skill in the art and is not reviewed in detail here.

The multitude of techniques available to those skilled in the art for production and manipulation of various immunoglobulin molecules can thus be readily applied to inhibit binding. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and F(ab)$_2$, as well as in single chains. For a general review of immunoglobulin structure and function see, *Fundamental Immunology*, 2d Ed., W. E. Paul ed., Ravens Press, N.Y., (1989).

Antibodies which bind polypeptides of the invention may be produced by a variety of means. The production of non-human monoclonal antibodies, e.g., murine, lagomorpha, equine, etc., is well known and may be accomplished by, for example, immunizing the animal with a preparation containing the polypeptide. Antibody-producing cells obtained from the immunized animals are immortalized and screened, or screened first for the production of antibody which inhibits binding between and meroxoites and erythrocytes and then immortalized. For a discussion of general procedures of monoclonal antibody production see Harlow and Lane, *Antibodies, A Laboratory Manual* Cold Spring Harbor Publications, N.Y. (1988).

Thus, the present invention allows targeting of protective immune responses or monoclonal antibodies to sequences in the binding domains that are conserved between SABP, DABP and encoded regions of the DBL family. Identification of the binding regions of these proteins facilitates vaccine development because it allows for a focus of effort upon the functional elements of the large molecules. The particular sequences within the binding regions refine the target to critical regions that have been conserved during evolution, and are thus preferred for use as vaccines against the parasite.

The genes of the DBL family (which have not previously been sequenced) can be used as markers to detect the presence of the *P. falciparum* parasite in patients. This can be accomplished by means well known to practitioners in the art using tissue or blood from symptomatic patients in PCR reactions with oligonucleotides complementary to portions of the genes of the DBL family. Furthermore, sequencing the DBL family provides a means for skilled practitioners to generate defined probes to be used as genetic markers in a variety of applications.

Additionally, the present invention defines a conserved motif present in, but not restricted to other members of the subphylum Apicomplexa which participates in host parasite interaction. This motif can be identified in Plasmodium species and other parasitic protozoa by the polymerase chain reaction using the synthetic oligonucleotide primers shown in FIG. 3. PCR methods are described in detail below. These primers are designed from regions in the conserved motif showing the highest degree of conservation among DABP, SABP and the DBL family. FIG. 3 shows these regions and the consensus amino acid sequences derived from them.

A. General Methods

Much of the nomenclature and general laboratory procedures required in this application can be found in Sambrook, et al., Molecular Cloning *A Laboratory Manual* (2nd Ed.), Vol. 1–3, Cold Spring Harbor Laboratory, Cold Spring Harbor, N.Y., 1989. The manual is hereinafter referred to as "Sambrook, et al."

The practice of this invention involves the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel).

Examples of techniques sufficient to direct persons of skill through in vitro amplification methods, including the polymerase chain reaction (PCR) the ligase chain reaction (LCR), Q,β-replicase amplification and other RNA polymerase mediated techniques are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

The culture of cells used in the present invention, including cell lines and cultured cells from tissue or blood samples is well known in the art. Freshney (*Culture of Animal Cells, a Manual of Basic Technique*, third edition Wiley-Liss, New York (1994)) and the references cited therein provides a general guide to the culture of cells.

DBL genes are optionally bound by antibodies in one of the embodiments of the present invention. Methods of producing polyclonal and monoclonal antibodies are known to those of skill in the art. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) Nature 256: 495–497. Other suitable techniques for antibody preparation include selection of libraries of recombinant antibodies in phage or similar vectors. See, Huse et al. (1989) *Science* 246: 1275–1281; and Ward, et al. (1989) *Nature* 341: 544–546. Specific Monoclonal and polyclonal antibodies will usually bind with a KD of at least about 0.1 mM, more usually at least about 1 $\mu$M, and most preferably at least about 0.1 $\mu$M or better.

B. Methods for Isolating DNA Encoding SABP, DABP and DBL Binding Regions

The nucleic acid compositions of this invention, whether RNA, cDNA, genomic DNA, or a hybrid of the various combinations, may be isolated from natural sources or may be synthesized in vitro. The nucleic acids claimed may be present in transformed or transfected whole cells, in a transformed or transfected cell lysate, or in a partially purified or substantially pure form.

Techniques for nucleic acid manipulation of genes encoding the binding domains of the invention, such as subcloning nucleic acid sequences encoding polypeptides into expression vectors, labelling probes, DNA hybridization, and the like are described generally in Sambrook et al.

Recombinant DNA techniques can be used to produce the binding domain polypeptides. In general, the DNA encoding the SABP and DABP binding domains are first cloned or isolated in a form suitable for ligation into an expression vector. After ligation, the vectors containing the DNA fragments or inserts are introduced into a suitable host cell for expression of the recombinant binding domains. The polypeptides are then isolated from the host cells.

There are various methods of isolating the DNA sequences encoding the SABP, DABP and DBL binding domains. Typically, the DNA is isolated from a genomic or cDNA library using labelled oligonucleotide probes specific for sequences in the DNA. Restriction endonuclease digestion of genomic DNA or cDNA containing the appropriate genes can be used to isolate the DNA encoding the binding domains of these proteins. Since the DNA sequences of the SABP and DABP genes are known, a panel of restriction endonucleases can be constructed to give cleavage of the DNA in the desired regions. After restriction endonuclease digestion, DNA encoding SABP binding domain or DABP binding domain is identified by its ability to hybridize with nucleic acid probes, for example on Southern blots, and these DNA regions are isolated by standard methods familiar to those of skill in the art. See Sambrook, et al.

The polymerase chain reaction can also be used to prepare DABP, SABP DBL binding domain DNA. Polymerase chain reaction technology (PCR) is used to amplify nucleic acid sequences of the DABP and SABP binding domains directly from mRNA, from cDNA, and from genomic libraries or cDNA libraries. The primers shown in FIG. 3 are particularly preferred for this process.

Appropriate primers and probes for amplifying the SABP and DABP binding region DNA's are generated from analysis of the DNA sequences. In brief, oligonucleotide primers complementary to the two 3' borders of the DNA region to be amplified are synthesized. The polymerase chain reaction is then carried out using the two primers. See *PCR Protocols: A Guide to Methods and Applications*. Innis, M, Gelfand, D., Sninsky, J. and White, T., eds.), Academic Press, San Diego (1990). Primers can be selected to amplify the entire DABP regions or to amplify smaller segments of the DABP and SABP binding domains, as desired.

Oligonucleotides for use as probes are chemically synthesized according to the solid phase phosphoramidite triester method first described by Beaucage, S. L. and Caruthers, M. H., 1981, Tetrahedron Letts., 22(20):1859–1862 using an automated synthesizer, as described in Needham-VanDevanter, D. R., et al. 1984, Nucleic Acids Res., 12:6159–6168. Purification of oligonucleotides is by either native acrylamide gel electrophoresis or by anion-exchange HPLC as described in Pearson, J. D. and Regnier, F. E., 1983, J. Chrom., 255:137–149.

The sequence of the synthetic oligonucleotides can be verified using the chemical degradation method of Maxam, A. M. and Gilbert, 1980, in W., Grossman, L. and Moldave, D., eds. Academic Press, New York, Methods in Enzymology, 65:499–560.

Other methods known to those of skill in the art may also be used to isolate DNA encoding all or part of the SABP or DABP binding domains. See Sambrook, et al.

C. Expression of DABP SABP and DBL Binding Domain Polypeptides

Once binding domain DNAs are isolated and cloned, one may express the desired polypeptides in a recombinantly engineered cell such as bacteria, yeast, insect (especially employing baculoviral vectors), and mammalian cells. It is expected that those of skill in the art are knowledgeable in the numerous expression systems available for expression of the DNA encoding the DABP and SABP binding domains. No attempt to describe in detail the various methods known for the expression of proteins in prokaryotes or eukaryotes will be made.

In brief summary, the expression of natural or synthetic nucleic acids encoding binding domains will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the binding domains. To obtain high level expression of a cloned gene, it is desirable to construct expression plasmids which contain, at the minimum, a strong promoter to direct transcription, a ribosome binding site for translational initiation, and a transcription/translation terminator.

1. Expression in Prokaryotes

Examples of regulatory regions suitable for this purpose in *E. coli* are the promoter and operator region of the *E. coli* tryptophan biosynthetic pathway as described by Yanofsky, C., 1984, J. Bacteriol., 158:1018–1024 and the leftward promoter of phage lambda ($P_L$) as described by Herskowitz, I. and Hagen, D., 1980, Ann. Rev. Genet., 14:399–445. The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA.

Expression systems for expressing the DABP and SABP binding domains are available using *E. coli,* Bacillus sp. (Palva, I et al., 1983, Gene 22:229–235; Mosbach, K. et al. Nature, 302:543–545 and Salmonella. *E. coli* systems are preferred.

The binding domain polypeptides produced by prokaryote cells may not necessarily fold properly. During purification from *E. coli,* the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

Detection of the expressed antigen is achieved by methods known in the art as radioimmunoassays, Western blotting techniques or immunoprecipitation. Purification from *E. coli* can be achieved following procedures described in U.S. Pat. No. 4,511,503.

2. Synthesis of SABP, DABP and DBL Binding Domains in Eukaryotes

A variety of eukaryotic expression systems such as yeast, insect cell lines and mammalian cells, are known to those of skill in the art. As explained briefly below, the DABP and SABP binding domains may also be expressed in these eukaryotic systems.

a. Expression in Yeast

Synthesis of heterologous proteins in yeast is well known and described. *Methods in Yeast Genetics,* Sherman, F., et al., Cold Spring Harbor Laboratory, (1982) is a well recognized work describing the various methods available to produce the binding domains in yeast.

Examples of promoters for use in yeast include GAL1,10 (Johnson, M., and Davies, R. W., 1984, Mol. and Cell. Biol., 4:1440–1448) ADH2 (Russell, D., et al. 1983, J. Biol. Chem., 258:2674–2682), PH05 (EMBO J. 6:675–680, 1982), and MFα1 (Herskowitz, I. and Oshima, Y., 1982, in The Molecular Biology of the Yeast Saccharomyces, (eds. Strathern, J. N. Jones, E. W., and Broach, J. R., Cold Spring Harbor Lab., Cold Spring Harbor, N.Y., pp. 181–209. A multicopy plasmid with a selective marker such as Leu-2, URA-3, Trp-1, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17–24; Broach, et al., 1979, Gene, 8:121–133).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, 1978, Nature (London), 275:104–109; and Hinnen, A., et al., 1978, Proc. Natl. Acad. Sci. USA, 75:1929–1933. The second procedure does not involve removal of the cell wall. Instead the cells are treated with lithium chloride or acetate and PEG and put on selective plates (Ito, H., et al., 1983, J. Bact., 153:163–168).

The binding domains can be isolated from yeast by lysing the cells and applying standard protein isolation techniques to the lysates. The monitoring of the purification process can be accomplished by using Western blot techniques or radio-immunoassays of other standard immunoassay techniques.

b. Expression in Mammalian and Insect Cell Cultures

Illustrative of cell cultures useful for the production of the binding domains are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

As indicated above, the vector, e.g., a plasmid, which is used to transform the host cell, preferably contains DNA sequences to initiate transcription and sequences to control the translation of the antigen gene sequence. These sequences are referred to as expression control sequences. When the host cell is of insect or mammalian origin illustrative expression control sequences are obtained from the SV40 promoter (Science, 222:524–527, 1983), the CMV I.E. Promoter (Proc. Natl. Acad. Sci. 81:659–663, 1984) or the metallothionein promoter (Nature 296:39–42, 1982). The cloning vector containing the expression control sequences is cleaved using restriction enzymes and adjusted in size as necessary or desirable and ligated with DNA coding for the SABP or DABP polypeptides by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VPl intron from SV40 (Sprague, 3. et al., 1983, J. Virol. 45: 773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed DABP and SABP binding domain polypeptides are isolated from cells grown as suspensions or as monolayers. The latter are recovered by well known mechanical, chemical or enzymatic means.

c. Expression in Recombinant Vaccinia Virus- or Adenovirus-infected Cells

In addition to use in recombinant expression systems, the isolated binding domain DNA sequences can also be used to transform viruses that transfect host cells in the patient. Live attenuated viruses, such as vaccinia or adenovirus, are convenient alternatives for vaccines because they are inexpensive to produce and are easily transported and administered. Vaccinia vectors and methods useful in immunization protocols are described, for example, in U.S. Pat. No. 4,722,848, incorporated herein by reference.

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the DNA's encoding the DABP and SABP binding domain polypeptides into plasmids so that they are flanked by viral sequences on both sides. The DNA's encoding the binding domains are then inserted into the virus genome through homologous recombination.

A recombinant adenovirus can be produced, for example, by ligating together two plasmids each containing about 50% of the viral sequence and the DNA sequence encoding erythrocyte binding domain polypeptide. Recombinant RNA viruses such as the alpha virus can be made via a cDNA intermediate using methods known in the art.

In the case of vaccinia virus (for example, strain WR), the DNA sequence encoding the binding domains can be inserted in the genome by a number of methods including homologous recombination using a transfer vector, pTKgpt-OFIS as described in Kaslow, et al., *Science* 252:1310–1313 (1991), which is incorporated herein by reference.

Alternately the DNA encoding the SABP and DABP binding domains may be inserted into another plasmid designed for producing recombinant vaccinia, such as pGS62, Langford, C. L., et al., 1986, *Mol. Cell. Biol.* 6:3191–3199. This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding the DABP and SABP binding domain polypeptides and by immunodetection techniques using antibodies specific for the expressed binding domain polypeptides. Virus stocks may be prepared by infection of cells such as HELA S3 spinner cells and harvesting of virus progeny.

The recombinant virus of the present invention can be used to induce anti-SABP and anti-DABP binding domain antibodies in mammals, such as mice or humans. In addition, the recombinant virus can be used to produce the SABP and DABP binding domains by infecting host cells in vitro, which in turn express the polypeptide (see section on expression of SABP and DABP binding domains in eukaryotic cells, above).

The present invention also relates to host cells infected with the recombinant virus. The host cells of the present invention are preferably mammalian, such as BSC-1 cells. Host cells infected with the recombinant virus express the DABP and SABP binding domains on their cell surfaces. In addition, membrane extracts of the infected cells induce protective antibodies when used to inoculate or boost previously inoculated mammals.

D. Purification of the SABP, DABP and DBL Binding Domain Polypeptides

The binding domain polypeptides produced by recombinant DNA technology may be purified by standard techniques well known to those of skill in the art. Recombinantly produced binding domain polypeptides can be directly expressed or expressed as a fusion protein. The protein is then purified by a combination of cell lysis (e.g., sonication) and affinity chromatography. For fusion products, subsequent digestion of the fusion protein with an appropriate proteolytic enzyme release the desired SABP and DABP binding domains.

The polypeptides of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982), incorporated herein by reference.

E. Production of Binding Domains by Protein Chemistry Techniques

The polypeptides of the invention can be synthetically prepared in a wide variety of ways. For instance polypeptides of relatively short size, can be synthesized in solution or on a solid support in accordance with conventional techniques. Various automatic synthesizers are commercially available and can be used in accordance with known protocols. See, for example, Stewart and Young, *Solid Phase Peptide Synthesis,* 2d. ed., Pierce Chemical Co. (1984).

Alternatively, purified and isolated SABP, DABP or DBL family proteins may be treated with proteolytic enzymes in order to produce the binding domain polypeptides. For example, recombinant DABP and SABP proteins may be used for this purpose. The DABP and SABP protein sequence may then be analyzed to select proteolytic enzymes to be used to generate polypeptides containing desired regions of the DABP and SABP binding domain. The desired polypeptides are then purified by using standard techniques for protein and peptide purification. For a review of standard techniques see, *Methods in Enzymology,* "Guide to Protein Purification", M. Deutscher, ed. Vol. 182 (1990), pages 619–626, which is incorporated herein by reference.

F. Modification of Nucleic Acid and Polypeptide Sequences

The nucleotide sequences used to transfect the host cells used for production of recombinant binding domain polypeptides can be modified according to standard techniques to yield binding domain polypeptides, with a variety of desired properties. The binding domain polypeptides of the present invention can be readily designed and manufactured utilizing various recombinant DNA techniques well known to those skilled in the art. For example, the binding domain polypeptides can vary from the naturally-occurring sequence at the primary structure level by amino acid insertions, substitutions, deletions, and the like. These modifications can be used in a number of combinations to produce the final modified protein chain.

The amino acid sequence variants can be prepared with various objectives in mind, including facilitating purification and preparation of the recombinant polypeptides. The modified polypeptides are also useful for modifying plasma half-life, improving therapeutic efficacy, and lessening the severity or occurrence of side effects during therapeutic use. The amino acid sequence variants are usually predetermined variants not found in nature but exhibit the same immunogenic activity as naturally occurring polypeptides. For instance, polypeptide fragments comprising only a portion (usually at least about 60–80%, typically 90–95%) of the primary structure may be produced. For use as vaccines, polypeptide fragments are typically preferred so long as at least one epitope capable of eliciting production of blocking antibodies remains.

In general, modifications of the sequences encoding the binding domain polypeptides may be readily accomplished by a variety of well-known techniques, such as site-directed mutagenesis (see, Giliman and Smith, *Gene* 8:81–97 (1979) and Roberts, S. et al., *Nature* 328:731–734 (1987)). One of ordinary skill will appreciate that the effect of many mutations is difficult to predict. Thus, most modifications are evaluated by routine screening in a suitable assay for the desired characteristic. For instance, changes in the immunological character of the polypeptide can be detected by an appropriate competitive binding assay. Modifications of other properties such as redox or thermal stability, hydrophobicity, susceptibility to proteolysis, or the tendency to aggregate are all assayed according to standard techniques.

G. Diagnostic and Screening Assays

The polypeptides and nucelic acids of the invention can be used in diagnostic applications for the detection of merozoites or nucleic acids in a biological sample. The presence of parasites can be detected using several well recognized specific binding assays based on immunological results. (See U.S. Pat. Nos. 4,366,241; 4,376,110; 4,517,288; and 4,837,168). For instance, labeled monoclonal antibodies to polypeptides of the invention can be used to detect merozoites in a biological sample. Alternatively, labelled polypeptides of the invention can be used to detect the presence of antibodies to SABP or DABP in a biological sample. For a review of the general procedures in diagnostic immunoassays, see also *Basic and Clinical Immunology* 7th Edition (D. Stites and A. Terr ed.) 1991.

In addition, modified polypeptides, antibodies or other compounds capable of inhibiting the interaction between SABP or DABP and erythrocytes can be assayed for biological activity. For instance, polypeptides can be recombinantly expressed on the surface of cells and the ability of the cells to bind erythrocytes can be measured as described below. Alternatively, peptides or antibodies can tested for the ability to inhibit binding between erythrocytes and merozoites or SABP and DABP.

Cell-free assays can also be used to measure binding of DABP or SABP polypeptides to isolated Duffy antigen or glycophorin polypeptides. For instance, the erythrocyte proteins can be immobilized on a solid surface and binding of labelled SABP or DABP polypeptides can be measured.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

In addition, the polypeptides of the invention can be assayed using animal models, well known to those of skill in the art. For *P falciparum* the in vivo models include Aotus sp. monkeys or chimpanzees; for *P. vivax* the in vivo models include Saimiri monkeys.

In the case of the use nucleic acids for diagnostic purposes, standard nucleic hybridization techniques can be used to detect the presence of the genes identified here (e.g., members of the DBL family). If desired, nucleic acids in the sample may first be amplified using standard procedures such as PCR. Diagnostic kits comprising the appropriate primers and probes can also be prepared.

H. DBL Targeted Therepeutics

DBL polypeptides are expressed on the surface of Plasmodium-infected erythrocytes. As such, they present ideal targets for therepeutics which target infected erythrocytes. In one preferred embodiment of the present invention, cytotoxic antibodies or antibody fusion proteins with cytotoxic agents are targeted against DBL proteins, killing infected erythrocytes and inhibiting the reproduciton of Plasmodium in an infected host.

The procedure for attaching a cytotoxic agent to an antibody will vary according to the chemical structure of the agent. Antibodies and cytotoxic agents are typically bound together chemically or, where the antibody and cytotoxic agents are both polypeptides, are optionally synthesized recombinantly as a fusion protein. Polypeptides typically contain variety of functional groups; e.g., carboxylic acid (COOH) or free amine (—NH$_2$) groups, which are available for reaction with a suitable functional group on either the antibody or the cytotoxic agent.

Alternatively, antibodies or cytotoxic agents are derivitized to attach additional reactive functional groups. The derivatization optionally involves attachment of linker molecules such as those available from Pierce Chemical Company, Rockford Ill. A "linker", as used herein, is a molecule that is used to join the nucleic acid binding molecule to the receptor ligand. The linker is capable of forming covalent bonds to both the antibody and the cytotoxic agent. Suitable linkers are well known to those of skill in the art and include, but are not limited to, straight or branched-chain carbon linkers, heterocyclic carbon linkers, or peptide linkers. Where the antibody and the cytotoxic agent are polypeptides, the linkers are joined to the constituent amino acids through their side groups (e.g., through a disulfide linkage to cysteine) or to the alpha carbon amino and carboxyl groups of the terminal amino acids.

A bifunctional linker having one functional group reactive with a group on a particular ligand, and another group reactive with a nucleic acid binding molecule, can be used to form the desired conjugate. Alternatively, derivatization can proceed through chemical treatment of the ligand or nucleic acid binding molecule, e.g., glycol cleavage of the sugar moiety of a glycoprotein with periodate to generate free aldehyde groups. The free aldehyde groups on the glycoprotein may be reacted with free amine or hydrazine groups on an agent to bind the agent thereto (See, e.g., U.S. Pat. No. 4,671,958). Procedures for generation of free sulfhydryl groups on polypeptides, are known (See, e.g., U.S. Pat. No. 4,659,839).

Many procedures and linker molecules for attachment of various compounds to proteins are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987). In particular, production of various antibody conjugates is well-known within the art and can be found, for example in Thorpe et al., *Monoclonal Antibodies in Clinical Medicine,* Academic Press, pp. 168–190 (1982), Waldmann, *Science,* 252: 1657 (1991), and U.S. Pat. Nos. 4,545,985 and 4,894,443.

A number of antibodies which bind cell surface receptors have been converted to form suitable for incorporation into fusion proteins, and similar strategies are used to create fusion-protein antibodies which bind DBR polypeptides. see Batra et al., *Mol. Cell. Biol.,* 11: 2200–2205 (1991); Batra et al., *Proc. Natl. Acad. Sci. USA,* 89: 5867–5871 (1992); Brinkmann, et al. *Proc. Natl. Acad. Sci. USA,* 88: 8616–8620 (1991); Brinkmann et al., *Proc. Natl. Acad. Sci. USA,* 90: 547–551 (1993); Chaudhary et al., *Proc. Natl. Acad. Sci. USA,* 87: 1066–1070 (1990); Friedman et al., *Cancer Res.* 53: 334–339 (1993); Kreitman et al., *J. Imnnunol.,* 149: 2810–2815 (1992); Nicholls et al., *J. Biol. Chem.,* 268: 5302–5308 (1993); and Wells, et al., *Cancer Res.,* 52: 6310–6317 (1992), respectively).

B. Production of Fusion Proteins

Where the antibody fragment and/or the cytotoxic agents are relatively short polypeptides (i.e., less than about 50 amino acids) they are often synthesized using standard chemical peptide synthesis techniques. Where both molecules are relatively short, a chimeric molecule is optionally synthesized as a single contiguous polypeptide. Alternatively, the ligand and the nucleic acid binding molecule can be synthesized separately and then fused chemically.

Solid phase synthesis in which the C-terminal amino acid of the sequence is attached to an insoluble support followed by sequential addition of the remaining amino acids in the sequence is a preferred method for the chemical synthesis of the ligands of this invention. Techniques for solid phase synthesis are described by Barany and Merrifield, *Solid-Phase Peptide Synthesis;* pp. 3–284 in *The Peptides: Analysis, Synthesis, Biology. Vol. 2: Special Methods in Peptide Synthesis, Part A.,* Merrifield, et al. *J. Am. Chem. Soc.,* 85: 2149–2156 (1963), and Stewart et al., *Solid Phase Peptide Synthesis,* 2nd ed. Pierce Chem. Co., Rockford, Ill. (1984) which are incorporated herein by reference.

In a preferred embodiment, the fusion molecules of the invention are synthesized using recombinant nucleic acid methodology. Generally this involves creating a nucleic acid sequence that encodes the receptor-targeted fusion molecule, placing the nucleic acid in an expression cassette under the control of a particular promoter, expressing the protein in a host, isolating the expressed protein and, if required, renaturing the protein. Techniques sufficient to guide one of skill through such procedures are found in, e.g., Berger, Sambrook, Ausubel, Innis, and Freshney (all supra).

While the two molecules are often joined directly together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

Once expressed, recombinant fusion proteins can be purified according to standard procedures, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182: *Guide to Protein Purification.,* Academic Press, Inc. N.Y. (1990)). Substantially pure compositions of about 50 to 95% homogeneity are preferred, and 80 to 95% or greater homogeneity are most preferred for use as therepeutic agents.

One of skill in the art will recognize that after chemical synthesis, biological expression, or purification, the fusion molecule may possess a conformation substantially different than the native conformations of the constituent polypeptides. In this case, it is often necessary to denature and reduce the polypeptide and then to cause the polypeptide to re-fold into the preferred conformation. Methods of reducing and denaturing proteins and inducing re-folding are well known to those of skill in the art (See, Debinski et al. *J. Biol. Chem.,* 268: 14065–14070 (1993); Kreitman and Pastan, *Bioconjug. Chem.,* 4: 581–585 (1993); and Buchner, et al., *Anal. Biochem.,* 205: 263–270 (1992).

I. Pharmaceutical Compositions Comprising Binding Domain Tides

The polypeptides of the invention are useful in therapeutic and prophylactic applications for the treatment of malaria. Pharmaceutical compositions of the invention are suitable for use in a variety of drug delivery systems. Suitable formulations for use in the present invention are found in *Remington's Pharmaceutical Sciences,* Mack Publishing Company, Philadelphia, Pa., 17th ed. (1985), which is incorporated herein by reference. For a brief review of methods for drug delivery, see, Langer, *Science* 249:1527–1533 (1990), which is incorporated herein by reference.

The polypeptides of the present invention can be used in pharmaceutical and vaccine compositions that are useful for administration to mammals, particularly humans. The polypeptides can be administered together in certain circumstances, e.g. where infection by both *P. falciparum* and *P. vivax* is likely. Thus, a single pharmaceutical composition can be used for the treatment or prophylaxis of malaria caused by both parasites.

The compositions are suitable for single administrations or a series of administrations. When given as a series, inoculations subsequent to the initial administration are given to boost the immune response and are typically referred to as booster inoculations.

The pharmaceutical compositions of the invention are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In certain embodiments patients with malaria may be treated with SABP or DABP polypeptides or other specific blocking agents (e.g. monoclonal antibodies) that prevent binding of Plasmodium merozoites and schizonts to the erythrocyte surface.

The amount administered to the patient will vary depending upon what is being administered, the state of the patient and the manner of administration. In therapeutic applications, compositions are administered to a patient already suffering from malaria in an amount sufficient to inhibit spread of the parasite through erythrocytes and thus cure or at least partially arrest the symptoms of the disease and its complications. An amount adequate to accomplish this is defined as "therapeutically effective dose." Amounts effective for this use will depend on the severity of the disease, the particular composition, and the weight and general state of the patient. Generally, the dose will be in the range of about 1 mg to about 5 gm per day, preferably about 100 mg per day, for a 70 kg patient.

Alternatively, the polypeptides of the invention can be used prophylactically as vaccines. The vaccines of the invention contain as an active ingredient an immunogenically effective amount of the binding domain polypeptide or of a recombinant virus as described herein. The immune response may include the generation of antibodies; activation of cytotoxic T lymphocytes (CTL) against cells presenting peptides derived from the peptides encoded by the SABP, DABP or DBL sequences of the present invention, or other mechanisms well known in the art. See e.g. Paul *Fundamental Immunology Second Edition* published by Raven press New York (incorporated herein by reference) for a description of immune response. Useful carriers are well known in the art, and include, for example, thyroglobulin, albumins such as human serum albumin, tetanus toxoid, polyamino acids such as poly(D-lysine:D-glutamic acid), influenza, hepatitis B virus core protein, hepatitis B virus recombinant vaccine. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

The DNA or RNA encoding the SABP or DABP binding domains and the DBL gene family motifs may be introduced into patients to obtain an immune response to the polypeptides which the nucleic acid encodes. Wolff et. al., *Science* 247: 1465–1468 (1990) which is incorporated herein by reference describes the use of nucleic acids to produce expression of the genes which the nucleic acids encode.

Vaccine compositions containing the polypeptides, nucleic acids or viruses of the invention are administered to a patient to elicit a protective immune response against the polypeptide. A "protective immune response" is one which prevents or inhibits the spread of the parasite through erythrocytes and thus at least partially prevent the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 μg to about 1 gm of peptide for a 70 kg patient, followed by boosting dosages of from about 100 μg to about 1 gm of the polypeptide pursuant to a boosting regimen over weeks to months depending upon the patient's response and condition e.g. by measuring levels of parasite in the patient's blood. For nucleic acids, typically 30–1000 ug of nucleic acid is injected into a 70 kg patient, more typically about 50–150 ug of nucleic acid is injected into a 70 kg patient followed by boosting doses as appropriate.

The following examples are offered by way of illustration, not by way of limitation.

EXAMPLE 1

Identification of the Amino-terminal, Cysteine-rich Region of SABP and DABP as Binding Domains for Erythrocytes 1. Expression of the SABP Binding Domain Polypeptide on the Surface of Cos Cells To demonstrate that the amino-terminal, cysteine-rich region of the SABP protein is the sialic acid binding region, this region of the protein was expressed on the surface of mammalian Cos cells in vitro. This DNA sequence is from position 1 to position 1848 of the SABP DNA sequence (SEQ ID No 3). Polymerase chain reaction technology (PCR) was used to amplify this region of the SABP DNA directly from the cloned gene.

Sequences corresponding to restriction endonuclease sites for Pvull or Apal were incorporated into the oligonucleotide sequence of the probes used in PCR amplification in order to facilitate insertion of the PCR-amplified regions into the pRE4 vector (see below). The specific oligonucleotides, 5'-ATCGATCAGCTGGGAAGAAATACTTCATCT-3' (SEQ ID NO:17), and 5'-ATCGATGGGCCCCGAAGTTTGTTCATTATT-3' (SEQ ID NO:18) were synthesized. These oligonucleotides were used as primers to PCR-amplify the region of the DNA sequence encoding the cysteine-rich amino terminal region of the SABP protein.

PCR conditions were based on the standard described in Saiki, et al., *Science* 239: 487–491 (1988). Template DNA was provided from cloned fragments of the gene encoding SABP which had been spliced and re-cloned as a single open-reading frame piece.

Figure 2:
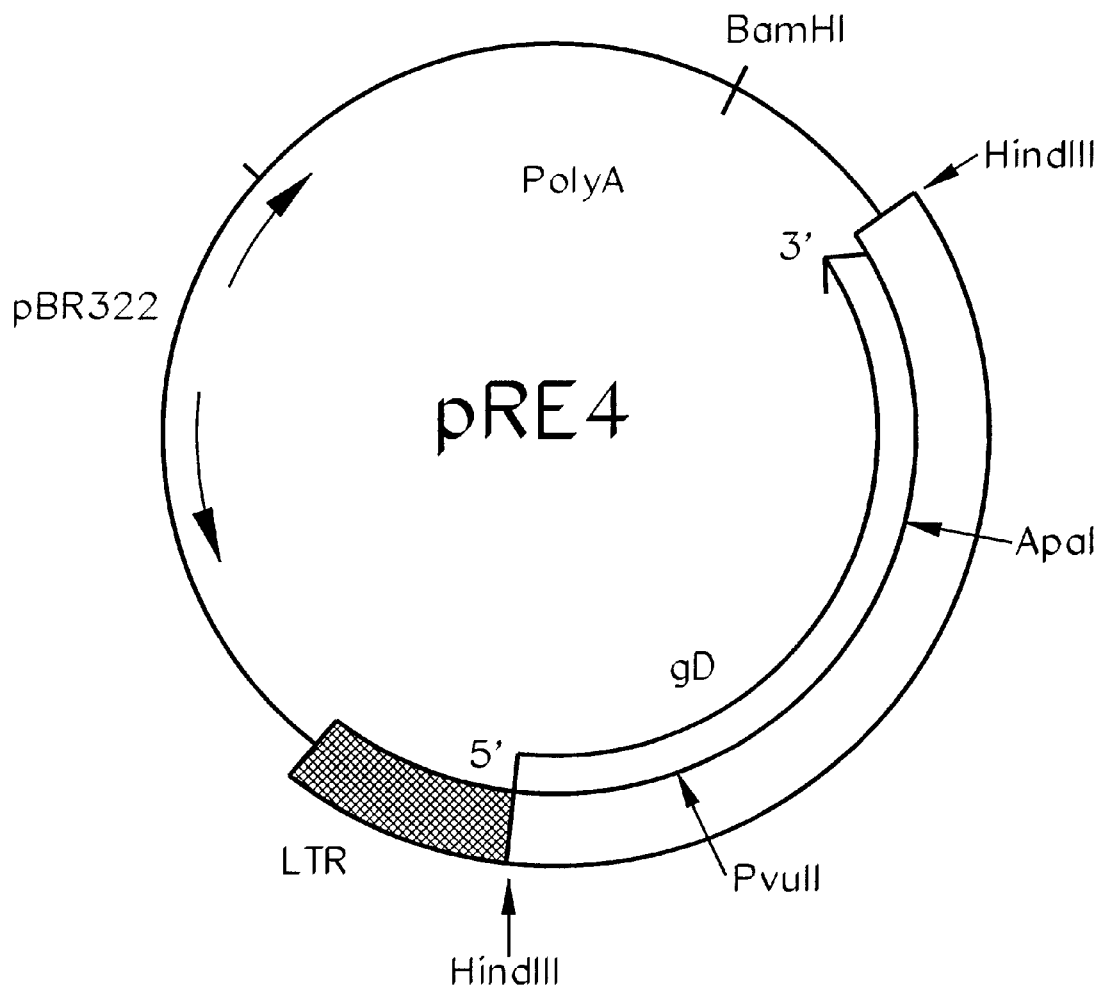
FIG. 2 represents a schematic of the pRE4 cloning vector.

The vector, pRE4, used for expression in Cos cells is shown in FIG. 2. The vector has an SV40 origin of replication, an ampicillin resistance marker and the Herpes simplex virus glycoprotein D gene (HSV glyd) cloned downstream of the Rous sarcoma virus long terminal repeats (RSV LTR). Part of the extracellular domain of the HSV glyd gene was excised using the Pvull and Apal sites in HSV glyd.

As described above, the PCR oligonucleotide primers contained the Pvull or Apal restriction sites. The PCR-amplified DNA fragments obtained above were digested with the restriction enzymes PvuII and ApaI and cloned into the PvuII and ApaI sites of the vector pRE4. These constructs were designed to express regions of the SABP protein as chimeric proteins with the signal sequence of HSV glyd at the N-terminal end and the transmembrane and cytoplasmic domain of HSV glyd at the C-terminal end. The signal sequence of HSV glyd targets these chimeric proteins to the surface of Cos cells and the transmembrane segment of HSV glyd anchors these chimeric proteins to the Cos cell surface.

Mammalian Cos cells were transfected with the pRE4 constructs containing the PCR-amplified SABP DNA regions, by calcium phosphate precipitation according to standard techniques.

2. Expression of the DABP Binding Domain Polypeptide on the Surface of Cos Cells To demonstrate that the amino-terminal, cysteine-rich region of the DABP protein is the binding domain, this region was expressed on the surface of Cos cells. This region of the DNA sequence from position 1–975 was first PCR-amplified (SEQ ID No 1).

Sequences corresponding to restriction endonuclease sites for PvuII or ApaI were incorporated into the oligonucleotide probes used for PCR amplification in order to facilitate subsequent insertion of the amplified DNA into the pRE4 vector, as described above. The oligonucleotides, 5'-TCTCGTCAGCTGACGATCTCTAGTGCTATT-3' (SEQ ID NO:19) and 5'-ACGAGTGGGCCCTGTCACAACTTCCTGAGT-3' (SEQ. ID NO:20) were synthesized. These oligonucleotides were used as primers to amplify the region of the DABP DNA sequence encoding the cysteine-rich, amino-terminal region of the DABP protein directly from the cloned DABP gene, using the same conditions described above.

The same pRE4 vector described above in the section on expression of SABP regions in Cos cells was also used as a vector for the DABP DNA regions.

3. Binding Studies With Erythrocytes

To demonstrate their ability to bind human erythrocytes, the transfected Cos cells expressing binding domains from DABP and SABP were incubated with erythrocytes for two hours at 37° C. in culture media (DMEM/10% FBS). The non-adherent erythrocytes were removed with five washes of phosphate-buffered saline and the bound erythrocytes were observed by light microscopy. Cos cells expressing the amino terminal, cysteine-rich SABP polypeptides on their surface bound untreated human erythrocytes, but did not bind neuraminidase treated erythrocytes, that is, erythrocytes which lack sialic acid residues on their surface. Cos cells expressing other regions of the SABP protein on their surface did not bind human erythrocytes. These results identified the amino-terminal, cysteine-rich region of SABP as the erythrocyte binding domain and indicated that the binding of Cos cells expressing these regions to human erythrocytes is specific. Furthermore, the binding of the expressed region to erythrocytes is identical to the binding pattern seen for the authentic SABP-175 molecule upon binding to erythrocytes.

Similarly, Cos cells expressing the amino-terminal cysteine-rich region of DABP on their surface bound Duffy-positive human erythrocytes, but did not bind Duffy-negative human erythrocytes, that is erythrocytes which lack the Duffy blood group antigen. Cos cells expressing other regions of the DABP protein on their surface did not bind human erythrocytes. These results identified the amino-terminal cysteine rich region of DABP as the erythrocyte binding domain and indicated that the binding of the Cos cells was specific.

EXAMPLE 2

Isolation of Polynucleotide Sequences in the DBL Family

Materials and Methods

*P.falciparum* Clones and Lines. *P. falciparum* clones 3D7, D10, LF4/1, Camp/A1, SL/D6, HB3, 7G8, V1/S, T2/C6, KMWII, ItG2F6, FCR3/A2 and Dd2 have been previously tabulated (Dolan, et al. (1993), *Mol. Biochem. Parasitol.* 61, 137–142). Line Dd2/NM1 was selected from clone Dd2 for invasion via a sialic acid-independent pathway (Dolan, et al. (1990), *J. Clin. Invest.* 86, 618–624). All parasites were maintained in vitro by standard methods (Trager, et al. (1976), *Science* 193, 673–675).

DNA and RNA Isolation and Analysis. DNA was extracted as described (Peterson, et al. (1990), *Proc. Natl. Acad. Sci. USA* 87, 3018–3022). Endonuclease digestion, agarose gel electrophoresis, and filter hybridizations were performed by standard methods (Sambrook, et al. (1989), *Molecular Cloning: A Laboratory Manual* (Cold Spring Harbor Lab. Press, Plainview, N.Y.), 2nd Ed.). All hybridizations were at 56° C. (Sambrook, et al. (1989), *Molecular Cloning: A Laboratory Manual* (Cold Spring Harbor Lab. Press, Plainview, N.Y.), 2nd Ed.). Blots were washed for 2 min. at room temperature in 2× standard saline/phosphate/EDTA (SSPE) with 0.5% SDS, followed by two higher stringency washes at 50° C. in 0.3×SSPE with 0.5% SDS. Parasite chromosomes were embedded in agarose blocks and separated by pulsed field gel electrophoresis (Dolan, et al. (1993), *Methods. Mol. Biol.* 21, 319–332). RNA was isolated from cultured parasites by LiC1 extraction of Catrimox-14-precipitated RNA (Dahle, et al. (1993), *BioTechniques* 15, 1102–1105). Agarose gel electrophoresis of total RNA and filter hybridizations were performed by standard methods (Sambrook, et al. (1989), *Molecular Cloning: A Laboratory Manual* (Cold Spring Harbor Lab. Press, Plainview, N.Y.), 2nd Ed.).

Oligonucleotide Primers and PCR. Primers specific for E31a used in a RT-PCR to test for expression of this sequence were E31aT2 (5'-AGA-CCT-CAA-TIT-CTA-AG-3') (SEQ ID NO:21) and E31aRev1 (5'-AAT-CGC-GAG-CAT-CAT-CTG-3') (SEQ ID NO:22).

Two primers were used to amplify additional sequences from genes encoding DBL domains. These were designed from conserved amino acids encoded in the DBL domain of the eba-175 and E31a sequences. After adaptation to incorporate the most frequently-used *P. falciparum* codons, forward primer UNIEBP5'[5'-CC(A/G)-AG(G/A)-AG(G/A)-CAA-(G/A)AA-(C/T)TA-TG-3] (SEQ ID NO:23), based upon the amino acid sequence PRRQKLC, and reverse primer UNIEBP3'[5'-CCA-(A/T)C(T/G)-(T/G)A(A/G)-(A/G)AA-TTG-(A/T)GG-3'] (SEQ ID NO:24), based upon the amino acid sequence PQFLRW, were synthesized.

RT-PCR amplifications were performed as described (Kawasaki, et al. (1990), *PCR Protocols, A Guide to Methods and Applications,* eds. Innis, M. A., Gelfand, D. H., Sninsku, J. J. & White, T. J. (Academic, San Diego), pp. 21–27). In brief, 0.5 to 1 mg of total RNA was treated with RQ1 DNAse (Promega), phenol/chloroform extracted, and ethanol precipitated. The RNA was then annealed with random oligonucleotide primers and extended with Superscript reverse transcriptase (GIBCO/BRL). PCR cycling conditions were 94° C. for 10 sec, 45° C. for 15 sec, and 72° C. for 45 sec, for 30 cycles. All PCRs were performed in an Idaho Technology air thermal cycler using buffer containing 2 mM Mg2+.

PCR amplification products were separated by use of PCR Purity Plus gels and protocols (AT Biochem, Malvern, Pa.).

DNA Clones and Hybridization Probes. Clone pE31a was isolated from a genomic library prepared from the region of chromosome 7 linked to chloroquine resistance Walker-Jonah, et al. (1992), *Mol. Biochem. Parasitol.* 51, 313–320. Clone pS31H (GenBank accession no. L38454), containing an insert encompassing that of pE31a, was cloned from a size-selected Hind III restriction digest of Dd2 genomic DNA.

Clone pEBLe1 was cloned from a RT-PCR of Dd2 cDNA after amplification with primers UNIEBP5' (SEQ ID NO:23) and UNIEBP3' (SEQ ID NO:24). Clone pEBP1.2 (GenBank accession no. L38450), containing an insert encompassing that of pEBLe1, was isolated from a Dd2 cDNA library probed with pEBLe1. DBL-encoding sequences of dbl-nm1–4 (GenBank accession no. L38455) and dbl-nm1–5 (GenBank accession no. L38453) were amplified by RT-PCR from first strand cDNA of line Dd2/NM using primers UNIEBP5' and UNIEBP3'. Sequencing was performed on double stranded DNA templates by standard protocols for the dideoxynucleotide method. (Sequenase; U.S. Biochemicals).

Sequences related to the E31a sequence were detected with the 3005 bp insert of clone pS31H. The eba-175 gene was detected with a PCR amplified probe consisting of the first 1825 bp of the coding sequence. ebl-1 sequences were detected with the 2098 bp insert of clone pEBP1.2. All probes were comparable in organization, each containing a region encoding at least one DBL domain and varying amounts of flanking sequence.

Homology searches and alignments. Homology searches were performed with BLAST and the Genetics Computer Group program FASTA (Altschul, et al. (1990), *J. Mol. Biol.* 215, 403–410; Devereux, et al. (1984), *Nucleic Acids. Res.* 12(1 Pt 1, 387–395). Optimized alignments were produced with MACAW sequence alignment software (Schuler, et al. (1991), *Proteins.* 9, 180–190).

Results

Figure 4:
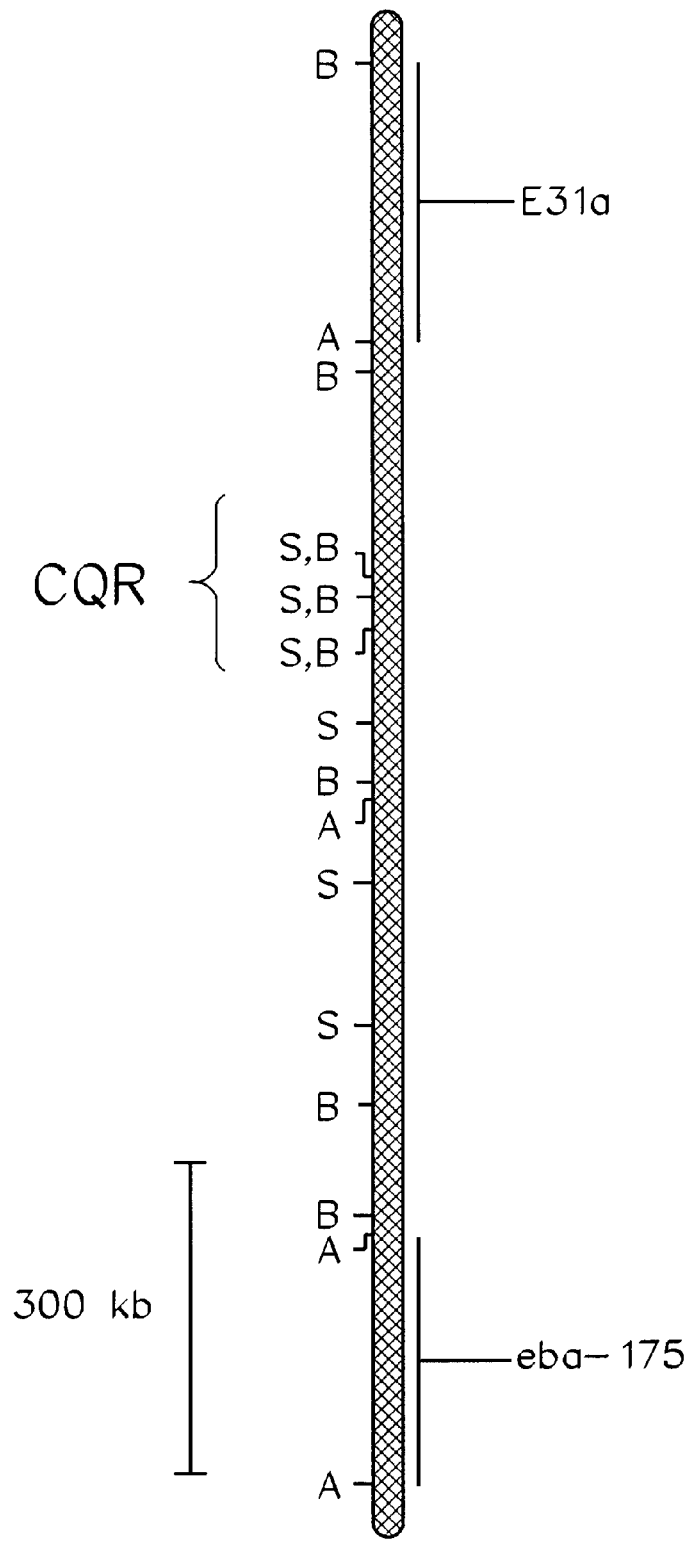
FIG. 4 shows the relative position of the E31a ORF on chromosome 7.

Multiple *P. falciparum* sequences encode DBL domains. Positional cloning experiments directed to *P. falciparum* chromosome 7 identified an ORF (E31a) encoding a DBL domain that is homologous to the domains found in the *P. vivax* and *P. knowlesi* DABPs and the *P. falciparum* SABP. FIG. 4 shows the realtive position of the E31a ORF on chromosome 7.

The homology between the DBL domains of E31a and the erythrocyte-binding proteins is due to the presence of short motifs of highly conserved amino acids. These well-conserved stretches are separated by non-homologous sequences and by deletions and insertions that vary the size of the domain by >60 aa. The typical DBL domain contains 12 or more cysteine residues and has 7 conserved tryptophan residues. Additional well conserved amino acids include 4 arginines, 3 aspartates, 9 positions with aliphatic residues (alanine, isoleucine, leucine, or valine) and 4 with aromatic amino acids (tryptophan, phenylalanine, or tyrosine).

Probes spanning the sequence that encodes the E31a DBL domain hybridized to multiple fragments within a single restriction digest and yielded bands that varied among parasite lines. The numerous distinct bands from a selection of different parasite DNAs indicated a large number of diverse but related elements. These multiple bands varied among different *P. falciparum* clones, in contrast to the well-conserved, single-copy signal obtained with the eba-175 probe.

Because of the numerous cross-hybridizing sequences, it seemed likely that many of these related sequences would be on different chromosomes of the parasite. PFG electrophoresis of *P. falciparum* Dd2 chromosomes and hybridization with the E31a probe identified a number of cross-hybridizing sequences on multiple chromosomes. A control hybridization with the eba-175 probe under identical conditions yielded a single band of hybridization from chromosome 7.

RNA Analysis of DBL Elements. Sequences from E31a (pS31H insert) were used to probe RNA blots for corresponding transcripts. No hybridization was detected. Because it was still possible that a message of low abundance was not being detected on the RNA blot, RT-PCR was used as a means of more sensitive detection. For this purpose, cDNA was generated by RT from random primers annealed to DNAse-treated total RNA. E31a-specific oligonucleotides were then used to test for amplification from the cDNA. No amplification of the E31a sequence was obtained, while genomic DNA controls and amplification from cDNA by dihydrofolate reductase/thymidylate synthetase-specific primers yielded the expected bands. A screen of a cDNA library with E31a specific probes also failed to detect any clones hybridizing with the ORF. These results indicate that E31a is either a pseudogene, or is expressed in parasite strains or stages not examined in this work.

A PCR Method to Isolate Sequences Encoding DBL Domains. The identification of short conserved motifs in DBL domains that otherwise have extreme diversity led to a PCR strategy using degenerate oligonucleotide primers designed from conserved amino acid sequences in the DBL domains. Sequences PRRQKLC and PQFLRW were judged most suitable for minimizing degeneracy while allowing amplification of expressed DBL sequences. After these considerations and adjustment for *P. falciparum* codon usage, primers UNIEBP5' and UNIEBP3' were synthesized.

While some *P. falciparum* lines yielded similar patterns of amplified bands (e.g. Dd2 and MCamp; FCR3/A2 and K-1), no two separate isolates showed identical patterns, reflecting the diversity of the DBL domains in the parasite lines. A few bands of the same apparent size were present in many isolates. These included a consistent 490 bp product that was determined to be the eba-175 gene by its expected size and hybridization to a gene-specific probe. The number of discernible bands probably underestimates the number of amplifiable sequences because of overlapping products of the same size and possible preferential amplification of some sequences over others. Nevertheless, the parasite-specific patterns in the amplified bands may provide a means to quickly type isolates and serves as a measure of parasite diversity in field samples.

To identify DBL-encoding sequences in RNA transcripts, the UNIEBP primers were used to amplify first-strand cDNAs generated from DNAse-treated RNA preparations. Amplified products from Dd2, 3D7, HB3 and MCAMP cDNAs had diverse sizes ranging from 400 bp to nearly 1 kb. These included a band at 480–500 bp that was determined to be eba-175 from its expected size and cross-hybridization to an eba-175-specific probe. Other bands were from amplification of different transcripts encoding DBL domains. Dd2-NM1 RNA, for example, yielded bands above the eba-175 product that included two related sequences (dbl-nm1–4, dbl-nm1–5). These bands were found to be isolate-specific and to have features consistent with the var genes described in Example 3, below. Probes that detect dbl-nm1–4 and dbl-nm1–5 hybridized to multiple chromosomes and aligned more closely with E31a than with EBA-175 or DABP.

The RT-PCR amplifications also yielded a consistent band that encoded a novel DBL domain distinct from eba-175. A cDNA clone corresponding to this product was isolated by screening a λgt10 Dd2 cDNA library with a radiolabeled ebl-1 probe. Sequence from this and additional overlapping cDNA clones confirmed the conserved motifs of the DBL domain. The alignment of the predicted amino acid sequences showed that the DBL domain of ebl-1 is more similar to eba-175 than to the multicopy genes. There was, however, extensive divergence from eba-175 and other known genes outside of the amplified region.

In contrast to the multicopy hybridization patterns of dbl-nm1–4 and dbl-nm1–5, the ebl-1 sequence, like that of eba-175, was found to have hybridization patterns consistent with a conserved single-copy gene. Probes specific for ebl-1 hybridized only to chromosome 13, and restriction analysis with the enzymes Cla I, EcoR1, HindIII, Hinf I, Nsi I, Rsa I, and Spe I, all yielded bands expected from a single copy sequence. RNA blots probed with ebl-1-specific sequences showed several bands of hybridization, however, corresponding to 8–9.5 kb transcripts in mRNA from the Dd2 and 3D7 parasites. The transcripts of different size may result from alternative start and termination points or from incompletely processed species containing introns.

EXAMPLE 3

Isolation of var Genes

Materials and Methods

Parasite clones, DNA analysis and Chromosome Mapping. Parasite clones were cultivated by the methods of (Trager, et al. (1976), *Science* 193, 673–675). DNA was extracted from parasite cultures as described (Peterson, et al. (1988), *Proc. Natl. Acad. Sci. USA* 85, 9114–9118) except that the DNA was as recoverd by ethanol precipitation rather than spooling. Fingerprint analysis with the pC4.H32 probe was used to confirm DNA preparations (Dolan, et al. (1993), *Mol. Biochem. Parasitol.* 61, 137–142). Southern blotting to Nytran membranes was recommended by the manufacturer (Schleicher & Schuell, Keene, N.H.). PFG separation of the 14 *P. falciparum* chromosomes and chromosome mapping were performed as described (Wellems, et. al. (1987), *Cell* 49, 633–642; Sinnis, et al. (1988); *Genomics* 3, 287–295).

RNA isolation. Parasites from 200 ml mixed stage cultures (5–10% parasitemia) were released by saponin lysis as for DNA preparations except that the procedures were performed with ice-cold solutions. RNA was immediately isolated from the parasite pellet by guanidine thiocyanate/phenol-chloroform methods, recovered and treated with RNAase-free DNAse (Creedon, et al. (1994), *J. Biol. Chem.* 269, 16364–16370. RNA in $H_2O$ was combined with 2 vol 100% ETOH, distributed into 2 ml vials and frozen as stock at −70° C. RNA was recovered by precipitation with 0.1 vol 3M NaOAc. RNA blots were generated and probed as described (Creedon, et al. (1994), *J. Biol. Chem.* 269, 16364–16370).

YAC isolation, chromosome-segment libraries and cDNA libraries. Overlapping YACs spanning the 300 kb segment of chromosome 7 that contains the CQR locus were obtained from a YAC library of a CQR FCR3 parasite line de Bruin, et al. (1992), *Genomics* 14, 332–339) by the procedures of Lanzer, et al. (1993), *Nature* 654–657. Orientation of the YACs and their overlaps were identified with probes obtained from the YAC ends by inverted PCR.

Attempts to construct cosmid libraries and large insert (~10 kb) λ libraries from high molecular weight *P. falci-parum* genomic DNA yielded only rearranged clones. An alternative approach was therefore taken in which chromosome-segment libraries were constructed that contained small (0.5–5 kb) inserts in plasmid vectors. Plasmid libraries containing AluI, HinfI, RsaI and SspI inserts in pCDNAII were constructed from Dd2 chromosome 7 restriction fragments purified by pulsed-field gel (PFG) electrophoresis (Wellems, et al. (1991), *Proc. Natl. Acad. Sci. USA* 88, 3382–3386). A plasmid library from a 34 kb ApaI-SmaI restriction fragment of YAC PfYED9 was constructed by the same methods. Inserts in the plasmid libraries were generally 0.5–4 kb.

The λgt10 Dd2 cDNA library was prepared under contract by CloneTech Laboratories Inc. (Palo Alto, Calif.) from the DNAse-treated, polyA+ fraction of Dd2 RNA. The cDNA was generated in two separate reactions using oligodT primers or random primers. Products of these reactions were combined, processed and cloned into the EcoRI site of λgt10. $1.6 \times 10^6$ independent recombinants were obtained and amplified.

Isolation of overlapping clones and DNA sequencing. Plasmid clones from the chromosome-segment and YAC-segment libraries were picked at random and their locations were established by restriction mapping. After sequence data from these clones were generated, overlapping clones were isolated in a process of "chromosome walking" by rescreening the libraries with oligonucleotide probes near the ends of sequenced inserts. Sufficient divergence was present among repetitive elements in the sequences to allow distinction of clones and unambiguous assignment of overlaps (generally 50–200 bp).

Sequencing reactions with single-strand M13 DNA (1 μg) and double-strand plasmid DNA (2–5 μg) were performed in 96-well polyvinyl chlordie U-bottom microassay plates using a Sequenase protocol recommended by United States Biochemical Corp. (Cleveland, Ohio). Reactions were separated by 8M urea-6% polyacrylamide sequencing gels and exposed to Kodak BioMax MR film. Sequence data from some clones were also obtained by use of an ABI 373A automated DNA sequencer (Applied Biosystems Inc., Foster City, Calif.). Cycle sequencing reactions were performed using the ABI PRISM DyeDeoxy system.

DNA sequence editing, analyses and display were performed with MacVector software (International Biotechnologies Inc., New Haven, Conn.), BLAST (Altschul, et al. (1990), *J. Mol. Biol.* 215, 403–410), Genetics computer Group programs (Devereux, et al. (1984), *Nucleic Acids Res.* 12, 387–395) and the DNADRAW package (Shapiro, et al. (1986), *Nucleic Acids Res.* 14, 65–73) maintained at the National Institutes of Health.

RESULTS

Figure 5:
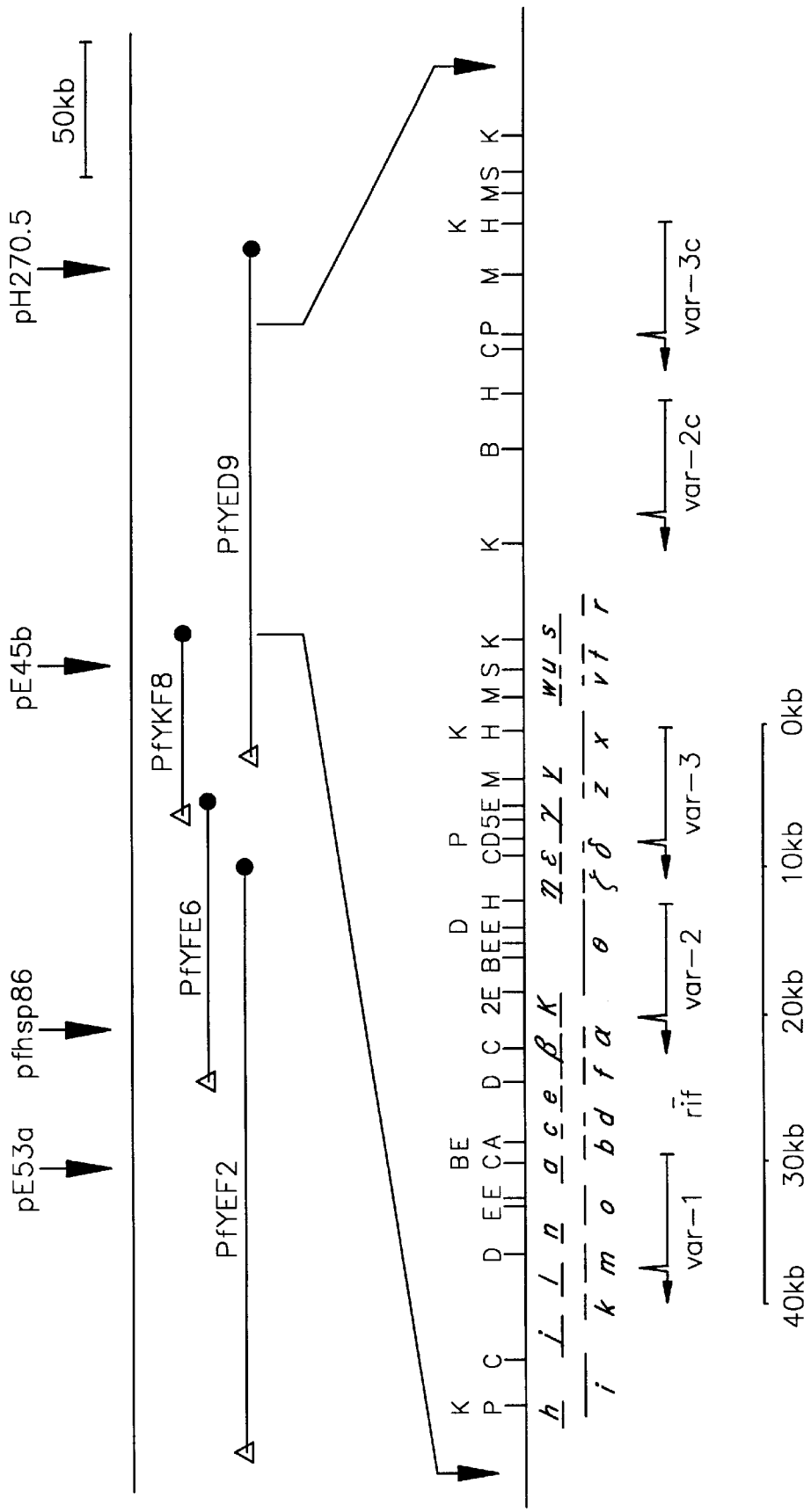
FIG. 5 shows a map of a var gene cluster on chromosome 7. Relative positions of four YACs (PfYEF2, PfYFE6, PfYKF8, PfYED9) are indicated under the chromosome 7 line at the top of the figure. YACs PfYFE6 and PfYKF8 lie entirely within a segment linked to CQR in a genetic cross, whereas YACs PfYED9 and PfYEF2 extend beyond sites (identified by pE53a and pH270.5) that are dissociated from the chloroquine response. The var cluster extends over a region of 100–150 kb in PfYED9. Exons and introns of the var-1, var-2 and var-3 genes within the sequenced 40 kb segment are represented by solid and dotted lines, respectively; arrows show the coding direction. Two more var elements outside of the sequenced region, identified by conserved restriction sites and crosshybridization, are indicated by dashed-lines (var-2c and var-3c). Bold letters mark repeated restriction sites that suggest a duplication in the var-2/var-3 and var-2c/var-3c segments. Enzyme recognition sites: A, ApaI, B, Bgl1; C, Cla1; D, HindIII; E, HaeIII; H, BssHII; K, KpnI; M, BamHI; P, HpaI; S, SmaI. HindIII and HaeIII sites outside of the sequenced region were not mapped. Positions and sizes of inserts from the Dd2 subsegment library are indicated: a, pE280b; b, pB20.3; c, pB600; d, pE21b; e, pB20.24; f, pE32b; h, pE241a; i, pE240a/51d; j, pE33a; k, pB20.23; l, λL17BA6; m, pB20.26; n, pB20SU.27; o, p15J2J3. Inserts from the PfYED9 34 kb ApaI-SmaI fragment library: r, pB3; s, p3G11; t, pJVs; u, p2E10; v, pIG3; w, p2E3; x, p2B6; y, PE10; z, pJYr; α, pC5; β, p1A3; γ, p1F6; δ, p3C3; ε, pA2; ζ, p2A9; η, p3C4; θ, pJZn; κ, p3D8.

Identification of a Large Hypervariable Region Within a Chromosome 7 Segment Linked to Chloroquine Resistance Four overlapping yeast artificial chromosome from the *P. falciparum* FCR3 line were obtained that span the 300 kb chromosome segment linked to CQR, a segment located 300–600 kb from the telomere of chromosome 7. FIG. 5 shows the positions of these YACs (PfYEF2, PfYFE6, PfYKF8, PfYED9) relative to the chromosome map. In order to define the structure of this 300 kb segment, we performed comparative hybridizations to search for polymorphisms between parasite lines. Clones were randomly picked from chromosome segment-specific plasmid libraries and their inserts were hybridized against restriction digests of the YAC and parasite DNAS. Over thirty inserts were identified that recognized PfYEF2, PfYFE6 or PfYKF8 and showed a preponderance of single copy sequences with few polymorphisms (AluI, HinfI, RsaI and SspI-digests), consistent with prior findings that chromosome internal regions are largely conserved and contain a preponderance of single copy sequences. However, fifteen other inserts that recognized PfYED9 showed highly polymorphic sets of repetitive elements in the parasite DNAs. Southern analysis indicated that these polymorphic elements were part of a chromosome hypervariable region contained within the PfYED9 clone.

Mapping and DNA Sequencing of the Hypervariable Region Spanned by YAC PfYED9

Single copy sequences detected by pE45b and pH270.5 flank the hypervariable region spanned by PfYED9 (FIG. 5). The pE45b and pH270.5 probes were therefore used to assign large restriction fragments on the PfYED9 map and establish enzyme recognition sites as reference points. A detailed restriction map of the PfYED9 hypervariable region was then developed. Fifteen overlapping clones "a"–"f" and "h"–"o" in FIG. 5) were isolated by a chromosome walking approach from Dd2 chromosome subsegment libraries (Wellems et al., supra) The inserts yielded 19.1 kb of continuous Dd2 sequence having predicted enzyme recognition sites in perfect accord with the PfYED9 restriction map. Such agreement indicates that the Dd2 and FCR3 sequences in this part of the chromosome are very similar, despite differences elsewhere in the genome that are evident by restriction analysis.

We also obtained genomic sequence data from the 34 kb ApaI-SmaI fragment of PfYED9. Purified PfYED9 DNA was cut with SmaI to yield a 110 kb fragment, which was then isolated by PFG electrophoresis and digested with ApaI. The resulting 34 kb ApaI-SmaI band was purified by PFG electrophoresis, digested in four separate reactions by AliiI, HinAI, RsaI or SspI and incorporated into a plasmid (PCDNAII) library. Cloned inserts from the library were checked for hybridization to the PpYED9 34 kb fragment, assigned to the PfYED9 map and sequenced (FIG. 5). Overlapping inserts were obtained by the chromosome walking approach except for three gaps ("t", "z", "θ" in FIG. 5) which were closed by PCR amplification of PfYED9 DNA using primers from flanking sequences. The cones from PfYED9 ("r"–"z", "γ", "κ" and "α"+"β" in FIG. 5) yielded 22.2 kb of continuous DNA sequence that overlaps the Dd2 sequence at the "f"/"β" junction and has predicted restriction sites that match the PfYED9 map perfectly. The composite sequence from the Dd2 and PfYED9 segments is 40,171 kb.

Structure of a var Gene Cluster and Comparative Analysis of Predicted Amino Acid Sequences The 40,171 bp sequence contains three 10–12 kb regions that have related sequences and structure. Each of these regions harbors a pair of ORFS. The first ORF in each pair begins with a consensus ATG start codon preceded by typical *P. falciparum* non-coding sequence of abundant A+T content. The ORFs of each pair are separated by an intervening AT-rich and non-coding sequence of 0.9–1.1 kb. Presence of consensus intron-exon splice junction sequences at either end of these intervening sequences and lack of a consistent translation start site in the 3' ORF indicate that the each pair of ORFs belongs to an individual gene having a two exon structure. This has been verified by comparison of the genomic sequences to the cDNA sequence of an expressed gene (var-7; subsequent section). The three 10–12 kb regions thus contain members of a variant gene family which have coding regions of 9.23 kb (var-1), 7.99 kb (var-2) and 9.01 kb (var-3). Predicted molecular weights of the encoded proteins are 350 kD, 302 kD and 344 kD, respectively.

The var genes are flanked by additional members of the var family in PfYED9. Restriction analysis identified two additional genes that are 12–35 kb upstream of the sequenced region and are closely related to var-2 and var-3 (var-2c and Var-3c, FIG. 5). The var genes thus have a clustered arrangement in which many individual members are organized in head-to-tail fashion. Between var-1 and var-2 is a 5 kb DNA sequence that harbors a short ORF homologous to that of a repetitive element (rij) suggested to be a transposable element in *P. falciparum*.

The deduced protein sequences of the var genes are highly diverse, yet all contain certain conserved motifs and common structural features. Database searches identified 2 to 4 domains within each var sequence that are homologous to cysteine-rich domains of SABP and DABP. In the var sequences, the first domain near the amino-terminus (DBL domain 1) is the most conserved of the DBL domains and has amino acid signatures that differentiate it from subsequent domains (e.g. consensus peptide sequences GAcAp [Y/F]rrL, CTxLARsfadIgdlVrgrdLYLG and VPTYFDYVpqylrwF). Between DBL domains 1 and 2 is another type of conserved domain, a cysteine-rich interdomain region (CIDR) of 300–400 amino acids. The CIDR does not have all the motifs of a DBL domain, but it does have a region at the 3'end which is homologous to the end of the F1 DBL domain in SABP. The conservation evident in the sequences of DBL domain I and the CIDR suggest that these regions maintain important structures in the head of the variant molecule.

DBL domains 2, 3 and 4 (numbering is according to var-1, the first sequence completed) have less discriminating signatures than domain 1, and show features of cross-alignment and variation in number that suggest these domains can undergo shuffling and deletion.

DBL domain 4 is followed by a segment of variable length and a hydrophobic region that is encoded at the end of the first exon (exon 1). In all var sequences this hydrophobic region fits the criteria of a transmembrane segment. The second exon (exon II) encodes a large (45–55 kD) conserved C-terminal sequence that has an acid character (predicted pI=4.5, vs. 5.9 for the part of the protein upstream of the splice junction) and a cysteine content of <1% (vs. >4% upstream). The position of this C-terminal sequence downstream of a single transmembrane segment suggests that it has a cytoplasmic location.

No consensus signal sequence was detected in the $NH_2$-terminal region of the predicted var ORFs. We note the presence of several motifs in the protein sequences that are known to act as ligands and receptors in the integrin family. These include RGD (var-1 codons 886–88, 1992–94) and DGEA(var-1 codons 2111–14). Not all of these motifs occur in each protein sequence and, when they do occur, their positions vary.

Identification of var Transcripts and Chromosome Expression Sites

To identify transcribed var sequences we screened a λgt10 Dd2 cDNA library with var-containing BssHII restriction fragments that had been purified from PfYED9 and radiolabeled by random hexamer priming. This screening yielded 18 clones with inserts that hybridized back to PfYED9. By cross-hybridization studies and DNA sequence analysis the inserts fell into two groups: group I inserts that aligned with sequences of var exon I (λT240, λT242, λT244, λT284, λT287, λT288, λT295, λT296); and group II inserts that aligned with sequences of var exon II (λT140, λT141, λT142, λT145, λ147, λ148, λT150, λT152).

The full ORF of an expressed var gene (var-7) was determined from λT242 and overlapping cDNA clones that were obtained by a PCR-based walking strategy. The sequence showed that var-7 has a 6.6 kb ORF containing two DBL domains, a hydrophobic transmembrane sequence and carboxy-terminal region typical of var genes (predicted molecular weight 249 kD). Comparison of var-7 with the var-1 sequence demonstrated continuity of the alignments at the predicted splice junction between the ORFs of exons I and II. PCR amplification of Dd2 genomic DNA was also performed with primers derived from the two var-7 exons. Sequence of this var-7 PCR product confirmed consensus splice sites and a 1 kb intron typical of the var genes. Transcription of var-7 was detected as a 7.5 kb band by RNA blot analysis.

Chromosome mapping experiments with a var-7-specific probe localized the var-7 gene to a region that is 600 kb from one end of Dd2 chromosome 12 (chromosome 12 has a length of 2600 kb). No hybridization of the var-7 probe was detected to any other Dd2 chromosome nor to any chromosomes of the HB3, 3D7 or A4 parasites. Other cDNA inserts from the group I clones were also sequenced and examined for chromosome hybridization signals. The λT240 cDNA insert mapped to the var-1/var-2/var-3 cluster on Dd2 chromosome 7 and its sequence matched that of var-3. The λT244, λT284, λT287, λT288, λT295 and λT296 inserts all showed overlapping sequences and yielded the same hybridization patterns. Chromosome sites recognized by these inserts included regions within two SmaI fragments from Dd2 chromosome 7 and another from chromosome 9. We note that loss of a cytoadherence phenotype has been correlated with a chromosome 9 deletion in certain *P. falciparum* lines.

1.8–2.4 kb RNA Transcripts Related to var Exon II

In addition to the 7.5 kb var-7 band, a broad 1.8–2.4 kb band was detected on RNA blots after hybridization with a probe that recognizes var exon II. Sequences of eight group II cDNA inserts homologous to exon II were therefore determined and aligned against the var genes. Comparative analysis of the insert sequences showed that all differed from one another in regions of overlap, indicating that transcription of the corresponding RNAs was from different loci. Three of the cDNA sequences (λT140, λT141 and λT148) aligned downstream of the intron/exon II splice junction. However, five other cDNA inserts (λT142, λT145, λT147, λT150 and λT152) had sequences that aligned upstream of the var intron/exon II splice site and included regions homologous to var intron sequences. In the vicinity of the splice junction, consensus splice sites occurred in three of the cDNA sequences (λT142, λT147, λT150) while a fourth sequence (λT145) showed the required AG dinucleotide but not the expected pyrimidine tract of the splice consensus. The part of the fifth sequence (λT152) that aligned with the var intron extended upstream only to the TAG of the splice sequence. All five sequences lacked a consensus start codon preceded by A+T-rich non-coding DNA that is typical of *P. falciparum* translation start sites.

Isolate-specific var Sequences and Evidence for DNA Recombination in Cultivated Parasite Clones The diversity of var forms expressed by *P. falciparum* parasites reflects a tremendous repertoire in the var gene family. This repertoire is evident in the patterns of restriction polymorphism detected by var probes as well as in the detection of var-specific sequences that hybridize to some parasite DNAs but not to others. The var-7 gene expressed by Dd2, for example, is not present in the HB3, 3D7 or A4 genomes. Such var diversity suggests that frequent DNA rearrangements underlie the production of antigenically variant types in different parasite strains.

To test for DNA rearrangements in parasites cultivated in vitro, we used var sequences to probe restricted DNAs from Dd2 lines adapted to neuraminidase-treated erythrocytes. In one rearrangement a novel 35 kb BglI fragment is seen in NM1 DNA probed with the λT142 (group II) insert. In another rearrangement a deletion of a 20 kb PstI band is evident in NM8 DNA probed with a var-7 sequence. Deletion of this 20 kb band was also detected in the Dd2/R8 subclone obtained before neuraminidase selection, indicating that the DNA rearrangement was not produced by selection in neuraminidase-treated erythrocytes.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A pharmaceutical composition comprising a pharmaceutically acceptable carrier and an isolated polypeptide comprising and ebl-1 polypeptide sequence.

2. The pharmaceutical composition of claim 1, wherein the ebl-1 polypeptide sequence is encoded by the sequence of SEQ ID NO:5.

3. The pharmaceutical composition of claim 1, wherein the ebl-1 polypeptide sequence comprises the sequence of SEQ ID NO:6.

4. The pharmaceutical composition of claim 1, further comprising an isolated Duffy Antigen Binding Protein (DABP) binding domain polypeptide in an amount sufficient to induce a protective immune response to *Plasmodium vivax* merozoites in a mammal.

5. An isolated polypeptide comprising an ebl-1 polypeptide sequence.

6. The isolated polypeptide of claim 5, wherein the ebl-1 polypeptide sequence is encoded by the sequence of SEQ ID NO:5.

7. The isolated polypeptide of claim 5, wherein the ebl-1 polypeptide sequence comprises the sequence of SEQ ID NO:6.

8. An isolated nucleic acid sequence comprising an ebl-1 nucleic acid sequence.

9. The isolated nucleic acid sequence of claim 8, wherein the ebl-1 nucleic acid sequence comprises the sequence of SEQ ID NO:5.

10. A vector comprising an ebl-1 nucleic acid sequence.

11. The vector of claim 10, wherein the ebl-1 nucleic acid sequence comprises the sequence of SEQ ID NO:5.

12. A recombinant host cell comprising an ebl-1 nucleic acid sequence.

13. The recombinant host cell of claim 12, wherein the nucleic acid sequence comprises the sequence of SEQ ID NO:5.

14. The recombinant host cell of claim 12, wherein the host cell produces an amino acid sequence comprising the sequence of SEQ ID NO:6.

15. A recombinant host cell comprising the vector of claim 10.

16. A method for an immune response to *Plasmodium falciparum* merozoites in a patient, the method comprising administration to the patient of an immunologically effective amount of a pharmaceutical composition comprising a pharmaceutically acceptable carrier and an isolated polypeptide comprising an ebl-1 polypeptide sequence.

17. The method of claim 16, wherein the ebl-1 polypeptide sequence is encoded by the sequence of SEQ ID NO:5.

18. The method of claim 16, wherein the ebl-1 polypeptide sequence comprises the sequence of SEQ ID NO:6.

19. The method of claim 16, further comprising administration to the patient of an immunologically effective amount of an isolated Duffy Antigen Binding Protein (DABP) binding domain polypeptide.

20. A recombinant method for making an ebl-1 polypeptide, comprising:

expressing the vector of claim 10 in a host cell; and
isolating an ebl-1 polypeptide from said host cell.

* * * * *